US007268119B2

(12) United States Patent
Cook et al.

(10) Patent No.: US 7,268,119 B2
(45) Date of Patent: *Sep. 11, 2007

(54) TRICYCLIC NUCLEOSIDES OR NUCLEOTIDES AS THERAPEUTIC AGENTS

(75) Inventors: Phillip Dan Cook, Fallbrook, CA (US); Gregory Ewing, deceased, late of Oceanside, CA (US); by Deborah K. Ewing, legal representative, Oceanside, CA (US); Yi Jin, Carlsbad, CA (US); John Lambert, Blackburn South (AU); Marija Prhavc, Encinitas, CA (US); Vasanthankumar Rajappan, Carlsbad, CA (US); Vivek K. Rajwanshi, Vista, CA (US); Kandasamy Sakthivel, Karur (IN)

(73) Assignee: Biota Scientific Management Pty Ltd, Notting Hill (AU)

( * ) Notice: Subject to any disclaimer, the term of this patent is extended or adjusted under 35 U.S.C. 154(b) by 0 days.

This patent is subject to a terminal disclaimer.

(21) Appl. No.: 11/674,954

(22) Filed: Feb. 14, 2007

(65) Prior Publication Data

US 2007/0135363 A1 Jun. 14, 2007

Related U.S. Application Data

(63) Continuation of application No. 10/568,917, filed as application No. PCT/US04/27819 on Aug. 27, 2004.

(60) Provisional application No. 60/498,425, filed on Aug. 27, 2003.

(51) Int. Cl.
*A61K 31/7052* (2006.01)
*C07H 19/23* (2006.01)
*C07H 19/044* (2006.01)

(52) U.S. Cl. ............... 514/43; 514/52; 536/26.1; 536/26.2; 536/26.41; 536/26.9; 536/27.1; 536/28.7

(58) Field of Classification Search ............ 536/28.7; 514/43, 52, 28.7
See application file for complete search history.

(56) References Cited

U.S. PATENT DOCUMENTS

| 6,600,028 B1 * | 7/2003 | Brown et al. ............... 536/23.1 |
| 2003/0008841 A1 | 1/2003 | Devos et al. |
| 2006/0252715 A1 * | 11/2006 | Keicher et al. ............... 514/43 |

FOREIGN PATENT DOCUMENTS

| WO | WO 98/43991 A1 | 10/1998 |
| WO | WO 99/43691 A1 | 9/1999 |
| WO | WO 01/32153 A2 | 5/2001 |
| WO | WO 01/60315 A2 | 8/2001 |
| WO | WO 01/79246 A2 | 10/2001 |
| WO | WO 01/90121 A2 | 11/2001 |
| WO | WO 01/92282 A2 | 12/2001 |
| WO | WO 02/18404 A2 | 3/2002 |
| WO | WO 02/057287 A2 | 7/2002 |
| WO | WO 02/057425 A2 | 7/2002 |
| WO | WO 03/061385 A1 | 7/2003 |
| WO | WO 2006/093986 A1 | 9/2006 |
| WO | WO 2006/093987 A1 | 9/2006 |

OTHER PUBLICATIONS

U.S. Appl. No. 10/568,917, filed Feb. 2006, Cook.*
Silverman, R., The Organic Chemistry of Drug Design and Drug Action, ((1992) published by Academic Press, pp. 19-21 and 352-397.*
Poizot-Martin et al., "Efficacy and Tolerance of HCV Treatment in HIV-HCV Coinfected Patients: The Potential Interaction of PI Treatment" HIV Clinical Trials (2003) vol. 4, No. 4, pp. 262-268.*
STN Database Accession No. 847819-10-7, Apr. 3, 2005.
Araujo et al., "Synthesis and Applications of a Tricyclic Analogue of N6-Methoxy-2,6-Diamino-2'-Deoxyriboside", Collection Symposium Series, 5:328-331, 2002.
Delaney et al., "Resistance of hepatitis B virus to antiviral drugs: current aspects and directions for future investigation," Antiviral Chemistry & Chemotherapy 12(1):1-35, 2001.
Dymock et al., "Novel approaches to the treatment of hepatitis C virus infection," Antiviral Chemistry & Chemotherapy 11(2):79-96, 2000.
Hill et al., "Synthesis and Polymerase Incorporation Properties of a Tricyclic Pyrrolopyrimidine Related to N6-Hydroxy-2'-Deoxyadenosine", Nucleosides & Nucleotides 18(4&5):573-574, 1999.
Porcari et al., "Acyclic Sugar Analogs of Triciribine: Lack of Antiviral and Antiproliferative Activity Correlate with Low Intracellular Phosphorylation," Nucleosides & Nucleotides 18(11 &12):2475-2497, 1999.
Porcari et al., "Deoxy Sugar Analogues of Triciribine: Correlation of Antiviral and Antiproliferative Activity with Intracellular Phosphorylation," J. Med. Chem. 43:2438-2448, 2000.
Porcari et al., "6-N-Acyltriciribine Analogues: Structure-Activity Relationship between Acyl Carbon Chain Length and Activity against HIV-1," J. Med. Chem. 43:2457-2463, 2000.
Seela et al., "Synthesis of 7-alkynylated 8-aza-7-deaza-2'-deoxyadenosines via the Pd-catalysed cross-coupling reaction", J. Chem. Soc., Perkin Trans. 1:3233-3239, 1998.
Seela et al., "7-Substituted 7-Deaza-2'-deoxyadenosines and 8-Aza-7-deaza-2'-deoxyadenosines: Fluorescence of DNA-Base Analogues Induced by the 7-Alkynyl Side Chain", Helvetica Chimica Acta, 83:910-927, 2000.
Williams et al., "Synthesis of a hydrogen-bond-degenerate tricyclic pyrrolopyrimidine nucleoside and of its 5'-triphosphate", J. Chem. Soc., Perkin Trans. 1:3565-3570, 1998.

* cited by examiner

*Primary Examiner*—Shaojia Anna Jiang
*Assistant Examiner*—Eric S Olson
(74) *Attorney, Agent, or Firm*—Seed IP Law Group PLLC

(57) ABSTRACT

Nucleosides and nucleotides containing a tricyclic base portion thereof are useful for treating infectious diseases and proliferative disorders, such as viral infections or cancer respectively.

19 Claims, No Drawings

TRICYCLIC NUCLEOSIDES OR NUCLEOTIDES AS THERAPEUTIC AGENTS

RELATED APPLICATION

This application is a continuation of U.S. application Ser. No. 10/568,917, now pending, which is a U.S. National Stage of PCT/US2004/027819, accorded an International Filing Date of Aug. 27, 2004, which claims the benefit under 35 USC 119(e) of U.S. Provisional Application No. 60/498,425 filed Aug. 27, 2003; all of these applications are incorporated herein by reference in their entireties.

FIELD OF THE INVENTION

The present invention relates to novel tricyclic nucleosides and nucleotides, their preparation, and their use for the treatment of infectious disease, including viral infections, and of proliferative disorders, including cancer.

BACKGROUND OF THE INVENTION

Viral infections are a major threat to human health and account for many serious infectious diseases. Hepatitis C virus (HCV), a major cause of viral hepatitis, has infected more than 200 million people worldwide. Current treatment for HCV infection is restricted to immunotherapy with interferon-α alone or in combination with ribavirin, a nucleoside analog. This treatment is effective in only about half the patient population. Therefore, there is an urgent need for new HCV drugs. Hepatitis C virus comprises a positive-strand RNA genome enclosed in a nucleocapsid and lipid envelope and consists of approximately 9600 ribonucleotides, which encodes a polyprotein of about 3000 amino acids (Dymock et al. *Antiviral Chemistry & Chemotherapy* 2000, 11, 79). A HCV protein, NS5B, released from the polyprotein, possesses polymerase activity and is involved in the synthesis of double-stranded RNA from the single-stranded viral RNA genome that serves as the template. The reproduction of HCV virus may be prevented through the manipulation of NS5B's polymerase activity. The competitive inhibition of NS5B protein would suppress or prevent the formation of the double-stranded HCV RNA. Alternatively, a nucleoside analog also may be incorporated into the extending RNA strand and act as a chain-terminator. Furthermore, a deteriorating nucleoside analog also may be incorporated into the extending RNA, which may cause mutagenic damage to the viral genome. Recently, several PCT patent applications (WO 99/43691, WO 01/32153, WO 01/60315, WO 01/79246, WO 01/90121, WO 01/92282, WO 02/18404, WO 02/057287, WO 02/057425) have described nucleoside analogs as anti-HCV agents in in vitro assays.

Hepatitis B virus (HBV) has acutely infected almost a third of the world's human population, and about 5% of the infected are chronic carriers of the virus (Delaney IV et al. *Antiviral Chemistry & Chemotherapy* 2001, 12, 1-35). Chronic HBV infection causes liver damage that frequently progresses to cirrhosis and/or liver cancer later in the life. Despite the availability and widespread use of effective vaccines and chemotherapy, the number of chronic carriers approaches 400 million worldwide. Therefore, more effective anti-HBV drugs need to be developed. Human immunodeficiency virus (HIV) causes progressive degeneration of the immune system, leading to the development of AIDS. A number of drugs have been used clinically, including reverse transcriptase inhibitors and protease inhibitors. Currently, combination therapies are used widely for the treatment of AIDS in order to reduce the drug resistance. Despite the progress in the development of anti-HIV drugs, AIDS is still one of the leading epidemic diseases. Certain acute viral infections also impose a great threat to human life, including the newly-discovered West Nile virus and SARS virus.

Bacterial infections long have been the sources of many infectious diseases. The widespread use of antibiotics produces many new strains of life-threatening bacteria Fungal infections are another type of infectious diseases, some of which also can be life-threatening. There is an increasing demand for the treatment of bacterial and fungal infections. Antimicrobial drugs based on new mechanisms of action are especially important.

Proliferative disorders are one of the major life-threatening diseases and have been intensively investigated for decades. Cancer now is the second leading cause of death in the United States, and over 500,000 people die annually from this proliferative disorder. All of the various cells types of the body can be transformed into benign or malignant tumor cells. Transformation of normal cells into cancer cells is a complex process and thus far is not fully understood. The treatment of cancer consists of surgery, radiation, and chemotherapy. While chemotherapy can be used to treat all types of cancer, surgery and radiation therapy are limited to certain cancer at certain sites of the body. There are a number of anticancer drugs widely used clinically. Among them are alkylating agent such as cisplatin, antimetabolites, such as 5-fluorouracil, and gemcitabine. Although surgery, radiation, and chemotherapies are available to treat cancer patients, there is no cure for cancer at the present time. Cancer research is still one of the most important tasks in medical and pharmaceutical organizations.

Nucleoside drugs have been used clinically for the treatment of viral infections and proliferative disorders for decades. Most of the nucleoside drugs are classified as antimetabolites. After they enter cells, nucleoside analogs are phosphorylated successively to nucleoside 5'-monophosphates, 5'-diphosphates, and 5'-triphosphates. In most cases, nucleoside triphosphates, e.g., 3'-azido-3'-deoxythymidine (AZT, an anti-HIV drug) triphosphate and arabinosylcytosine (cytarabine, an anticancer drug) triphosphate, are the active chemical entities that inhibit DNA or RNA synthesis, through a competitive inhibition of polymerases and subsequent incorporation of modified nucleotides into DNA or RNA sequences. In a few cases, nucleoside analogs exert effects at lower phosphate levels. For instance, 5-fluoro-2'-deoxyuridine (an anticancer drug) 5'-monophosphate and 2',2'-difluoro-2'-deoxycytidine (an anticancer drug) 5'-diphosphate have been shown to inhibit thymidylate synthase and ribonucleotide reductase, respectively. Although nucleoside analogs themselves may act at the nonphosphate level such as the inhibitors of adenosine kinases and the ligands of adenosine receptors, currently, clinically-useful nucleoside drugs primarily depend on cellular activation by nucleoside kinases and nucleotide kinases.

At least, two criteria are pertinent for nucleoside antiviral drugs: 1. nucleoside analogs should anabolize to nucleotides in cells; and 2. the anabolized nucleotides should target selectively viral enzymes. In order to be phosphorylated in cells and selectively to target preferred enzymes, nucleoside analogs should have favorable modifications on their sugar and base moieties. To obtain such favorable nucleoside analogs, a general approach is to generate diverse nucleoside analogs by modifying the base or the sugar, or by modifying both base and sugar moieties. Numerous examples exist in the literature for the synthesis of a variety of modified nucleosides (*Chemistry of Nucleosides and Nucleotides* Vol. 1 (1988), Vol. 2 (1991), Vol. 3 (1994), edited by Leroy B. Townsend, Plenum Press).

However, there are certain classes of nucleoside compounds that were not explored intensively for their antiviral and anti-proliferative activities before the present invention. A class of such compounds is tricyclic nucleosides. Disclosures on tricyclic nucleosides are very limited considering the existence of various tricyclic heterocycles. A well-known tricyclic nucleoside is triciribine (TCN), having potent cytotoxicity against cancer cells (Porcari et al. *J. Med. Chem.* 2000, 43, 2438-2448). A number of its modified derivatives were prepared and screened against viruses and cancer (Porcari et al. *Nucleosides Nucleotides* 1999, 18, 2475-2497; *J. Med. Chem.* 2000, 43, 2457-2463). Another known tricyclic nucleoside is 2-(2-deoxy-β-D-erythro-pentofuranosyl)-2,6-dihydro-7H-2,3,5,6-tetraazabenz[cd]azulen-7-one, but its biological activity was not reported (*Helv. Chim. Acta*, 2000, 83, 911-927). The PCT publication WO 03/061385 describes tricyclic nucleoside libraries. The present invention discloses novel tricyclic nucleosides and nucleotides and their use for the treatment of infectious disease, including viral infections, and of proliferative disorders, including cancer.

SUMMARY OF THE INVENTION

The present invention relates to novel tricyclic nucleosides and derivatives thereof, their preparation, and their use for the treatment of viral infections and proliferative disorders.

In one embodiment, a compound of the formula (I) which may be a D- or L-nucleoside is provided

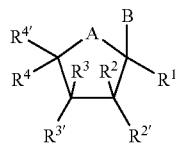

(I)

wherein

A is O, S, $CH_2$, CHF, or $CF_2$;

$R^1$, $R^2$, $R^{2'}$, $R^3$, $R^{3'}$, and $R^4$ are independently selected from the group consisting of H, F, Cl, Br, I, OH, SH, $NH_2$, NHOH, $NHNH_2$, $N_3$, COOH, CN, $CONH_2$, C(S)$NH_2$, COOR, R, OR, SR, SSR, NHR, and $NR_2$;

$R^{4'}$ is -L-$R^5$;

L is selected from the group consisting of O, S, NH, NR, $CY_2O$, $CY_2S$, $CY_2NH$, $CY_2$, $CY_2CY_2$, $CY_2OCY_2$, $CY_2SCY_2$, and $CY_2NHCY_2$, wherein Y is selected from the group consisting of H, F, Cl, Br, alkyl, alkenyl, and alkynyl, wherein alkyl, alkenyl, and alkynyl may each optionally contain one or more heteroatoms;

$R^5$ is OH, monophosphate, diphosphate, or triphosphate, optionally masked with prodrug moieties, or a mono di or triphosphate mimic;

B is a base selected from the group of heterocycles consisting of

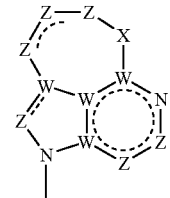

II

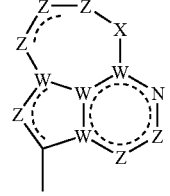

III each Z is independently selected from the group consisting of N, N—$^-BH_2GM^+$, C-G, O, S, NR, >C=O, >C=S, >C=NH, >C=NR, >S=O, >S(O)$_2$ and CH-G;

wherein if Z is a participant in a π bond (double bond), Z is independently N or C-G;

wherein if Z is not a participant in a π bond, Z is independently N—$^-BH_2GM^+$, O, S, NR, >C=O, >C=S, >C=NH, >C=NR, >S=O, >S(O)$_2$ and CH-G;

X is O, S, SO, $SO_2$, Se, SeO, $SeO_2$, NH, or NR;

W is C, CH or N;

wherein if W is a participant in one π bond, W is C;

wherein if W is not a participant in a π bond, W is CH or N; and $^-BH_2GM^+$ is an ion pair and $M^+$ is a cation;

G is selected from the group consisting of H, F, Cl, Br, I, OH, SH, $NH_2$, NHOH, $N_3$, COOH, CN, $CONH_2$, C(S)$NH_2$, C(=NH)$NH_2$, R, OR, SR, NHR, and $NR_2$, when two or more G groups are present on a molecule, they may be same as or different from one another;

R is selected from the group consisting of alkyl, alkenyl, alkynyl, aryl, acyl, and aralkyl, optionally containing one or more heteroatoms;

dashed lines (---) indicate a possible π or double bond.

Thus, structures of formulae II and III may have one or more ring double bonds and, in some instances, may have two or more ring double bonds.

In one preferred embodiment L is $CH_2$.

Preferably W is C. Preferably X is NH.

In another embodiment, the seven-membered ring portion of the base contains one or two and preferably one N in the backbone of the ring.

In another embodiment, the Z in the five-membered ring of the base is C.

In yet another embodiment, each Z in the seven-membered ring portion of the base is preferably C-G, >C=O, >C=S. Preferably CH-G is $CH_2$, CH-halo, and C-G is CH, C-alkyl preferably $CCH_2$, C—OR, preferably, C—O alkyl, more preferably $COCH_3$.

In one embodiment, at least one of $R^2$ or $R^{2'}$ is not H. In another preferred embodiment, the sugar

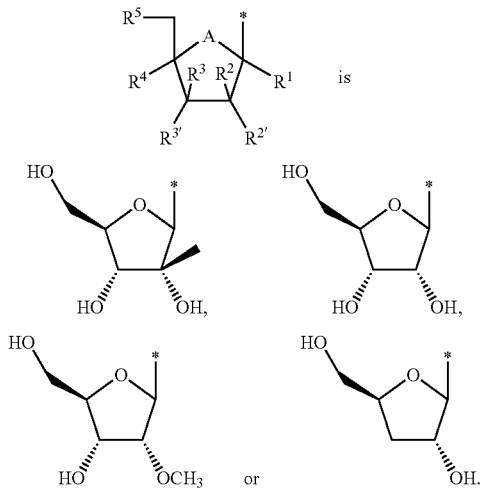

(I)

Thus, compounds of the invention may have the formula

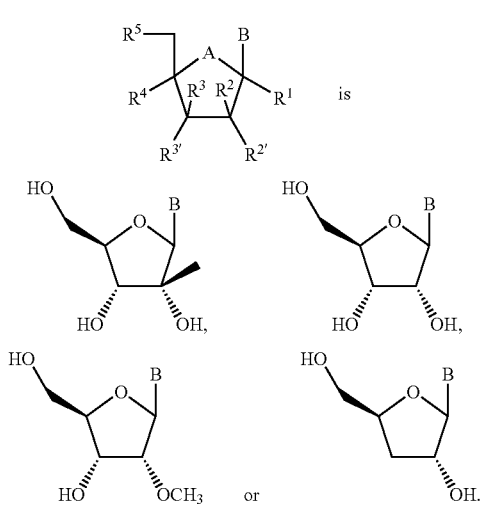

(I)

Some embodiments, in compounds of the invention of formula (I), B is a base selected from the group of heterocycles consisting of

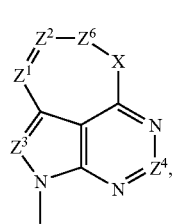

(IV)

-continued

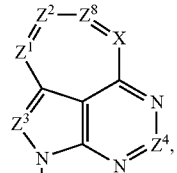

(V)

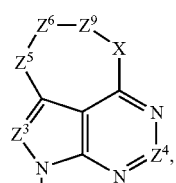

(VI)

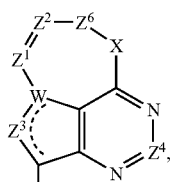

(VII)

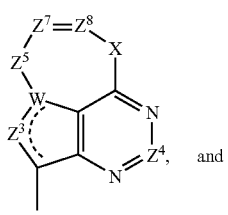

(VIII)

and

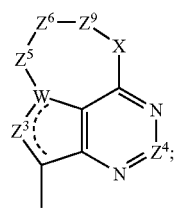

(IX)

$Z^1$, $Z^2$, $Z^3$, $Z^4$, $Z^7$ and $Z^8$ independently N or C-G; and $Z^5$, $Z^6$, and $Z^9$ are independently selected from the group consisting of N—$^-$BH$_2$GM$^+$, O, S, NR, >C=O, >C=S, >C=NH, >C=NR, >S=O, >S(O)$_2$ and CH-G.

In a preferred embodiment, the base is

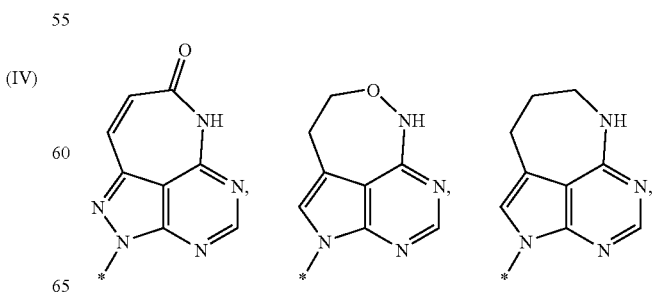

-continued
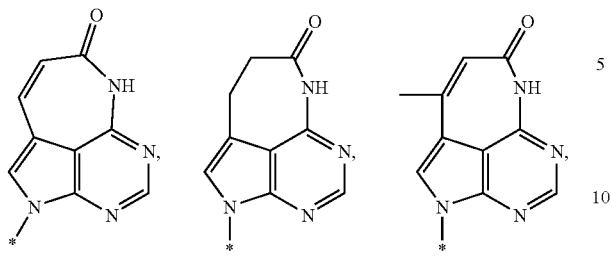
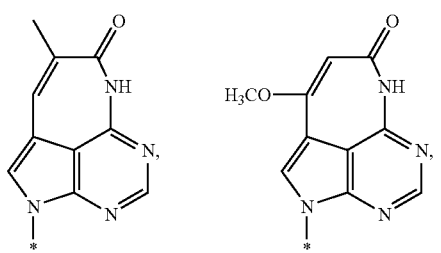
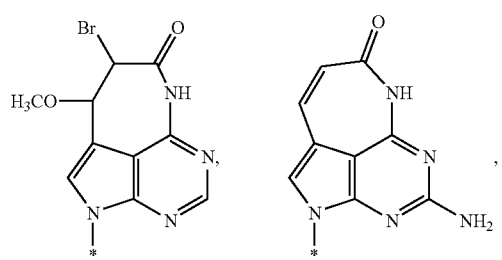
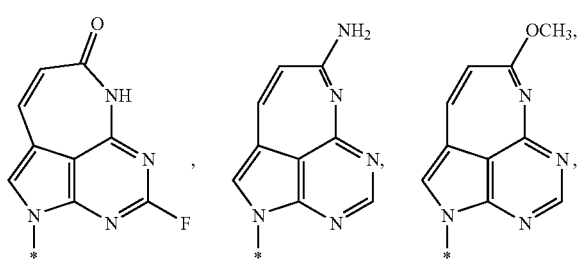
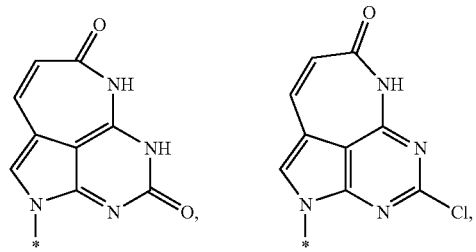
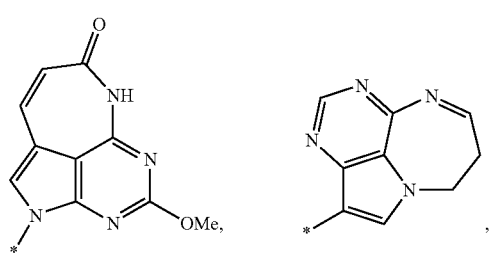
-continued
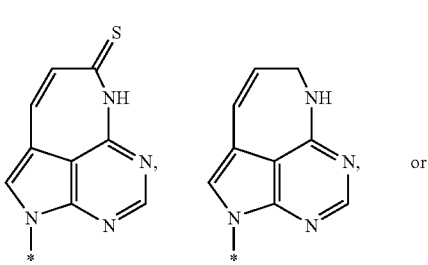
Preferably the compound of the invention is not
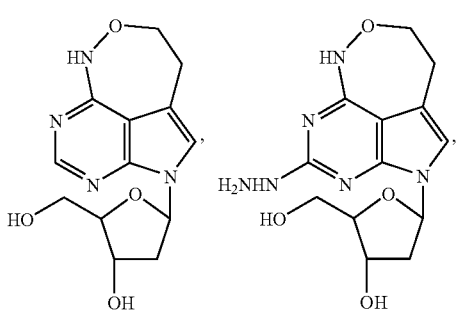
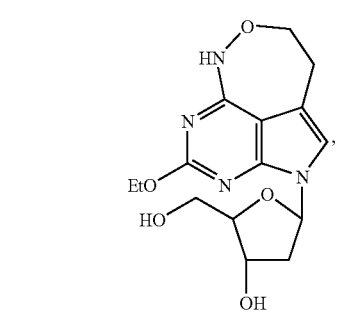
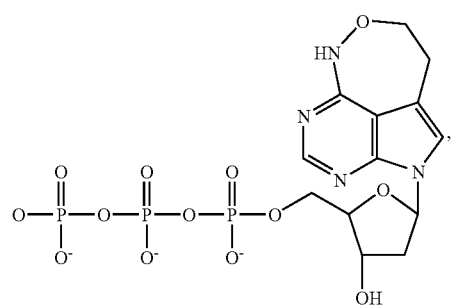

-continued

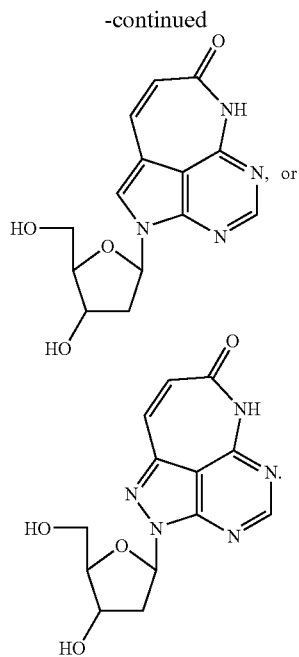

In another aspect the component is not

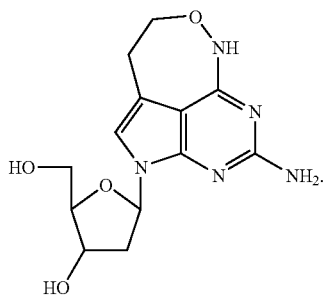

In another embodiment, is provided a method for the treatment of a viral or bacterial infection, or proliferative disorder comprising administering an effective amount of a compound of the formula (I), or a pharmaceutically acceptable salt or a prodrug thereof, optionally in combination with one or more antiviral, antibacterial, or antiproliferative agents. In one aspect, the viral infection is caused by an RNA virus, such as HCV or a DNA or retrovirus such as HBV or HIV.

The invention is also directed to a process of making compounds of the invention.

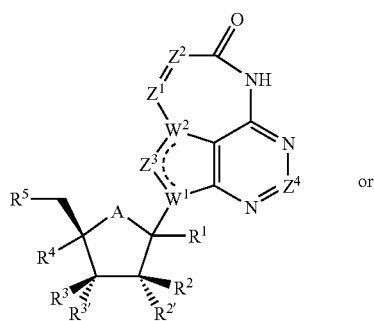

For example, a compound having the formula

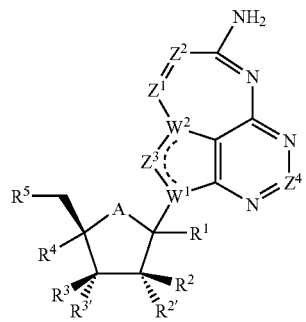

may be made by cyclising a compound having the formula

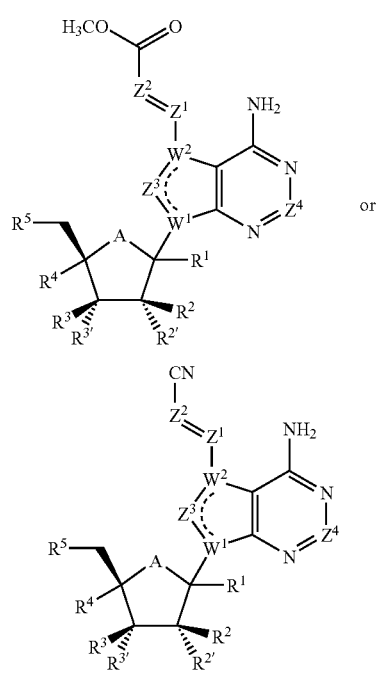

wherein each of $Z^1$-$Z^4$ is independently Z; and wherein each of $W^1$-$W^2$ is independently W. Preferably, in this process A is O, $CH_2$ or optionally protected N;

$W^1$ is C (if p bond) or N (if no p bond);

$W^2$ is C, CH or N;

$W^4$ is H or trialkyltin;

$Z^1$ and $Z^2$ are each independently CH, C-halogen, C-alkyl, C-aryl, C—O-alkyl or C—S-alkyl;

$Z^3$ is CH, C-alkyl, C-halogen, N, CNHR, $CNH_2$, $CNR_2$, C=O, or C=S;

$Z^4$ is CH, C-halogen, C-alkyl, C-aryl, C—O-alkyl, C—S-alkyl, C—OH, C—$NH_2$, C—NHR or C—$NR_2$;

$R^1$, $R^2$, $R^{2'}$, $R^3$, $R^{3'}$, $R^4$ are each independently H, halogen, alkyl, O-alkyl, OH, optionally protected O, methyl, H or F; and $R^5$ is an optionally protected OH or $NH_2$. This process may further comprise reacting

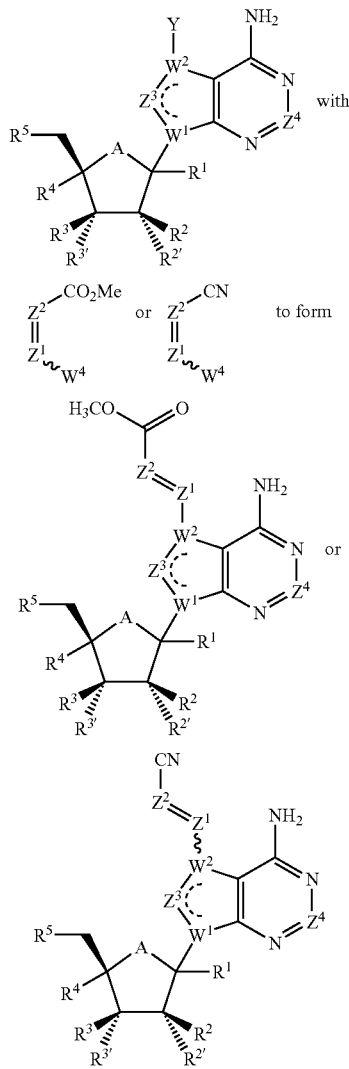

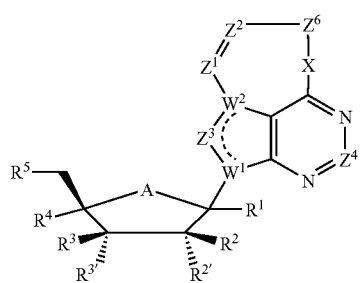

wherein Y is a halogen; and wherein $W^4$ is H or a metal-containing compound capable of metal-mediated cross coupling. The OH and NH groups may be optionally deprotected.

In another embodiment, a process to make comprises cyclising a compound having the formula

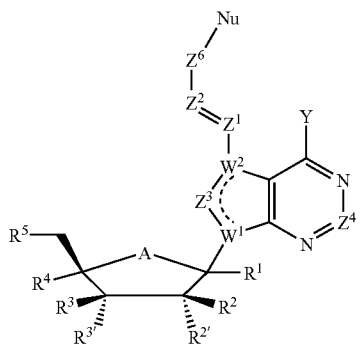

wherein each of $Z^1$-$Z^4$ and $Z^6$ is independently Z;
each of $W^1$ and $W^2$ is independently W;
wherein Y is halogen; and
Nu is a nucleophile. Preferably, A is O, $CH_2$ or optionally protected N;
X is optionally protected N, O, or S;
Nu is an alcohol, an alkylthiol, or an alkylamine;
$W^1$ is C (if p bond) or N (if no p bond);
$W^2$ is C, CH or N;
$Z^1$ and $Z^2$ are each independently CH, C-halogen, C-alkyl, C-aryl, C—O-alkyl, or C—S-alkyl;
$Z^3$ is CH, C-alkyl, C-halogen, N, CNHR, $CNH_2$, $CNR_2$, C=O, or C=S;
$Z^4$ is CH or C-halogen, C-alkyl, C-aryl, C—O-alkyl, C—S-alkyl, C—OH, C—$NH_2$, C—NHR or C—$NR_2$;
$R^1$, $R^2$, $R^{2'}$, $R^3$, $R^{3'}$, $R^4$ are each independently H, halogen, alkyl, O-alkyl, OH, optionally protected O, methyl, or F;
$R^5$ is an optionally protected OH or $NH_2$; and
$Z^6$, is $CH_2$, O, NH, NR or S. This process further comprises reacting

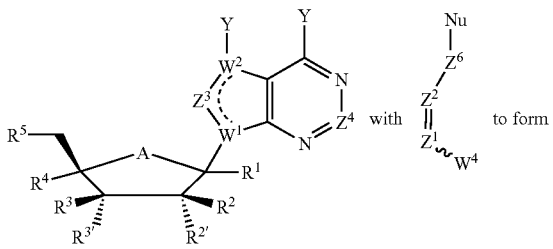

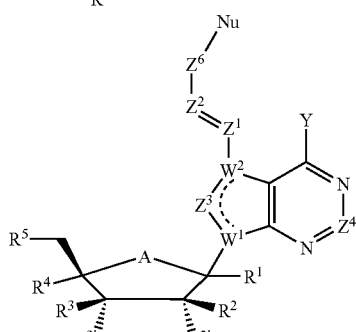

wherein $W^4$ is H or a metal-containing compound capable of cross coupling.

In addition, the compound of the invention may be further modified, for example, to add various functional groups. In one embodiment, a compound having the formula

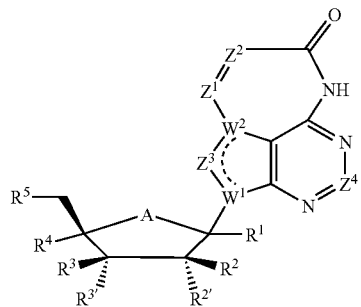

may be modified using a nucleophile and/or electrophile to form a compound selected from the group consisting of:

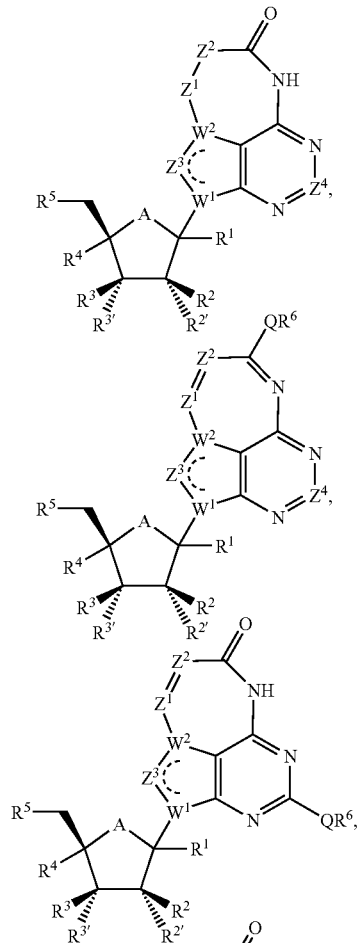

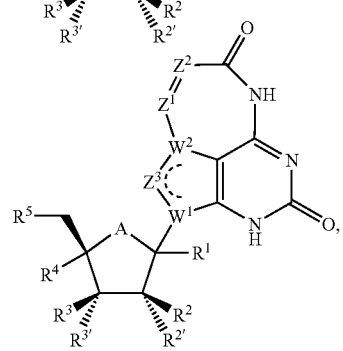

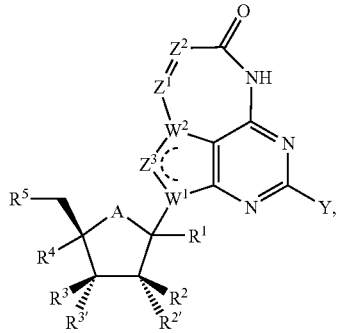

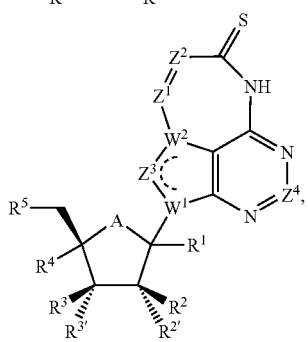

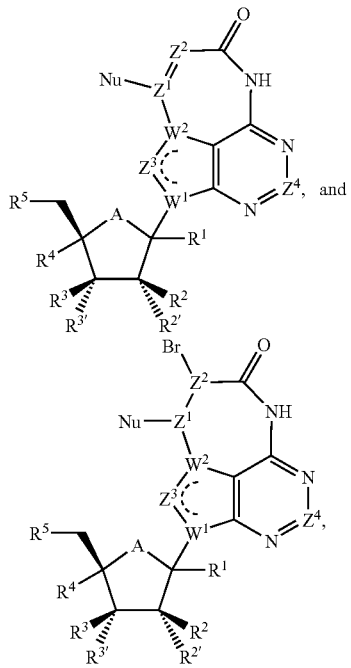

wherein each of $Z^1$-$Z^4$ are independently Z;
wherein each of $W^1$ and $W^2$ are independently W; and
wherein Nu is a nucleophile. Preferably, in this process
A is O, CH$_2$ or optionally protected N;
Nu is an alcohol, an alkylthiol, or an alkylamine;
$W^1$ is C (if p bond) or N (if no p bond);
$W^2$ is C, CH or N;
$Z^1$ and $Z^2$ are each independently CH, C-halogen, C-alkyl, C-aryl, C—O-alkyl, or C—S-alkyl;
$Z^3$ is CH, C-alkyl, C-halogen, N, CNHR, CNH$_2$, CNR$_2$, C=O, or C—S;
$Z^4$ is CH or C-halogen, C-alkyl, C-aryl, C—O-alkyl, C—S-alkyl, C—OH, C—NH$_2$, C—NHR or C—NR$_2$;

$R^1$, $R^2$, $R^{2'}$, $R^3$, $R^{3'}$, $R^4$ are each independently H, halogen, alkyl, O-alkyl, OH, optionally protected O, methyl, or F;

$R^5$ is an optionally protected OH or $NH_2$;

Q is O, NR, NH or S; and $R^6$ is alkyl, aryl, alkenyl or alkynyl.

In another embodiment, a pharmaceutical composition is provided comprising a therapeutically effective amount of a compound of the formula (I) or a pharmaceutically acceptable salt or a prodrug thereof.

DETAILED DESCRIPTION OF THE INVENTION

The tricyclic nucleosides of the invention also include derivatives such as nucleotide mimics and/or prodrugs thereof.

For example, in some embodiments, nucleotide mimics of the compounds of the Invention of formula (I) discussed above include:

a compound in which $R^5$ is a monophosphate mimic of having formula (X) or (XI):

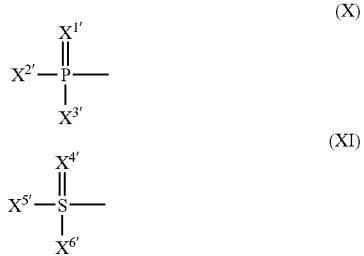

where $X^{1'}$, $X^{4'}$, and $X^{6'}$ independently are O, S, NH, or NR; $X^{2'}$, $X^{3'}$, and $X^{5'}$ are selected independently from the group consisting of H, F, OH, SH, $NH_2$, NHOH, $N_3$, CN, $^-BH_2GM^+$, $^-BH_3M^+$, R, OR, SR, NHR, and $NR_2$. The substituents $^-BH_2GM^+$ and $BH_3M^+$ are ion pairs, which are linked to phosphorus through the negatively charged boron. $M^+$ is a cation.

In some embodiments, nucleotide mimics of the compounds of the Invention of formula (I) discussed above include di- and tri-phosphate mimics including:

a compound in which $R^5$ is a di- or tri-phosphate moiety of formula (XII):

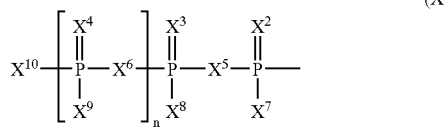

$X^2$, $X^3$, and $X^4$ are selected independently from the group consisting of O, S, Se, NH and NR;

$X^5$ and X are selected independently from the group consisting of O, S, Se, $O_2$, $CY_2CO$, CHOH, $C(OH)_2$, $CH_2O$, $CH_2CH_2$, $CH_2CHNH_2$, $CH_2CH_2CHNH_2$, $CY_2OCY_2$, $CY_2$, CRY, $CY_2CY_2$, CHR, CC, HC=CH, NH, NR, NOH, NOR, $NNH_2$, and NNHR;

Y is selected from the group consisting of H, F, Cl, Br, alkyl, alkenyl, and alkynyl, wherein alkyl, alkenyl, and alkynyl may each optionally contain one or more heteroatoms;

R is selected from the group consisting of alkyl, alkenyl, alkynyl, aryl, acyl, and aralkyl, each optionally containing one or more heteroatoms;

$X^7$, $X^8$, $X^9$, and $X^{10}$ are selected independently from the group consisting of H, F, OH, SH, $NH_2$, NHOH, NHOR, $NHNH_2$, NHNHR, CN, $N_3$, $^-BH_3M^+$, $^-BH_2GM^+$, R, OR, SR, SeH, SeR, NHR, and $NR_2$.

wherein n is 0 or 1. The substituents $BH_2GM^+$ and $^-BH_3M^+$ are ion pairs, which are is linked to phosphorus through the negatively charged boron. $M^+$ is a cation.

Additional nucleotide phosphate mimics and methods of making the phosphate mimics appropriate for the compounds of the invention are described in PCT Publications WO 2003/072757 and WO 2003/073989, filed Feb. 28, 2003, which are incorporated herein by reference in their entirety. Many nucleotide mimics of the present invention can be prepared by similar approaches as published or by using well-known knowledge of organophosphorous chemistry. Generally, phosphate mimics of the nucleosides and nucleotides of the invention can inhibit enzyme function without phosphorylation and/or have enhanced nuclease stability relative to nucleotides with unmodified phosphate.

The term phosphate mimic, unless otherwise specified, refers to a phosphate analog, including, but not limited to, phosphonate, phosphothioate, phosphoselenate, selenophosphate, thiophosphate, P-boranophosphate, phosphoramidate, sulfamate, sulfonate, and sulfonamide and/or a combination thereof. Preferred embodiments of the phosphate mimics include phosphonate, phosphorothioate, methylphosphonate, fluromethylphosphonate, difluoromethylphosphonate, vinylphosphonate, phenylphosphonate, sulfonate, fluorophosphate, dithiophosphorothioate, 5'-methylenephosphonate, 5'-difluoromethylenephosphonate, 5'-deoxyphosponate, 5'-aminophosphoramidate, and 5'-thiophosphate. More preferred is phosphonate.

The terms diphosphate mimic and triphosphate mimic specifically refer to a diphosphate analog and a triphosphate analog, respectively, which comprises at least one of the phosphate mimics, one of the modifications at the bridging site of diphosphate and triphosphate, or replacements of non-bridging phosphate oxygens. The modification at the bridging site, i.e., in the $X^5$ and $X^6$ positions of formula (XII), includes the replacement of O by other atoms or functions such as S, Se, $O_2$, NH, NHR, NR, $CH_2$, CHF, CHCl, CHBr, $CF_2$, $CCl_2$, $CBr_2$, CHR, $CYCO_2$, $CH_2O$, CHOH, $C(OH)_2$, $CH_2CH_2$, CC, CH=CH, $CH_2CH_2CHNH_2$, $CH_2CHNH_2$, $CY_2OCY_2$, $CY_2$, $CY_2CY_2$, and $CR_2$ where R is selected from the group consisting of alkyl, alkenyl, alkynyl, aryl, acyl, and aralkyl each optionally containing one or more heteroatoms. Non-bridging phosphate oxygens, e.g., in $X^7$-$X^{10}$ positions of formula (XII) can be replaced by a variety of substituents including H, F, OH, SH, $NH_2$, NHOH, NHOR, $NHNH_2$, NHNHR, CN, $N_3$, $^-BH_3M^+$, R, OR, SR, SeH, SeR, NHR, $NR_2$, and R* where R is as defined herein, and wherein R* is a prodrug substituent. $M^+$ is a cation preferably a pharmaceutically acceptable cation such as $Ca^{2+}$, ammonium, trialkylammonium or tertaalkylammonium, e.g., $NH_4^+$, $Et_3NH^+$, $Bu_3NH^+$, and $Bu_4N^+$.

The α-P, β-P, and γ-P in the diphosphate mimics and triphosphate mimics may independently adopt either R or S configurations when they become a chiral phosphorus.

In some embodiments, the tricyclic nucleosides and nucleotides of invention also include their prodrug derivatives. In addition to those described herein, prodrug derivatives of nucleosides, nucleotides and nucleotide phosphate mimics and methods of making the prodrugs appropriate for use in the present invention are described in PCT Publications WO 2003/072757 and WO 2003/073989. Such prodrug modification is to enhance drug absorption and/or drug delivery into cells.

In one embodiment, such compounds of the invention include prodrugs (e.g., one or more of an —OH group of a mono, di or triphosphate, one or more of $X^{2'}$, $X^{3'}$ or $X^{5'}$, or $X^7$-$X^{10}$ in (XII) is a prodrug substituent R*) of the compounds of formula (I) discussed herein.

R* is a prodrug substituent which may be conjugated to one or more $X^7$-$X^{10}$ positions. The term prodrug, unless otherwise specified, refers to a masked (protected) form of a nucleotide, such as a mimic of formula (X) or (XI) that is formed when one or more of $X^{2'}$, $X^{3'}$ or $X^{5'}$ is R* or to a masked (protected) form of a nucleotide mimic of formula (XII) when one or more of $X^7$-$X^{10}$ is R*. The prodrug of a nucleoside 5'-monophosphate mimic can mask the negative charges of the phosphate mimic moiety entirely or partially, mask the negative charges of the di-phosphate ($X^7$, $X^8$, $X^{10}$) mimic or tri-phosphate ($X^7$-$X^{10}$) mimic moiety or phosphate moiety, entirely or partially, or mask a heteroatom substituted alkyl, aryl or aryalkyl (W', see below) attached to a phosphate or phosphate mimic moiety in order to enhance drug absorption and/or drug delivery into cells. The prodrug can be activated either by cellular enzymes such as lipases, esterases, reductases, oxidases, nucleases or by chemical cleavage such as hydrolysis to release (liberate) the nucleotide mimic after the prodrug enters cells. Prodrugs are often referred to as cleavable prodrugs. Prodrugs substituents include, but are not limited to: proteins; antibiotics (and antibiotic fragments); D- and L-amino acids attached to a phosphate moiety or a phosphate mimic moiety via a carbon atom (phosphonates), a nitrogen atom phosphoamidates), or an oxygen atom (phosphoesters); peptides (up to 10 amino acids) attached to a phosphate moiety or a phosphate mimic moiety via a carbon atom (phosphonates), a nitrogen atom (phosphoamidates), or an oxygen atom (phosphoesters); drag moieties attached to a phosphate moiety or a phosphate mimic moiety via a carbon atom (phosphonates), a nitrogen atom (phosphoamidates), or an oxygen atom (phosphoesters); steroids; cholesterols; folic acids; vitamins; polyamines; carbohydrates; polyethylene glycols (PEGs); cyclosaligenyls; substituted 4 to 8-membered rings, with or without heteroatom substitutions, 1,3-phosphoamidate attachments to a terminal phosphate or phosphate mimic moiety (γ or β) or connecting between an α, β or β,γ phosphate moiety or phosphate mimic moiety; acylthioethoxy, (SATE) $RCOSCH_2CH_2O$—; $RCOSCH_2CH_2O$—W'—O—; $RCOSCH_2CH_2O$—W'—S—; $RCOSCH_2CH_2O$—W'—NH—; $RCOSCH_2CH_2O$—W'—; $RCOSCH_2CH_2O$—W'—$CY_2$—; acyloxymethoxy, $RCOOCH_2O$—; $RCOOCH_2O$—W'—O—; $RCOOCH_2O$—W'—S—; $RCOOCH_2O$—W'—NH—; $RCOOCH_2O$—W'—; $RCOOCH_2O$—W'—$CY_2$—; alkoxycarbonyloxymethoxy, $ROCOOCH_2O$—; $ROCOOCH_2O$—W'—O—; $ROCOOCH_2O$—W'—S—; $ROCOOCH_2O$—W'—NH—; $ROCOOCH_2O$—W'—; $ROCOOCH_2O$—W'—$CY_2$—; acylthioethyldithioethoxy (DTE) $RCOSCH_2CH_2SSCH_2CH_2O$—; $RCOSCH_2CH_2SSCH_2CH_2O$—W'—; $RCOSCH_2CH_2SSCH_2CH_2O$—W'—O—; $RCOSCH_2CH_2SSCH_2CH_2O$—W'—S—; $RCOSCH_2CH_2SSCH_2CH_2O$—W'—NH—; $RCOSCH_2CH_2SSCH_2CH_2O$—W'—$CY_2$—; acyloxymethylphenylmethoxy (PAOB) $RCO_2$—$C_6H_4$—$CH_2$—O—; $RCO_2$—$C_6H_4$—$CH_2$—O—W'—; $RCO_2$—$C_6H_4$—$CH_2$—O—W'—O—; $RCO_2$—$C_6H_4$—$CH_2$—O—W'—S—; $RCO_2$—$C_6H_4$—$CH_2$—O—W'—NH—; $RCO_2$—$C_6H_4$—$CH_2$—O—W'—$CY_2$—; 1,2-O-diacyl-glyceryloxy, $RCOO$—$CH_2$—CH(OCOR)—$CH_2O$—; 1,2-O-dialkyl-glyceryloxy, RO—$CH_2$—CH(OR)—$CH_2O$—; 1,2-S-dialkyl-glyceryloxy, RS—$CH_2$—CH(SR)—$CH_2O$—; 1-O-alkyl-2-O-acyl-glyceryloxy, RO—$CH_2$—CH(OCOR)—$CH_2O$—; 1-S-alkyl-2-O-acyl-glyceryloxy, RS—$CH_2$—CH(OCOR)—$CH_2O$—; 1-O-acyl-2-O-alky-glyceryloxy, RCOO—$CH_2$—CH(OR)—$CH_2O$—; 1-O-acyl-2-S-alky-kglyceryloxy, RCOO—$CH_2$—CH(SR)—$CH_2O$—; any substituent attached via a carbon, nitrogen or oxygen atom to a nucleoside di- or tri-phosphate mimic that liberates the di- or tri-phosphate mimic in vivo.

A combination of prodrug substituents may be attached (conjugated) to one or more $X^{2'}$, $X^{3'}$ and $X^{5'}$ positions on a nucleoside mono-phosphate mimic or to one or more $X^7$-$X^{10}$ positions on a nucleoside di- or tri-phosphate mimic. W' is alkyl, aryl, aralkyl as described above or a heterocycle. Preferred prodrug substituents (R*) in positions $X^{2'}$, $X^{3'}$ or $X^{5'}$ include 2,3-O-diacylglyceryloxy, 2,3-O-dialkylglyceryloxy, 1-O-alkyl-2-O-acylglyceryloxy, 1-O-acyl-2-O-alkylglyceryloxy, 1-S-alkyl-2-O-acyl-1-thioglyceryloxy, acyloxymethoxy, S-acyl-2-thioethoxy, S-pivaloyl-2-thioethoxy, acyloxymethoxy, pivaloyloxymethoxy, alkoxycarbonyloxymethoxy, S-alkyldithio-S'-ethyoxy acyloxymethoxy, S-acyl-2-thioethoxy, S-pivaloyl-2-thioethoxy, pivaloyloxymethoxy, alkoxycarbolnyloxymethoxy, and S-alkyldithio-S'-ethyoxy.

The term moiety, unless otherwise specified, refers to a portion of a molecule. Moiety may be, but is not limited to, a functional group, an acyclic chain, a prodrug masking group, an aromatic ring, a carbohydrate, a carbocyclic ring, or a heterocycle.

The term base, unless otherwise specified, refers to the base moiety of a nucleoside or nucleotide. The base moiety is the heterocycle portion of a nucleoside or nucleotide. The base moiety of a nucleotide of formula (I) is a tricyclic heterocycle represented by formulae II-III. Preferably, the base moiety of a nucleotide of formula (I) may be a tricyclic heterocycle represented by any one of formulae IV-IX. The nucleoside base is attached to the sugar moiety of a nucleoside in such ways that both β-D- and β-L-nucleoside can be produced.

The term sugar refers to the ribofuranose portion of a nucleoside. The sugar moiety of formula (I) nucleosides and nucleotides mimics and/or prodrugs thereof may contain one or more substituents at their C1-, C2-, C3- and C4-position of the ribofuranose. Substituents may direct to either the α- or β-face of the ribofuranose. The nucleoside base that can be considered as a substituent at the C-1 position of the ribofuranose directs to the β-face of the sugar. The β-face is the side of a ribofuranose on which a purine or pyrimidine base of natural β-D-nucleosides is present. The α-face is the side of the sugar opposite to the β-face. The sugar moiety of the present invention is not limited to a ribofuranose and its derivatives, instead it may be a carbohydrate, a carbohydrate analog, a carbocyclic ring, or other ribofuranose analogs.

The term sugar-modified nucleoside or nucleotide refers to a nucleoside or nucleotide containing a modified sugar moiety.

The term base-modified nucleoside or nucleotide refers to a nucleoside or nucleotide containing a modified base moiety.

The term alkyl, unless otherwise specified, refers to a saturated straight, branched, or cyclic hydrocarbon of C1 to C18. Alkyls may include, but are not limited to, methyl, ethyl, n-propyl, isopropyl, cyclopropyl, n-butyl, isobutyl, t-butyl, cyclobutyl, n-pentyl, isopentyl, neopentyl, cyclopentyl, n-hexyl, cyclohexyl, dodecyl, tetradecyl, hexadecyl, or octadecyl.

The term alkenyl, unless otherwise specified, refers to an unsaturated hydrocarbon of C2 to C18 that contains at least one carbon-carbon double bond and may be straight, branched or cyclic. Alkenyls may include, but are not limited to, olefinic, propenyl, allyl, 1-butenyl, 3-butenyl, 1-pentenyl, 4-pentenyl, 1-hexenyl, or cyclohexenyl.

The term alkynyl, unless otherwise specified, refers to an unsaturated hydrocarbon of C2 to C18 that contains at least one carbon-carbon triple bond and may be straight, branched or cyclic. Alkynyls may include, but are not limited to, ethynyl, 1-propynyl, 2-propynyl, 1-butynyl, or 3-butynyl.

The term aryl, unless otherwise specified, refers to an aromatic moiety with or without one or more heteroatoms. Aryls may include, but are not limited to, phenyl, biphenyl, naphthyl, pyridinyl, pyrrolyl, and imidazolyl optionally containing one or more substituents. The substituents may include, but are not limited to, hydroxy, amino, thio, halogen, cyano, nitro, alkoxy, alkylamino, alkylthio, hydroxycarbonyl, alkoxycarbonyl, or carbamoyl.

The term aralkyl, unless otherwise specified, refers to a moiety that contains both an aryl and an alkyl, an alkenyl, or an alkynyl. Aralkyls can be attached through either the aromatic portion or the non-aromatic portion. Aralkyls may include, but are not limited to, benzyl, phenethyl, phenylpropyl, methylphenyl, ethylphenyl, propylphenyl, butylphenyl, phenylethenyl, phenylpropenyl, phenylethynyl, or phenylpropynyl.

The term acyl, unless otherwise specified, refers to alkylcarbonyl. Acyls may include, but are not limited to, formyl, acetyl, fluoroacetyl, difluoroacetyl, trifluoroacetyl, chloroacetyl, dichloroacetyl, trichloroacetyl, propionyl, benzoyl, toluoyl, butyryl, isobutyryl, or pivaloyl.

The term heteroatom refers to oxygen, sulfur, nitrogen, or halogen. When one or more heteroatoms are attached to alkyl, alkeneyl, alkynyl, acyl, aryl, or arakyl, a new functional group may be produced. For instance, when one or more heteroatoms are attached to an alkyl, substituted alkyls may be produced, including, but not limited to, fluoroalkyl, chloroalkyl, bromoalkyl, iodoalkyl, alkoxy, hydroxyalkyl, alkylamino, aminoalkyl, alkylthio, thioalkyl, azidoalkyl, cyanoalkyl, nitroalkyl, carbamoylalkyl, carboxylalkyl, and acylalkyl.

Benzoazulenes, such as benzo[cd]azulene refer to a class of tricyclic compounds having a fused, 5, 6, and 7-membered rings that may contain one or more heteroatoms, preferably O or N, in the backbone of the ring, and thus derivatives of benzoazulene is also included in such term.

The term halogen or halo refers to fluorine, chlorine, bromine, or iodine.

The term function refers to a substituent. Functions may include, but are not limited to, hydroxy, amino, sulfhydryl, azido, cyano, halo, nitro, hydroxyamino, hydroxycarbonyl, alkoxycarbonyl, or carboxyl either protected or unprotected.

R may be formula (I) is a univalent substituent and present on the base, sugar and other moieties. R may be selected from the group consisting of alkyl, alkenyl, alkynyl, aryl, acyl, and aralkyl optionally containing one or more heteroatoms, which are as defined above.

A "protecting group" for example for O, S, or N such as hydroxy or $NH_2$, includes acyl groups, silyl groups, and the like. Suitable protecting groups are described by Greene, T. W., et al., in *Protecting Groups in Organic Synthesis.* 2$^{nd}$ Ed., John Wiley & Sons, Inc. (1991), incorporated herein by reference. "Nuceophile" and "electrophile" have their ordinary meaning in the art. Examples of preferred nucleophiles are alcohols, alkylthiols or alkylamines, which may be optionally protected. "Nu" refers to both the free nucleophiles and the nucleophiles as attached to the tricyclic compound of the invention. Thus, a nucleophile may be, for example, DMF or MeO—. Preferably, a nucleophile may be optionally protected N, O or S.

In addition to using prodrug approaches, the delivery of the nucleosides and nucleotides may be assisted by using a therapeutically acceptable carrier such as liposomal suspensions, cationic lipids, and polyimines. In compounds of formula (I) where a chiral center is present, the invention encompasses enantiomers, or stereoisomers and mixtures thereof, such as enantiomerically enriched mixtures.

The term "infection" or "microbial infection" refers to the infection caused by an infectious agent or microbe, such as bacteria, parasite (including protozoan), virus or fungus (including unicellular and multicellular). Examples of microbes that cause such infection include: *Acanthamoeba*, African Sleeping Sickness (Trypanosomiasis), amebiasis, American Trypanosomiasis (Chagas Disease), Bilharzia (Schistosomiasis), cryptosporidiosis (diarrheal disease, *Cryptosporidium Parvum*), Giardiasis (diarrheal disease, *Giardia laniblia*), hepatitis A, B, C, D, E, leishmaniasis (skin sores and visceral), malaria (*Plasmodium falciparum*), *Salmonella enteritides* infection (stomach cramps, diarrhea and fever), tuberculosis (*mycobacterium tuberculosis*), varicella (chicken pox), yellow fever, pneumonias, urinary tract infections (*Chlamydia* and *Mycoplasma*), meningitis and meningococcal septicemia, skin and soft tissue infections (*Staphylococcus aureus*), lower respiratory tract infections (bacterial pathogens or hepatitis C).

Common infections caused by microbes are further outlined in the following chart:

| Infection | Bacteria | Fungus | Protozoa | Virus |
| --- | --- | --- | --- | --- |
| AIDS | | | | X |
| Athlete's Foot | | X | | |
| Chicken Pox | | | | X |
| Common Cold | | | | X |
| Diarrheal Disease | X | | X | X |
| Flu | | | | X |
| Genital Herpes | | | | X |
| Malaria | X | | X | |
| Meningitis | X | | | |
| Pneumonia | X | X | | |
| Sinusitis | X | X | | |
| Skin Disease | X | X | X | X |
| Strep Throat | X | | | |
| Tuberculosis | X | | | |
| Urinary Tract Infections | X | | | |
| Vaginal Infections | X | X | | |
| Viral Hepatitis | | | | X |

Chemical Synthesis

The novel nucleosides and nucleotides, and prodrugs thereof, of the present invention can be prepared by those who are skillful in synthetic organic and nucleoside chemistry using established synthetic methodology (*Chemistry of Nucleosides and Nucleotides* Vol. 1, 2, 3, edited by Townsend, Plenum Press; *Handbook of Nucleoside Synthesis* by Vorbrüggen Ruh-Pohlenz, John Wiley & Sons, Inc., 2001; *The Organic Chemistry of Nucleic Acids* by Yoshihisa Mizuno, Elsevier, 1986). The nucleosides of the present invention can be converted to their corresponding monophosphate, diphosphate, and triphosphate by established phosphorylation procedures. Similarly, known methods in the art can be used to synthesize the nucleotide prodrugs and phosphate mimics. The following schemes and descriptions serve as representative syntheses of the nucleosides of the present invention. As such, other compounds such as those having -L-R$^{4'}$ groups other than CH$_2$R$^5$ may similarly be made.

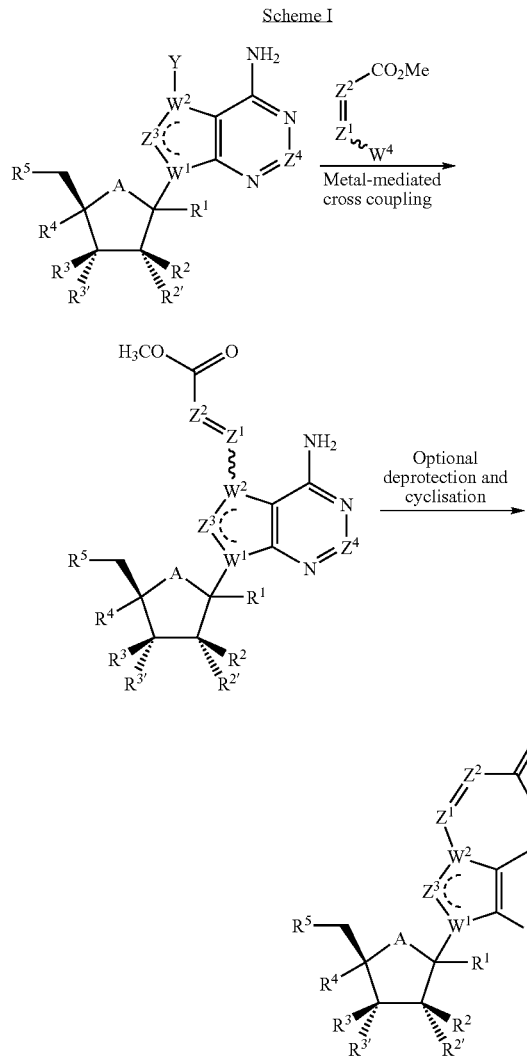

Gycosyl benzo[cd]azulenes can be prepared by modification of optionally protected and functionalized 7-deazapunrine analogues followed by Stille, Heck or other metal-mediated cross coupling chemistry to introduce an α,β-unsaturated ester or other carbonyl group. Such process allows for stereoselective synthesis of an intermediate capable of efficient cyclisation to the inventive compound. Any compound capable of metal-mediated cross coupling may be used, such as a tin derivative, such as trialkyltin. More preferably tributyltin. Cyclisation and optional deprotection of the product delivers the target nucleoside which contains the benzo[cd]azulene, a key element of the invention.

In Scheme 1, preferably A is O, CH$_2$ or optionally protected N; Y is halogen; W$^1$ is C (if p bond) or N (if no p bond); W$^2$ is C, CH or N; W$^4$ is H or trialkyltin; Z$^1$ and Z$^2$ are each independently CH, C-halogen, C-alkyl, C-aryl, C—O-alkyl or C—S-alkyl; Z$^3$ is CH, C-alkyl, C-halogen, N, CNHR, CNH$_2$, CNR$_2$, C=O, or C=S; Z$^4$ is CH, C-halogen, C-alkyl, C-aryl, C—O-alkyl, C—S-alkyl, C—OH, C—NH$_2$, C—NHR or C—NR$_2$; R$^1$, R$^2$, R$^{2'}$, R$^3$, R$^{3'}$, R$^4$ are each independently H, halogen, alkyl, O-alkyl, OH, optionally protected O, methyl, H or F; R$^5$ is an optionally protected OH or NH$_2$.

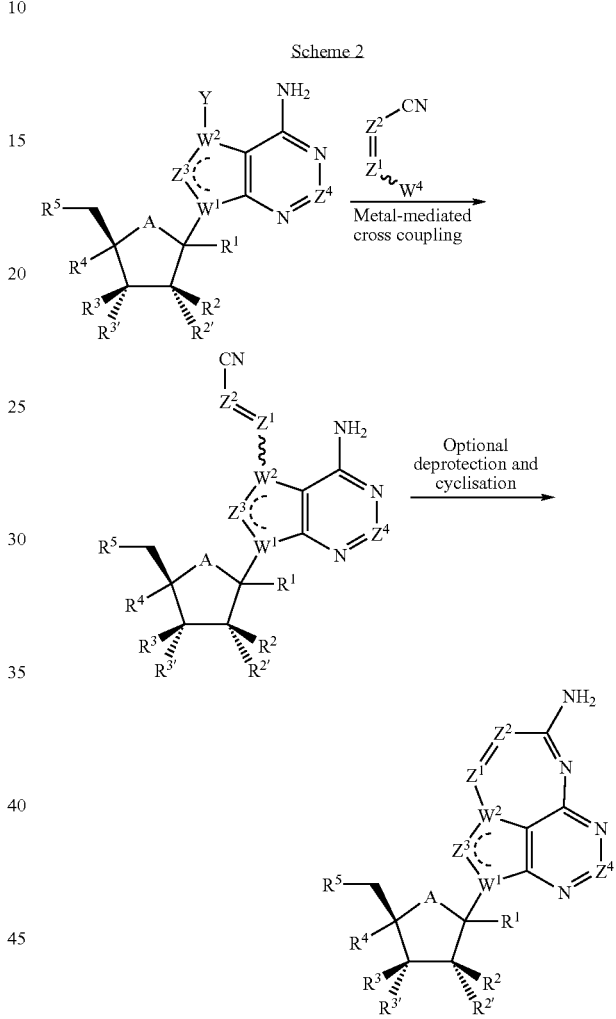

An alternative to the use of vinyl esters in the metal-mediated cross coupling is the use of vinyl nitriles. In this case, cyclisation and optional deprotection of the product delivers the target nucleoside in the form of an amidine-containing benzo[cd]azulene.

In Scheme 2, preferably A is O, CH$_2$ or optionally protected N; Y is halogen; W$^1$ is C (if p bond) or N (if no p bond); W$^2$ is C, CH or N; W$^4$ is H or trialkyltin; Z$^1$ and Z$^2$ are each independently CH, C-halogen, C-alkyl, C-aryl, C—O-alkyl or C—S-alkyl; Z$^3$ is CH, C-alkyl, C-halogen, N, CNHR, CNH$_2$, CNR$_2$, C=O, or C=S; Z$^4$ is CH, C-halogen, C-alkyl, C-aryl, C—O-alkyl, C—S-alkyl, C—OH, C—NH$_2$, C—NHR or C—NR$_2$; R$^1$, R$^2$, R$^{2'}$, R$^3$, R$^{3'}$, R$^4$ are each independently H, halogen, alkyl, O-alkyl, OH, optionally protected O, methyl, or F; R$^5$ is an optionally protected OH or NH$_2$.

Scheme 3

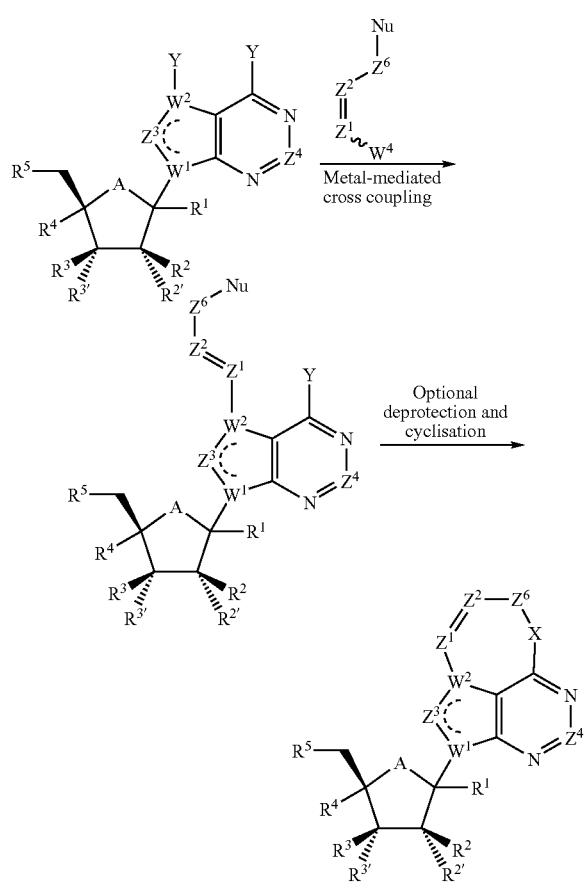

Similar cross-coupling methodology can be applied where the alkene partner in the cross-coupling reaction is equipped with a nucleophile which may be present in protected form. Intramolecular nucleophilic substitution by the pendant nucleophile delivers the requisite benzo[cd] azulene. SNAr displacement reactions are an example of such nucleophilic substitutions.

In Scheme 3, preferably A is O, $CH_2$ or optionally protected N; Y is halogen; X is optionally protected N, O or S; $W^1$ is C (if p bond) or N (if no p bond); $W^2$ is C, CH or N; $W^4$ is H or trialkyltin; $Z^1$ and $Z^2$ are each independently CH, C-halogen, C-alkyl, C-aryl, C—O-alkyl or C—S-alkyl; $Z^3$ is CH, C-alkyl, C-halogen, N, CNHR, $CNH_2$, $CNR_2$, C=O, or C=S; $Z^4$ is CH or C-halogen, C-alkyl, C-aryl, C—O-alkyl, C—S-alkyl, C—$NH_2$, C—NHR or C—$NR_2$; $Z^6$ is $CH_2$, O, NH or NR; $R^1$, $R^2$, $R^{2'}$, $R^3$, $R^{3'}$, $R^4$ are each independently H, halogen, alkyl, O-alkyl, OH, optionally protected O, methyl, or F; $R^5$ is an optionally protected OH or $NH_2$; Nu is optionally protected N, O, or S.

Scheme 4

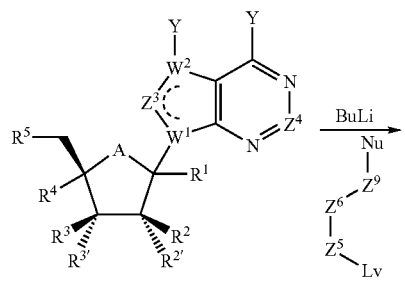

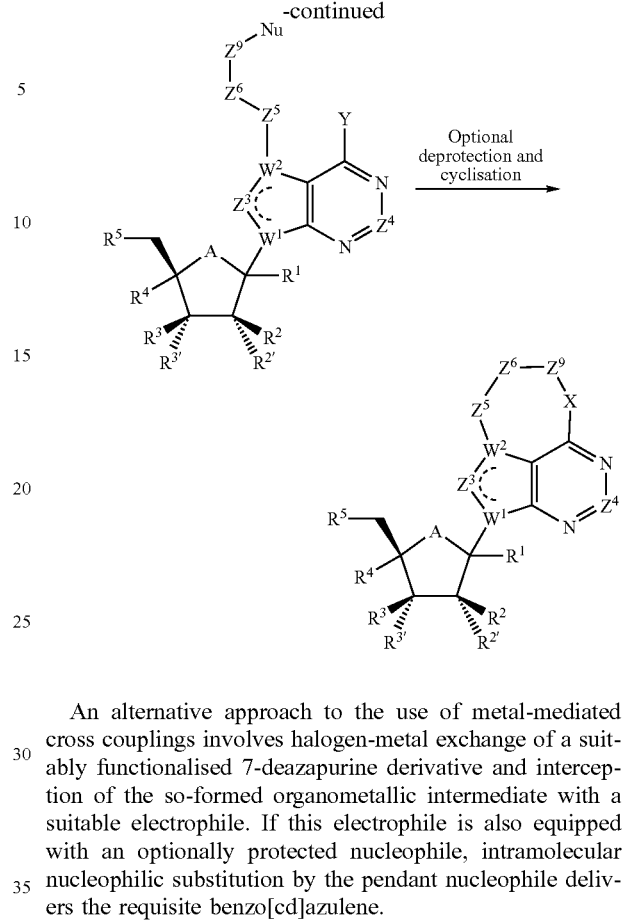

An alternative approach to the use of metal-mediated cross couplings involves halogen-metal exchange of a suitably functionalised 7-deazapurine derivative and interception of the so-formed organometallic intermediate with a suitable electrophile. If this electrophile is also equipped with an optionally protected nucleophile, intramolecular nucleophilic substitution by the pendant nucleophile delivers the requisite benzo[cd]azulene.

In Scheme 4, preferably A is O, $CH_2$ or optionally protected N; Y is halogen; X is optionally protected N, O or S; $W^1$ is C (if p bond) or N (if no p bond); $W^2$ is C, CH or N; $W^4$ is H or trialkyltin; $Z^3$ is CH, C-alkyl, C-halogen, N, CNHR, $CNH_2$, $CNR_2$, C=O, or C=S; $Z^4$ is CH or C-halogen, C-alkyl, C-aryl, C—O-alkyl, C—S-alkyl, C—$NH_2$, C—NHR or C—$NR_2$; $Z^5$ $Z^6$ $Z^9$ are each independently $CH_2$, O, NH or NR; $R^1$, $R^2$, $R^{2'}$, $R^3$, $R^{3'}$, $R^4$ are each independently H, halogen, alkyl, O-alkyl, OH, optionally protected O, methyl, or F; $R^5$ is an optionally protected OH or $NH_2$; Nu is a nucleophile such as optionally protected N, O, or S; Lv is Leaving group.

Gycosyl benzo[cd]azulenes can alternatively be prepared by glycosylation of intact benzo[cd]azulenes as shown in Scheme 2. Conditions used for such glycosidations are well known to practitioners of the art and can be found in the references cited above.

Scheme 5

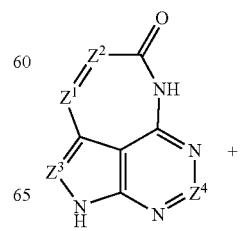

-continued

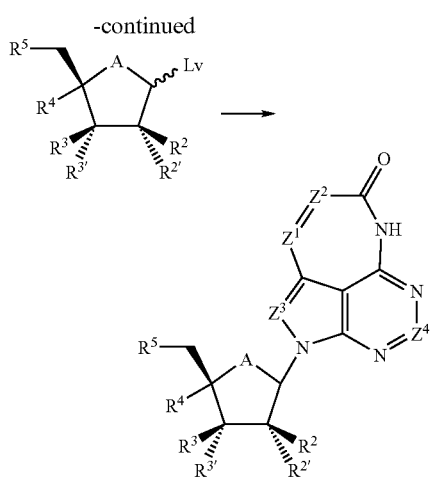

In Scheme 5, preferably A is O, $CH_2$ or optionally protected N; $Z^1$ and $Z^2$ are each independently CH, C-halogen, C-alkyl, C-aryl, C—O-alkyl or C—S-alkyl; $Z^3$ is CH, C-alkyl, C-halogen; N, CNHR, $CNH_2$, $CNR_2$, C=O, or C=S; $Z^4$ is CH, C-halogen, C-alkyl, C-aryl, C—O-alkyl, C—S-alkyl, C—OH, C—$NH_2$, C—NHR or C—$NR_2$; $R^2$, $R^{2'}$, $R^3$, $R^{3'}$, $R^4$ are each independently H, halogen, alkyl, O-alkyl, OH, optionally protected O, methyl, or F; $R^5$ is an optionally protected OH or $NH_2$; Lv is Leaving group.

Certain gycosyl benzo[cd]azulene-7-ones can be modified by well known functional group interconversions (FGIs). For example, the 8,9-double bond can be manipulated by hydrogenation, addition or addition-elimination processes. The 7-carbonyl function can also be converted into a 7-thiocarbonyl or undergo O-alkylation.

Scheme 6

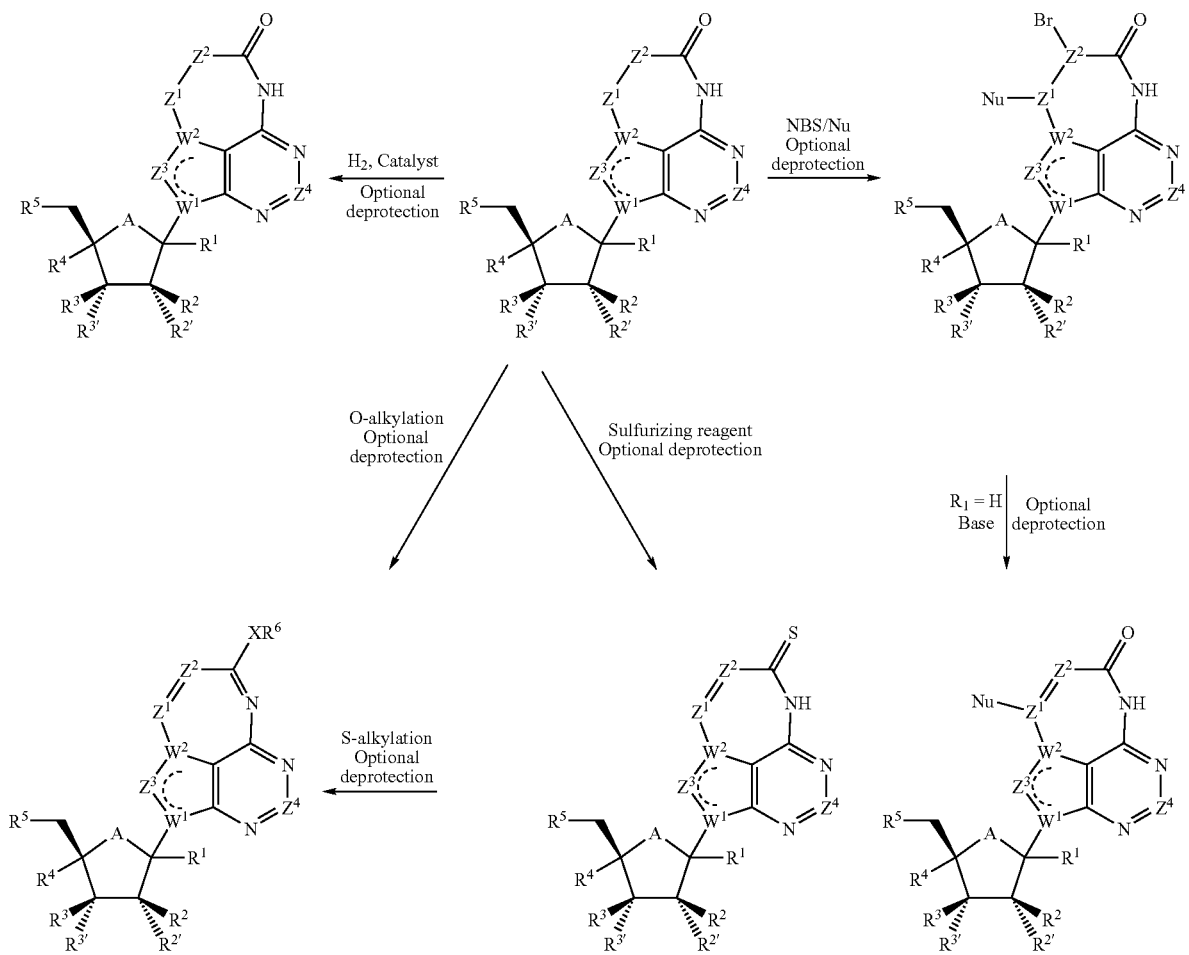

When equipped with an appropriate leaving group such as a chlorine atom that the 4-position of the gycosyl benzo[cd] azulene framework, a range of nucleophiles can engage in nucleophilic substitutions at this position. Suitable nucleophiles include alcohols, alkyl thiols and alkylamines.

In Scheme 6, preferably A is O, $CH_2$ or optionally protected N; Nu is nucleophile such as optionally protected N, O, or S; $W^1$ is C (if p bond) or N (if no p bond); $W^2$ is C, CH or N; $Z^1$ and $Z^2$ are each independently CH, C-halogen, C-alkyl, C-aryl, C—O-alkyl, or C—S-alkyl; $Z^3$ is CH, C-alkyl, C-halogen, N, CNHR, $CNH_2$, $CNR_2$, C=O, or C=S; $Z^4$ is CH or C-halogen, C-alkyl, C-aryl, C—O-alkyl, C—S-alkyl, C—OH, C—$NH_2$, C—NHR or C—$NR_2$; $R^1$, $R^2$, $R^{2'}$, $R^3$, $R^{3'}$, $R^4$ are each independently H, halogen, alkyl, O-alkyl, OH, optionally protected O, methyl, or F; $R^5$ is an optionally protected OH or $NH_2$; X is O or S; $R^6$ is alkyl, aryl, alkenyl or alkynyl.

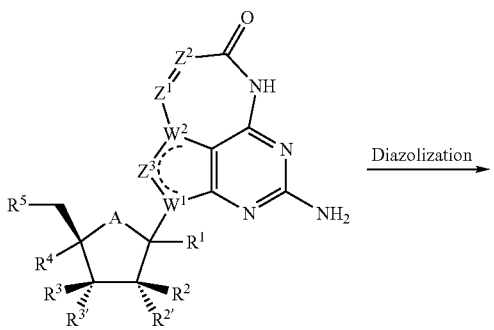

Scheme 8

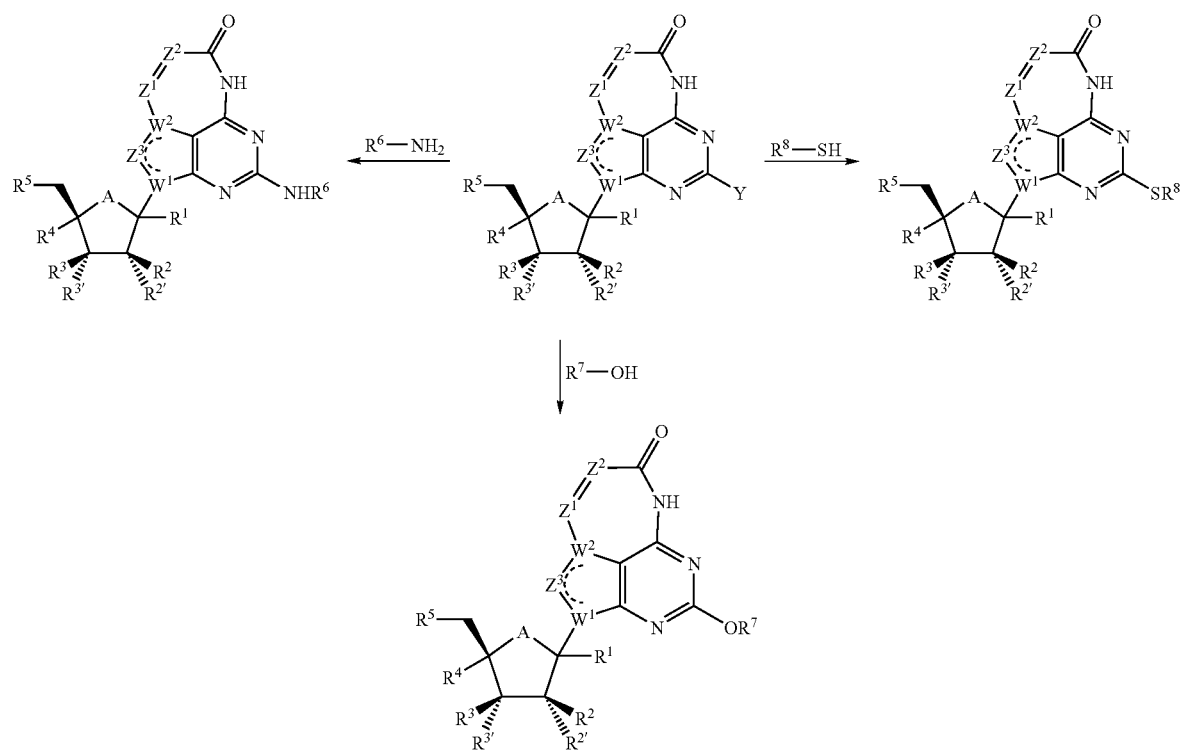

Scheme 7

When equipped with a 4-amino group the gycosyl benzo[cd]azulene framework can be modified by interception of a derived diazonium ion using standard techniques.

In Scheme 7, preferably A is O, $CH_2$ or optionally protected N; $W^1$ is C (if π bond) or N (if no π bond); $W^2$ is C, CH, or N; $Z^1$ and $Z^2$ are each independently CH, C-halogen, C-alkyl, C-aryl, C—O-alkyl or C—S-alkyl; $Z^3$ is CH, C-alkyl, C-halogen, N, CNHR, $CNH_2$, $CNR_2$, C=O, or C=S; Y is halogen; $R^1$, $R^2$, $R^{2'}$, $R^3$, $R^{3'}$, $R^4$ are each independently H, halogen, alkyl, O-alkyl, OH, optionally protected O, methyl, or F; $R^5$ is OH, $NH_2$ or optional protecting group; $R^6$, $R^7$, and $R^8$ are each independently alkyl, aryl, alkenyl or alkynyl.

-continued

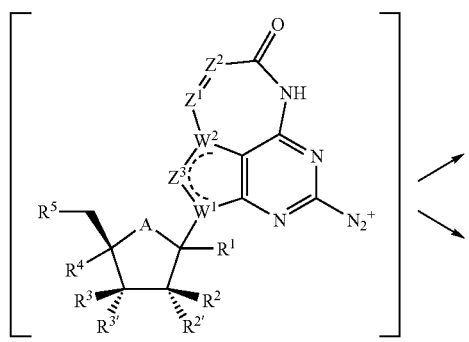

-continued

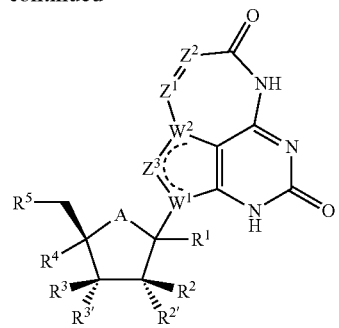

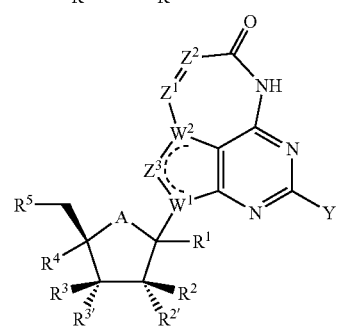

In Scheme 8, preferably A is O, CH$_2$ or optionally protected N; W$^1$ is C (if π bond) or N (if no π bond); W$^2$ is C, CH or N; Z$^1$ and Z$^2$ are each independently CH, C-halogen, C-alkyl, C-aryl, C—O-alkyl or C—S-alkyl; Z$^3$ is CH, C-allyl, C-halogen, N, CNHR, CNH$_2$, CNR$_2$, C=O, or C=S; Y is halogen; R$^1$, R$^2$, R$^{2'}$, R$^3$, R$^{3'}$, R$^4$ are each independently H, halogen, alkyl, O-alkyl, OH, optionally protected O, methyl, or F; R$^5$ is optionally protected OH or NH$_2$.

The compounds described here can be converted into their corresponding mono-, di- and triphosphates using well established methods. Furthermore, prodrugs of mono-, di- and triphosphates can be prepared in order to optimise the biological efficacy of these phosphorylated compounds. Methods for preparing such prodrugs are well known in the art (see Wagner, C. R., et al. *Med. Res. Rev.*, 2000, 20, 417-451).

In Scheme 9, preferably A is O, CH$_2$ or optionally protected N; R$^1$, R$^2$, R$^{2'}$, R$^3$, R$^{3'}$, R$^4$ are each independently H, halogen, alkyl, O-alkyl, OH, optionally protected O, methyl or F, Base is as described herein.

An alternative to the use of phosphates and prodrugs of these is the use of phosphate mimics and their prodrugs (for prodrugs, see Wagner, C. R., et al. *Med. Res. Rev.*, 2000, 20, 417-451). One such phosphate mimic is shown below and this can be prepared using appropriately protected nucleosides and known conditions.

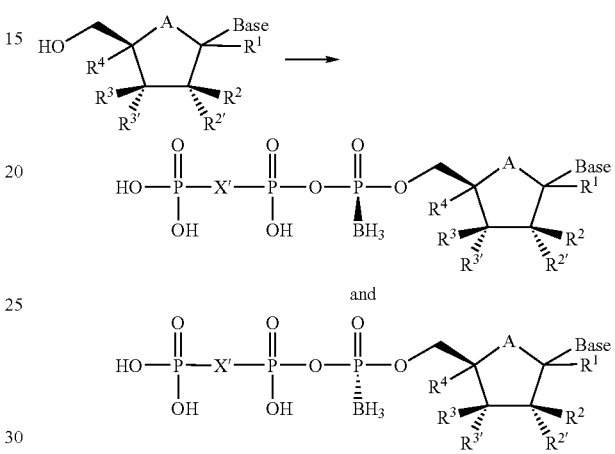

Scheme 10

Methods of preparing tri-, di, and mono-phosphate mimics useful for making compounds of the invention is found in WO 2003/072757 and WO 2003/073989 filed Feb. 28, 2003. A representative scheme is described above.

In Scheme 10, preferably A is O, CH$_2$ or optionally protected N; R$^1$, R$^2$, R$^{2'}$, R$^3$, R$^{3'}$, R$^4$ are each independently H, halogen, alkyl, O-alkyl, OH, optionally protected O, methyl or F; X' is O, S, NH, CF$_2$, CHF, CClH, CBr$_2$ or CHBr; Base is as described herein.

Biological Assays

Antiviral assays are conducted according to published, widely used protocols. In order to obtain the therapeutic index, compound-induced cytotoxicity to host cells is also measured in parallel with antiviral activities. To determine the mode of action of antiviral nucleosides the correspond-

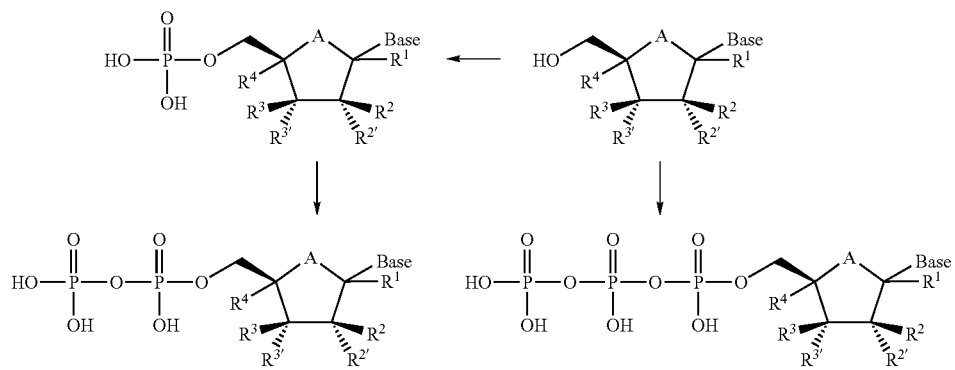

Scheme 9 ing nucleoside triphosphates are subject to enzyme-based assays for the inhibition of viral polymerases according to known protocols (Ranjith-Kumar et al. *J. Virol.* 2001, 75, 8615; Dhanak et al. *J. Biol. Chem.* 2002, 277, 38322-38327). Some compounds of the present invention showed $K_i$ values of less than 1 µM against HCV NS5B.

Since the replicon RNA replication mimics the replication of HCV RNA in infected hepatocytes, compounds that have the inhibitory effects in replicon assays are potentially useful as anti-HCV drugs. The HCV replicon-containing cell lines (Randall and Rice, *Current Opinion in Infectious Diseases* 2001, 14, 743) are used for the identification of potential anti-HCV compounds. Among them is a widely used subgenomic replicon system developed by Lohmann et al. (*Science* 1999, 285, 110; *J. General Virol.* 2000, 81, 1631; *J. Virol.* 2001, 75, 1437, 2002, 76, 4008). Some compounds of the present invention showed potent anti-HCV activity with $EC_{50}$ values of low µM.

Widely used protocols developed by Korba et al. (*Antiviral Res.* 1992, 19, 55), and Pai et al. (*Antimicrobial Agents Chemother.* 1996, 40, 380) are useful for the determination of in vitro anti-HBV activity.

Anti-HIV assays can be conducted according to the protocols developed by Schinazi et al. (*Antimicrobial Agents Chemother.* 1990, 34, 1061; 1992, 36, 2423; 1993, 37, 875) or other widely used protocols (Kimpton et al. *J. Virol.* 1992, 66, 2232; Chan et al. *J. Med. Chem.* 2001, 44, 1866).

Biological Applications and Administration

The nucleosides, nucleotide mimics and/or their prodrugs of the present invention may be useful for the inhibition of a variety of enzymes including, but not limited to, DNA or RNA polymerases, helicases, ribonucleotide reductases, protein kinases, and telomerases and for the modulation of G-proteins, P2 purinergic receptors and the allosteric sites of a variety of enzymes.

The nucleosides, nucleotide mimics and/or their prodrugs of the present invention are useful as human therapeutics for the treatment of infectious diseases caused by viruses including, but not limited to, HIV, HBV, HCV, HDV, HSV, HCMV, small pox, West Nile virus, SARS virus, influenza viruses, measles, rhinovirus, RSV, VZV, EBV, vaccinia virus, and papilloma virus.

The nucleosides, nucleotide mimics and/or their prodrugs of the present invention are useful for the treatment of infectious diseases caused by infectious agents such as parasites, bacteria and fungi.

Those nucleosides, nucleotide mimics and/or their prodrugs that have potent cytotoxicities to fast-dividing cancerous cells are useful for the treatment of proliferative disorders, including, but not limited to, lung cancer, liver cancer, prostate cancer, colon cancer, breast cancer, ovarian cancer, melanoma, and leukemia.

As the ligands of P2 receptors and G-proteins as well as the inhibitors of protein kinases, the nucleosides, nucleotide mimics and/or their prodrugs of the present invention are useful for the treatment of a wide range of other diseases and disorders such as inflammatory diseases, autoimmune diseases, Type 2 diabetes, and cardiovascular diseases.

In order to overcome drug resistance, combination therapies are widely used in the treatment of infectious diseases and proliferative disorders. The nucleosides, nucleotide mimics and/or their prodrugs of the present invention may be therapeutically administered as a single drug, or alternatively may be administered in combination with one or more other active chemical entities to form a combination therapy. The other active chemical entities may be a small molecule, a polypeptide, or a polynucleotide.

The pharmaceutical composition of the present invention comprises at least one of the compounds represented by the formulas herein or pharmaceutically acceptable salts, esters or prodrugs thereof as active ingredients. The compositions include those suitable for oral, topical, intravenous, subcutaneous, nasal, ocular, pulmonary, and rectal administration. The compounds of the invention can be administered to mammalian individuals, including humans, as therapeutic agents.

Accordingly, the compounds of the invention are useful as anti-microbial infection agents. The present invention provides a method for the treatment of a patient afflicted with an infection comprising administering to the patient a therapeutically effective anti-microbial amount of a compound of the invention. The term "microbe infection" as used herein refers to an abnormal state or condition characterized by microbial transformation of cells, microbial replication and/or microbial proliferation. Microbial infections for which treatment with a compound of the invention will be particularly useful include the microbes mentioned above.

The term "treat" as in "to treat a disease" is intended to include any means of treating a disease in a mammal, including (1) preventing the disease, i.e., avoiding any clinical symptoms of the disease, (2) inhibiting the disease, that is, arresting the development or progression of clinical symptoms, and/or (3) relieving the disease, i.e., causing regression of clinical symptoms.

For example, the compounds of the invention are useful as antiviral agents. The present invention provides a method for the treatment of a patient afflicted with a viral infection comprising administering to the patient a therapeutically effective antiviral amount of a compound of the invention. The term "viral infection" as used herein refers to an abnormal state or condition characterized by viral transformation of cells, viral replication and proliferation. Viral infections for which treatment with a compound of the invention will be particularly useful include the viruses mentioned above.

A "therapeutically effective amount" of a compound of the invention refers to an amount which is effective, upon single or multiple dose administration to the patient, in controlling the growth of e.g., the microbe or tumor or in prolonging the survivability of the patient beyond that expected in the absence of such treatment. As used herein, "controlling the growth" refers to slowing, interrupting, arresting or stopping the microbial or proliferative transformation of cells or the replication and proliferation of the microbe and does not necessarily indicate a total elimination of e.g., the microbe or tumor.

Accordingly, the present invention includes pharmaceutical compositions comprising, as an active ingredient, at least one of the compounds of the invention in association with a pharmaceutical carrier. The compounds of this invention can be administered by oral, parenteral (intramuscular, intraperitoneal, intravenous (IV) or subcutaneous injection), topical, transdermal (either passively or using iontophoresis or electroporation), transmucosal (e.g., nasal, vaginal, rectal, or sublingual) or pulmonary (e.g., via dry powder inhalation) routes of administration or using bioerodible inserts and can be formulated in dosage forms appropriate for each route of administration.

Solid dosage forms for bral administration include capsules, tablets, pills, powders, and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating, agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

Topical formulations will generally comprise ointments, creams, lotions, gels or solutions. Ointments will contain a conventional ointment base selected from the four recognized classes: oleaginous bases; emulsifiable bases; emulsion bases; and water-soluble bases. Lotions are preparations to be applied to the skin or mucosal surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Creams, as known in the art, are viscous liquid or semisolid emulsions, either oil-in-water or water-in-oil. Topical formulations may also be in the form of a gel, i.e., a semisolid, suspension-type system, or in the form of a solution.

Finally, formulations of these drugs in dry powder form for delivery by a dry powder inhaler offer yet another means of administration. This overcomes many of the disadvantages of the oral and intravenous routes.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment desired. Generally, dosage levels of between 0.001 to 10 mg/kg of body weight daily are administered to mammals.

The following examples are put forth so as to provide those of ordinary skill in the art with a complete disclosure and description of how to prepare and use the compounds disclosed and claimed herein.

In order to overcome drug resistance, combination therapies are widely used in the treatment of viral infections. The nucleoside analogs, corresponding 5'-monophosphate, 5'-diphosphate, 5'-triphosphate, and prodrugs thereof of the present invention may be therapeutically administered as a single drug, or alternatively they may be administered in combination with one or more other active chemical entities to form a combination therapy. The other active chemical entities may be a small molecule, a polypeptide, or a polynucleotide.

All references mentioned herein are incorporated herein by reference in their entirety.

The following Examples are offered to illustrate but not to limit the invention.

EXAMPLES

Example 1

2-(2-C-methyl-β-D-ribofuranosyl)-2,6-dihydro-7H-1,2,3,5,6-pentaazabenzo[cd]azulene-7-one (1.7)

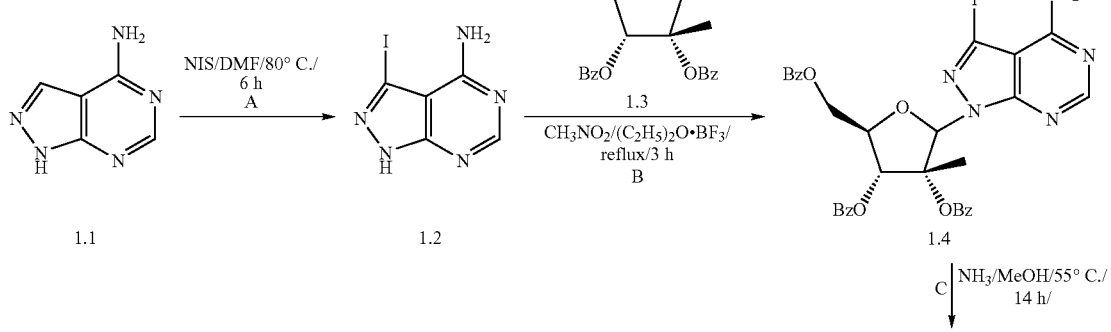

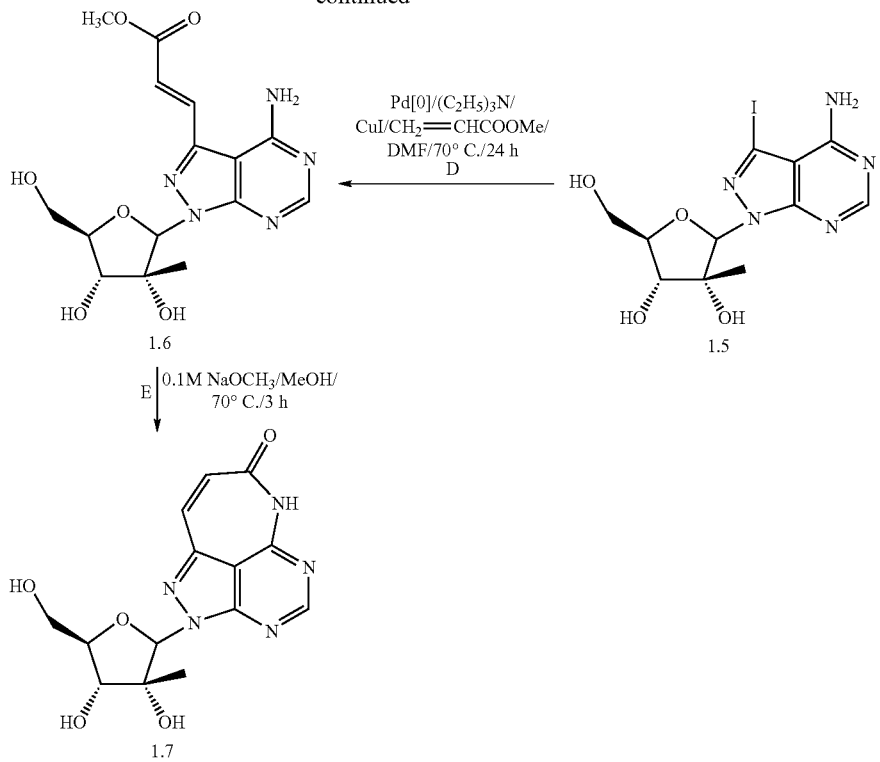

For the preparation of tricyclic nucleoside 1.7, 4-amino-3-iodo-1H-pyrazolo[3,4-d]pyrimidine 1.2 was prepared by the iodination of 4-amino-1H-pyrazolo[3,4-d]pyrimidine 1.1 using N-iodosuccinimide in DMF at 80° C. The glycosylation of 1.2 with commercially available 2-C-methyl-tetrabenzoyl ribofuranose 1.3 in boiling nitromethane in the presence of boron trifluoride etherate gave 2'C-methyl nucleoside 1.4 in 65% yield after purification. Removal of ester blocking groups with ammonia in MeOH provided the free nucleoside 1.5 in 83% isolated yield. The use of methyl acrylate in the Pd[0] catalyzed cross coupling reaction of 1.5 afforded the 7-alkenyl nucleoside 1.6. The treatment of compound 1.6 with NaOMe/MeOH resulted in an intramolecular cyclization, yielding the target tricyclic nucleoside 1.7.

Example 1

Step-A:
4-Amino-3-iodo-1H-pyrazolo[3,4-d]pyrimidine (1.2)

4-Amino-1H-pyrazolo[3,4-d]pyrimidine was prepared according to the published method (*J. Med. Chem.* 1993, 36, 3424-3430).

Example 1

Step-B: 4-Amino-3-iodo-1-(2-C-methyl-2,3,5-tri-O-benzoyl-β-D-ribofuranosyl)pyrazolo[3,4-d]pyrimidine (1.4)

1-O-Acetyl-2-C-methyl-2,3,5-tri-O-benzoyl-D-ribofuranose (1.0 g, 1.72 mmol) was dissolved in anhydrous nitromethane (10.0 mL) and to this solution compound 1.2 (312 mg, 1.21 mmol) was added. The resulting suspension was brought to reflux and borontrifluoride etherate (0.23 mL, 1.78 mmol) was added. The suspension became a clear solution, which was heated at reflux for 2 hr. The mixture was cooled, the solvents were evaporated and the off-white foamy residue was dissolved in ethyl acetate and then poured with stirring into aq. sat. NaHCO$_3$. The aqueous layer was extracted twice with ethyl acetate and the combined organic layers were dried (Na$_2$SO$_4$), filtered and evaporated to give an off-white solid. This material was purified by flash column chromatography on silica gel using CH$_2$Cl$_2$ to 2-3% MeOH in dichoromethane as eluent to give the desired compound 1.4 (811 mg) as a yellow foam.

Example 1

Step-C: 4-Amino-3-iodo-1-(2-C-methyl-β-D-ribofuranosyl)-1H-pyrazolo[3,4-d]pyrimidine (1.5)

A solution of compound 1.4 (540 mg, 0.75 mmol) in MeOHic NH$_3$ (120 mL, saturated at 0° C.) was stirred in a bomb at 45° C. for 16 hr. The mixture was evaporated to dryness and then the residue co-evaporated with additional MeOH. Purification by silica gel column chromatography using 6-14% MeOH in dichoromethane as eluent gave the desired compound 1.5 (244 mg) as an off-white solid.

Example 1

Step-D: 4-Amino-1-(2-C-methyl-β-D-ribofuranosyl)-3-[2-methoxycarbonyl)ethenyl]-1H-pyrazolo[3,4-d]pyrimidine (1.6)

To a solution of compound 1.5 from Step-C (392 mg, 0.54 mmol) in DMF (10 mL) was added CuI (44 mg, 0.23 mmol), methyl acrylate (2.0 mL, 23.23 mmol), triethylamine (0.332 mL, 2.36 mmol) and tetrakis(triphenylphosphine)palladium [0] (133 mg, 0.12 mmol), heated at 70° C. under Ar. The reaction mixture was heated at 70° C. for 36 hr. After this time, further CuI (44 mg, 0.23 mmol), methyl acrylate (2.0 mL, 23.23 mmol), triethylamine (0.332 mL, 2.36 mmol) and tetrakis(triphenylphosphine)palladium [0] (133 mg, 0.12 mmol) were added and the mixture was heated at 70° C. for a further 6 hr. Then the reaction mixture was cooled to room temperature and 8 mL of 1/1 MeOH/CH$_2$Cl$_2$ was added. 100 mg of Dowex 1×2-100 Bicarb form was added, the suspension stirred at room temperature for 45 min then filtered. The resin was washed with 5×10 mL MeOH/CH$_2$Cl$_2$: 1/1, the solvents were evaporated and the residual DMF was finally evaporated by azeotropic evaporation with toluene (2×10 mL). The residue was redissolved in MeOH and pre-adsorbed on silica gel. Chromatographic purification on silica gel using 4-4.5% MeOH in CH$_2$Cl$_2$ as eluent gave desired ester 1.6 (216 mg, yield 52%).

Example 1

Step-E: 2-(2-C-methyl-β-D-ribofuranosyl)-2,6-dihydro-7H-1,2,3,5,6-pentaazabenzo[cd]azulene-7-one (1.7)

A solution of ester 1.6 (208.3 mg, 0.57 mmol) in 0.1M NaOCH$_3$ in MeOH was heated at reflux for 3 h, cooled to 0° C. and Dowex 50×100 (acidic form) was added until the solution pH became neutral. The reaction mixture was filtered and the resin was washed with MeOH. The solvent was evaporated, and the residue was purified using silica gel column chromatography using 4 to 4.5% MeOH in CH$_2$Cl$_2$ as eluent to give the desired compound 1.7 (26.5 mg) as an off-white solid.

$^1$H NMR (DMSO-d$_6$) d 11.6 (s, NH, 1H), 8.56 (s, H-4, 1H), 7.31 (d, J 12 Hz, CH, 1H), 6.28 (d, J 12 Hz, CH, 1H), 6.15 (s, H-1', 1H), 5.28 (s, 2'-OH, 1H), 5.14 (d, J 6.9 Hz, 3'-OH, 1H), 4.65 (t, J 5.7 Hz, 5'-OH, 1H), 3.95-4.09 (m, H-3', H-4', 2H), 3.62-3.69 (m, H-5', 2H), 0.83 (s, CH$_3$, 3H). MS m/z 332 (M-H)$^+$.

Example 2

2-(2-C-methyl-β-D-ribofuranosyl)-2,6,8,9-tetrahydro-7-oxa-2,3,5,6-tetraazabenzo[cd]azulene (2.9)

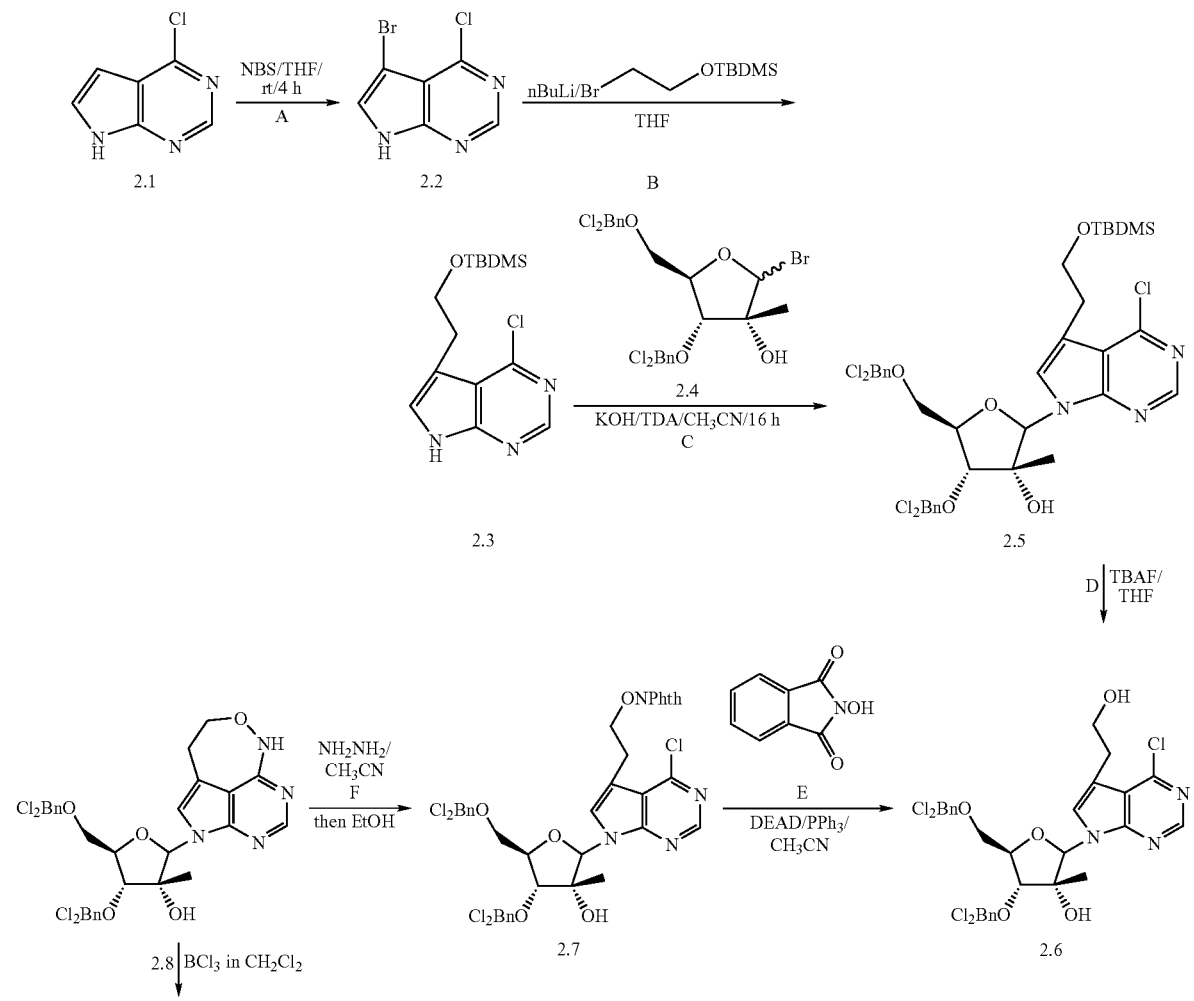

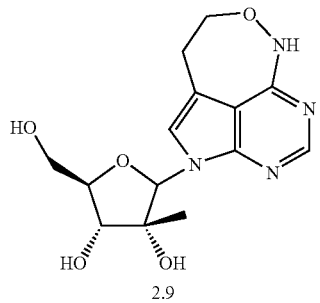

2.9

Bromination (NBS/THF) of starting pyrrolo pyrimidine 2.1 afforded bromopyrrolo pyrimidine 2.2 in 63% yield. Treatment of 2.2 with n-butyillithum in THF at −78° C. resulted in a selective lithio-bromo exchange to yield an intermediate which on treatment with (2-bromoethoxy) tert-butyldimethylsilane (−30° C./5 h) delivered pyrimidine 2.3 in 43% yield along with recovered starting pyrimidine 2.2 (30%). When the reaction was repeated on large scale (7.0 g of 2.2), significant improvement was achieved (−20° C./16 h) and pyrimidine 2.3 was isolated in 55% yield (5.5 g). Stereoselective glycosylation of 2.3 with bromo sugar 2.4 (freshly prepared form commercially available 3,5-bis-O-(2,4-dichlorophenylmethyl)-2-C-methyl-1-O-methyl-α-D-ribofuranose using HBr in acetic acid/$CH_2Cl_2$) with 85% KOH/TDA-1 (tris[2-(2-methoxyethoxy)ethyl]amine afforded nucleoside 2.5 in 26% isolated yield. Removal of the TBDMS group of 2.5 with tetrabutylammonium fluoride/THF gave diol 2.6. Compound 2.6 underwent Mitsunobu coupling with N-hydroxyphthalimide to give the corresponding phthalimidooxyethyl nucleoside 2.7 in 88% yield. 2.7 was treated with anhydrous $H_2NNH_2$ to remove the phthaloyl group and this free amino oxy intermediate (crude) 2.8 was heated in EtOH to give 2.8. Removal of the dichlorobenzyl groups of 2.8 by using $BCl_3$ in $CH_2Cl_2$ delivered tricyclic nucleoside 2.9.

Example 2

Step-A: 5-Bromo-4-chloropyrrolo[2,3-d]pyrimidine (2.2)

To solution of 4-chloro-7H-pyrrolo[2,3-d]pyrimidine was prepared according to a literature procedure (Townsend, L. B. et al., *J. Med. Chem.* 1988, 31, 2086-2092).

Example 2

Step-B: 5-[2-(tert-Butyldimethylsiloxy)ethyl]-4-chloro-7H-pyrrolo[2,3-d]pyrimidine (2.3)

A suspension of compound 2.2 from Step A (2.0 g, 8.6 mmol) in THF (40.0 mL) was cooled to −78° C. under an argon atmosphere. n-BuLi (1.6M in hexanes, 13.4 mmol) was then added over 1.0 hr via syringe. A suspension formed and (2-bromoethoxy)-tert-butyldimethylsilane (7.4 mL, 34.4 mmol) was added via syringe while maintaining the reaction mixture at −78° C. The reaction mixture was allowed to slowly reach −30° C. and stirred for 2 h, then −30 to −10° C. for 1 h, and −10 to 0° C. for 1 hr. The reaction mixture became dark brown in color, was treated with $NH_4Cl$, $CH_2Cl_2$ and water. The reaction mixture was extracted with $CH_2Cl_2$ and the extracts were dried over $Na_2SO_4$, filtered and evaporated. The beige residue was purified by flash column chromatography using 23% EtOAc in hexanes as eluent to give the desired compound 2.3 (1.16 g, 43%) as a white solid. (Brown, D. M. et al., *J. Chem. Soc. PT*-1, 3565-3570.)

Example 2

Step-C: 5-[2-(tert-Butyldimethylsiloxy)ethyl]-4-chloro-7-[2-C-methyl-3,5-bis-O-(2,4-dichlorophenylmethyl)-β-D-ribofuranosyl]-7H-pyrrolo[2,3-d]pyrimidine (2.5)

Compound 2.3 (2.5 g, 8.00 mmol) was suspended in $CH_3CN$ (50 mL), and powdered 85% KOH, (1.3 g, 19.73 mmol) followed by TDA-1 (tris[2-(2-methoxyethoxy)ethyl]amine) (0.2 mL, 0.62 mmol) were added. After stirring at room temperature for 10 min, a freshly prepared solution of bromo sugar 2.4 (prepared from commercially available 3,5-bis-O-(2,4-dichlorophenylmethyl)-2-C-methyl-1-O-methyl-α-D-ribofuranose; (i) *Helv. Chim. Acta*, 1995, 78, 486; (ii) WO 02/057287, 2002) (10.1 mmol) in anhydrous acetonitrile (50 mL) was added via cannula, and the reaction stirred for 24 hr at room temperature then cooled in an ice/water bath and treated with $CH_2Cl_2$ (100 mL) and water (80 mL). The aqueous material was extracted three times with $CH_2Cl_2$, the combined organic layers were dried over $Na_2SO_4$, filtered and evaporated The crude product was purified on a silica gel column using 20% ethyl acetate/hexanes as eluent to give the desired nucleoside 2.5 (1.03 g, 13%). Further elution with 25% EtOAc/hexanes as eluent gave a mixture of the desired nucleoside 2.5 and starting base 2.3 (350 mg).

Example 2

Step-D: 4-Chloro-7-[2-C-methyl-3,5-bis-O-(2,4-dichlorophenylmethyl)-β-D-ribofuranosyl]-5-(2-hydroxyethyl)-7H-pyrrolo[2,3-d]pyrimidine (2.6)

To a solution of compound 2.5 (1.14 g, 1.47 mmol) in THF (30 mL) was added a 1.0M solution of tetrabutylammonium fluoride in THF (2.2 mmol) at room temperature. The colorless solution was stirred for 5 hr at room temperature and then diluted by addition of 10 mL of CH$_2$Cl$_2$ and 10 mL of brine. The aqueous layer was extracted three times with CH$_2$Cl$_2$, dried over Na$_2$SO$_4$, filtered and evaporated. The residue obtained was purified by silica gel column chromatography using 1-1.5% MeOH in CH$_2$Cl$_2$ as eluent to give the desired compound 2.6 (900 mg, 88%) as a white solid.

Example 2

Step-E: 4-Chloro-7-[2-C-methyl-3,5-bis-O-(2,4-dichlorophenylmethyl)-β-D-ribofuranosyl]-5-(2-phthalimidooxyethyl)-7H-pyrrolo[2,3-d]pyrimidine (2.7)

To a solution of the compound 2.6 (359.0 mg, 0.54 mmol) in THF (10 mL) were added triphenylphosphine (215.0 mg, 0.82 mmol) and N-hydroxyphthalimide (132.0 mg, 0.0.81 mmol) followed by diethylazodicarboxylate (DEAD) (153 μL, 0.88 mmol), and the solution was stirred overnight at room temperature. The reaction mixture was diluted by adding 10 mL of CH$_2$Cl$_2$ and 10 mL of water. The aqueous layer was extracted three times with CH$_2$Cl$_2$, dried over Na$_2$SO$_4$, filtered and evaporated. The product was purified by flash column chromatography using 15-20% EtOAc in hexanes as eluent gave the desired compound 2.7 (369 mg, 85%) as a white solid.

Example 2

Step-F: 2-(2-C-methyl-3,5-bis-O-(2,4-dichlorophenylmethyl)-β-D-ribofuranosyl)-2,6,8,9-tetrahydro-7-oxa-2,3,5,6-tetraazabenzo[cd]azulene (2.8)

To a suspension of compound 2.7 (880.0 mg, 1.09 mmol) in acetonitrile (60 mL) was added anhydrous hydrazine (38 μl, 1.19 mmol), and the solution was stirred for 2 hr at room temperature. No starting material left as judged by the tlc. The white precipitate (phthalic hydrazide) was filtered off and washed with anhydrous acetonitrile, and then solution was evaporated to dryness. The crude reaction product was dried under high vacuum to give 864 mg of a white solid. The resulting free aminooxy intermediate was redissolved in anhydrous EtOH (50 mL) and the solution was heated at reflux for 2 d. After evaporation, reaction mixture was purified by silicagel column chromatography using CH$_2$Cl$_2$ to 2% MeOH in CH$_2$Cl$_2$ to give desired compound 2.8 (466 mg) as a white foam.

Example 2

Step-G: 2-(2-C-methyl-β-D-ribofuranosyl)-2,6,8,9-tetrahydro-7-oxa-2,3,5,6-tetraazabenzo[cd]azulene (2.9)

To a solution of compound 2.8 (128.0 mg, 0.20 mmol) in CH$_2$Cl$_2$ (25 mL) at −78° C., was added a 1.0M solution of BCl$_3$ in CH$_2$Cl$_2$ (2.0 mL, 2.0 mmol) dropwise via syringe. The mixture was stirred at −78° C. for 1.5 h, then at −35° C. to −40° C. for 2.5 hr. The reaction was quenched with MeOH (8.0 ml) and the solvents were evaporated. The resulting crude product was purified by flash column chromatography over silica gel using 5% MeOH in CH$_2$Cl$_2$ as eluent to give the title compound 2.9 (59.2 mg) as a white foam.

$^1$H NMR (DMSO-d$_6$) d 10.62 (s, NH, 1H), 8.19 (s, H-2, 1H), 7.47 (s, H-6, 1H), 6.15 (s, H-1', 1H), 5.09 (br s, 2'-OH, 3'-OH, 5'-OH, 3H), 4.29 (br s, OCH$_2$CH$_2$, 2H), 3.63-3.96 (m, H-3', H-4', H5', 4H), 2.91-2.96 (m, OCH$_2$CH$_2$, 2H), 0.70 (s, CH$_3$, 3H). MS m/z 381 (M+CH$_3$COO)$^-$.

Example 3

2-(β-D-ribofuranosyl)-2,6-dihydro-7H-1,2,3,5,6-pentaazabenzo[cd]azulene-7-one (3.3)

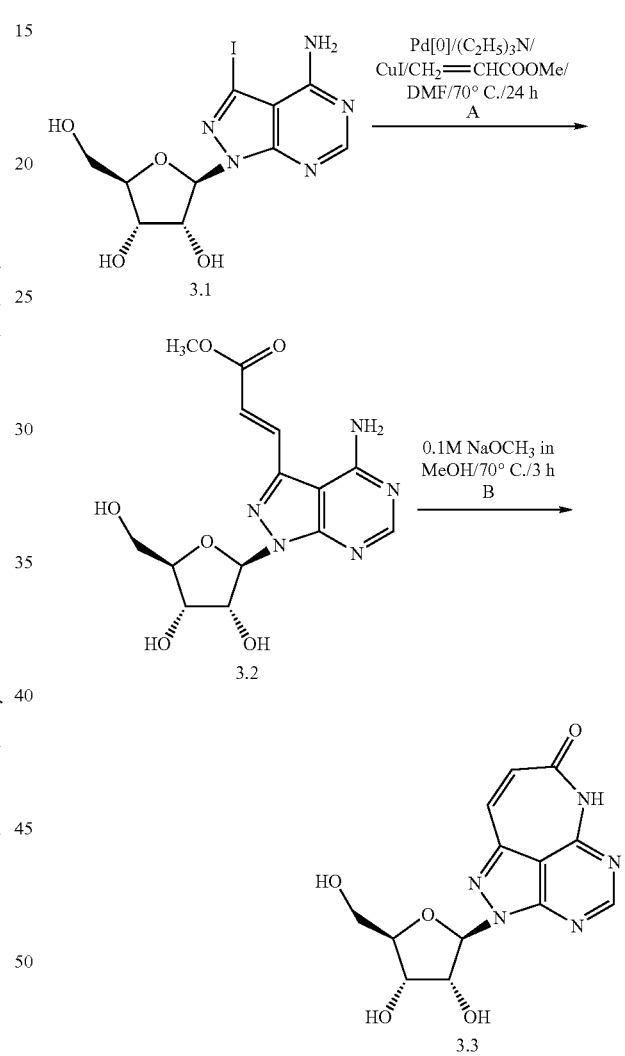

Example 3

Step-A: 4-Amino-1-(β-D-ribofuranosyl)-3-[2-methoxycarbonyl)ethenyl]-1H-pyrazolo[3,4-d]pyrimidine (3.2)

To a solution of compound 3.1* (300 mg, 0.76 mmol) in DMF (10 mL) was added CuI (29 mg, 0.15 mmol), methylacrylate (1.3 mL, 15.1 mmol), triethylamine (1.3 mL, 3.09 mmol) and tetrakis(triphenylphosphine)palladium[0] (88 mg, 0.08 mmol) and the mixture heated at 70° C. for 36 hr under argon. After this time, additional CuI, methylacrylate, triethylamine and Pd catalyst were added, and the dark brown reaction mixture was heated for a further 6 hr. Then the reaction mixture was cooled to room temperature and 8 mL of 1/1 MeOH/CH$_2$Cl$_2$ was added. 100 mg Dowex 1×2-100 Bicarb form, was added and the mixture stirred for 45 min at room temperature then filtered. The resin was washed with 2×10 mL MeOH/CH$_2$Cl$_2$:1/1 and the solvents evaporated. Chromatographic purification on silica gel using 6-7% MeOH in CH$_2$Cl$_2$ gave the desired compound 3.2 (120 mg) as a light yellow solid. *J. Med. Chem. 1993, 36, 3424-3430.

Example 3

Step-B: 2-(β-D-ribofuranosyl)-2,6-dihydro-7H-1,2,3,5,6-pentaazabenzo[cd]azulene-7-one (3.3)

A solution of compound 3.2 (110 mg, 0.31 mmol) in 0.1M NaOCH$_3$ in MeOH was heated at reflux for 3 h, cooled to 0° C. and treated with Dowex 50×100 (acidic form) until the pH of the mixture became neutral. The reaction contents were filtered and the resin was washed with MeOH/CH$_2$Cl$_2$ (1:1). The solvents were evaporated and the residue obtained was purified by flash column chromatography using 4-4.5% MeOH in CH$_2$Cl$_2$ as eluent to give the title compound 3.3 (10.7 mg) as a white solid. $^1$H NMR (DMSO-d$_6$) d 11.6 (s, NH, 1H), 8.58 (s, H-4, 1H), 7.35 (d, J 12 Hz, CH, 1H), 6.31 (d, J 12 Hz, CH, 1H), 6.11 (d, J 4.5 Hz, H-1', 1H), 5.46 (d, J 5.7 Hz, 2'-OH, 1H), 5.21 (d, J 3.9 Hz, 3'-OH, 1H), 4.80 (t, J 5.1 Hz, 5'-OH, 1H), 4.62-4.64 (m, H-2', 1H), 3.92-3.94 (m, H-3', 1H), 3.44-3.61 (m, H-4', H5', 2H), 0.83 (s, CH$_3$, 3H).

Example 4

2-(2-C-methyl-β-D-ribofuranosyl)-6,7,8,9-tetrahydro-2H-2,3,5,6-tetraazabenzo[cd]azulene (4.6)

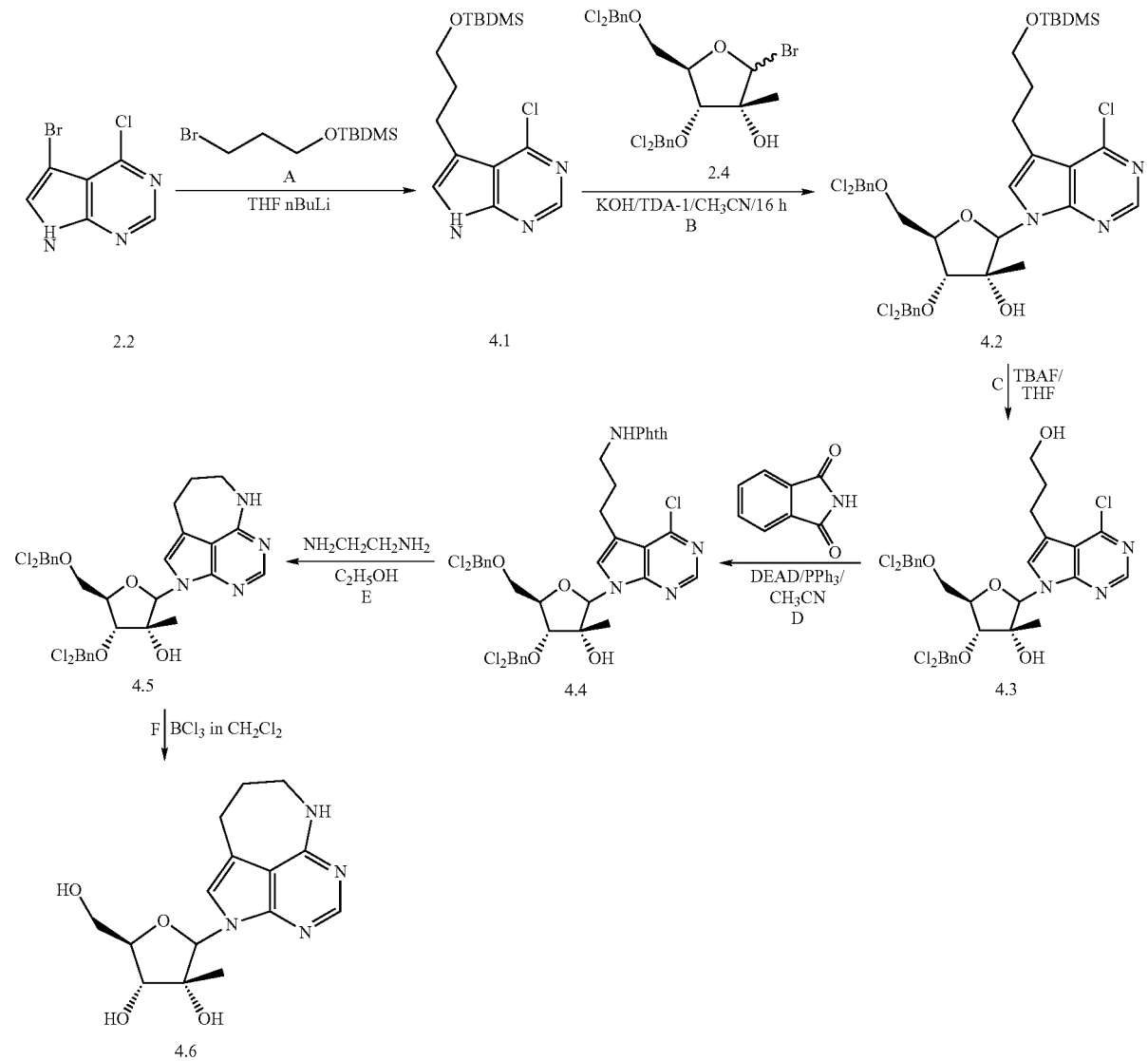

Treatment of 2.2 with n-butyllithium in THF at −78° C. resulted in a selective halogen-metal exchange to yield an intermediate which on treatment with (3-bromopropoxy) tert-butyldimethylsilane (−30° C./5 h) afforded pyrimidine 4.1 in 36% yield along with the recovery of starting pyrimidine (30%). When the reaction was repeated on large scale (starting 7.0 g of 2.2), significant improvement was achieved (−20° C./16 h) and pyrimidine 4.1 was isolated in 55% yield. Stereoselective glycosylation of 4.1 with bromo sugar 2.4 in the presence of KOH/TDA-1 afforded nucleoside 4.2 in 17% isolated yield. Removal of the TBDMS protecting group of 4.2 allowed Mitsunobu coupling with phthalimide to give the corresponding phthalimido derivative 4.4 in quantitative yield. Phthalimide cleavage using hydrazine in different solvents failed to produce primary amine and it was found that an alternative reaction condition using ethylenediamine/ethanol resulted in phthalimide cleavage followed by in situ cyclization of the free amino intermediate to give protected tricyclic 4.5 in 56% yield. Deprotection of the dichlorobenzyl groups of 4.5 using $BCl_3$ in $CH_2Cl_2$/−78° C. to −30° C. delivered the target tricyclic nucleoside 4.6 in 84% isolated yield after purification by silica gel column chromatography.

Example 4

Step-A: 5-[2-(tert-Butyldimethylsiloxy)propyl]-4-chloro-7H-pyrrolo[2,3-d]pyrimidine (4.1)

A suspension of compound 2.2 (10.0 g, 43.0 mmol) in THF (140.0 mL) was cooled to −78° C. under an argon atmosphere and n-BuLi (1.6M in hexanes, 67.3 mmol) was then added via syringe over 1.5 hr. The resulting suspension was stirred for the next 30 min at −78° C. then (3-bromopropoxy)-tert-butyldimethylsilane (21.4 mL, 172.0 mmol) was slowly added via syringe at −78° C. over 1 hr. The reaction mixture was allowed to slowly reach −30° C. and stirred for the next 2 h, and −30 to 10° C. for 1 h, and −10 to 0° C. for 1 hr. The reaction mixture became dark brown in color, and was kept at 4° C. overnight. The reaction was quenched by adding aqueous $NH_4Cl$ (100 mL), and diluted with $CH_2Cl_2$ (600 mL) and water (120 mL) then extracted with $CH_2Cl_2$. The combined organic layers were dried over $Na_2SO_4$, filtered and evaporated. The beige colored residue was purified by flash column chromatography using 25% EtOAc in hexanes as eluent to give the desired compound 4.1 (5.5 g) as a white solid.

Example 4

Step-B: 5-[2-(tert-Butyldimethylsiloxy)propyl]-4-chloro-7-(2-C-methyl-3,5-bis-O-(2,4-dichlorophenylmethyl)-β-D-ribofuranosyl)-7H-pyrrolo[2,3-d]pyrimidine (4.2)

Compound 4.1 (5.24 g, 16.0 mmol) was suspended in $CH_3CN$ (120 mL) and powdered 85% KOH ((2.63 g, 40.0 mmol) was added followed by TDA-1 (tris[2-(2-methoxyethoxy)ethyl]amine (0.4 mL, 1.24 mmol). After stirring at room temperature for 30 min, a freshly prepared solution of bromo sugar 2.4 (20.0 mmol) in anhydrous acetonitrile (120 mL) was added via cannula, and the mixture stirred for 2 days at room temperature, cooled in an ice bath and treated with $CH_2Cl_2$ (200 mL) and water (100 mL). The aqueous material was extracted three times with $CH_2Cl_2$ and the combined organic extracts were dried over $Na_2SO_4$, filtered and evaporated. The crude product was purified on a silica gel column using 15% ethyl acetate/hexanes as eluent to give desired compound 4.2 (2.6 g) as a light yellow solid.

Example 4

Step-C: 4-Chloro-7-[2-C-methyl-3,5-bis-O-(2,4-dichlorophenylmethyl-β-D-ribofuranosyl]-5-(2-hydroxypropyl)-7H-pyrrolo[2,3-d]pyrimidine (4.3)

To a solution of compound 4.2 (800 mg, 1.01 mmol) in THF (20 mL) was added a 1.0 M solution of tetrabutylammonium fluoride in THF (1.5 mmol) at room temperature. The colorless solution was stirred for 4 hr at room temperature and then diluted by addition of 150 mL of $CH_2Cl_2$ and water (50 mL). The aqueous layers were extracted three times with $CH_2Cl_2$, and then dried over $Na_2SO_4$, filtered and evaporated. Purification by silica gel column chromatography using 1-2% MeOH in $CH_2Cl_2$ as eluent gave the desired compound 4.3 (460 mg, 67%) as a white solid.

Example 4

Step-D: 4-Chloro-7-[2-C-methyl-3,5-bis-O-(2,4-dichlorophenylmethyl)-β-D-ribofuranosyl]-5-(2-phthalimidoproyl)-7H-pyrrolo[2,3-d]pyrimidine (4.4)

To a solution of compound 4.3 (1.28 g, 1.89 mmol) in THF (70 mL) were added triphenylphosphine (648 mg, 2.47 mmol) and phthalimide (364.0 mg, 2.47 mmol) followed by DEAD (440 μL, 2.53 mmol), and the solution was stirred for overnight at room temperature. The reaction mixture was diluted by adding 100 mL of $CH_2Cl_2$ and water (100 mL) and the aqueous layers extracted three times with $CH_2Cl_2$, dried over $Na_2SO_4$, filtered and evaporated. The residue obtained was purified by flash column chromatography using 20-30% EtOAc in hexanes as eluent to give the desired compound 4.4 (1.5 g, 100%) as a white solid.

Example 4

Step-E: 2-[2-C-methyl-3,5-bis-O-(2,4-dichlorophenylmethyl)-β-D-ribofuranosyl]-6,7,8,9-tetrahydro-2H-2,3,5,6-tetraazabenzo[cd]azulene (4.5)

To a solution of compound 4.4 (161 mg, 0.2 mmol) in absolute EtOH (15 mL) was added ethylenediamine (24 μL, 0.4 mmol) and the mixture was stirred at 50° C. for 2 days. The solvents were evaporated and the residue was purified by column chromatography using 2-3% MeOH in $CH_2Cl_2$ as eluent to give the desired compound 4.5 (70.7 mg, 55%) as an off-white foam.

Example 4

Step-F: 2-(2-C-methyl-β-D-ribofuranosyl)-6,7,8,9-tetrahydro-2H-2,3,5,6-tetraazabenzo[cd]azulene (4.6)

To a solution of compound 4.5 (68.0 mg, 0.1 mmol) in $CH_2Cl_2$ (10 mL) at −78° C. was added 1.0 M solution of $BCl_3$ in $CH_2Cl_2$ (1.07 mmol) dropwise via syringe. The mixture was stirred at −78° C. for 1.5 h, then for 3 hr at −35° C. to −40° C. The reaction was quenched by adding MeOH (6.0 mL), the solvents were evaporated and the resulting residue was purified by flash column chromatography over silica gel using 6-7% MeOH in $CH_2Cl_2$ as eluent to give title compound 4.6 (31.8 mg) as a white foam.

$^1$H NMR (DMSO-$d_6$) d 7.99 (s, H-2, 1H), 7.5 (s, NH, 1H), 7.23 (s, H-7, 1H), 6.12 (s, H-1', 1H), 3.82-3.94 (m, H-3', H-4', H-5', 4H), 2.78 (m, $NCH_2CH_2CH_2$, 2H), 1.9 (m, $NCH_2CH_2CH_2$, 4H), 0.70 (s, $CH_3$, 3H). MS m/z 379 $(M+CH_3COO)^-$

Example 5

2-(2-O-Methyl-β-D-ribofuranosyl)-2,6-dihydro-7H-2,3,5,6-tetraazabenzo[cd]azulen-7-one (5.9)

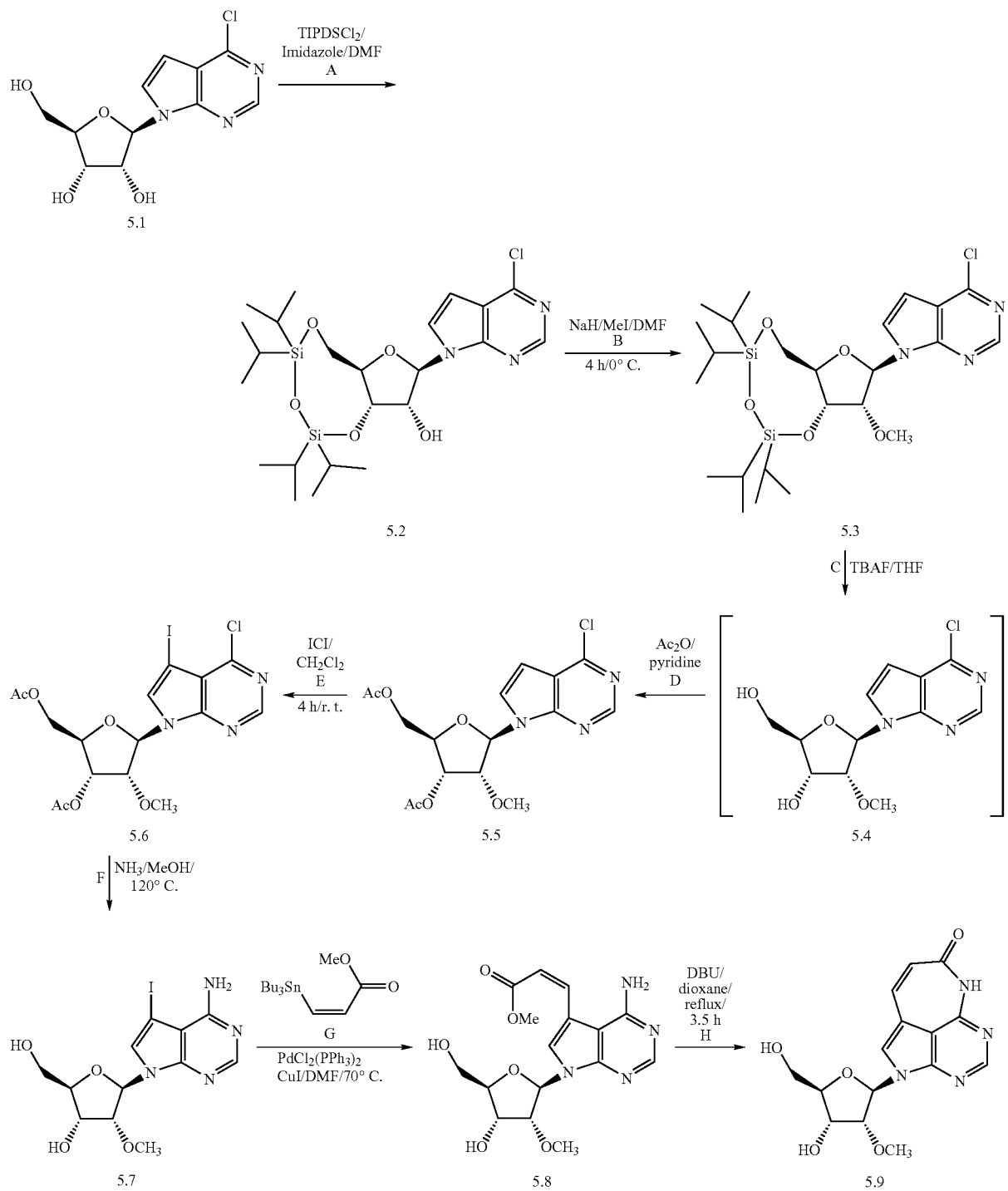

Selective 2'-O-methylation of tricyclic nucleosides was sought by introduction of selective and simultaneous protection of 3' and 5'-hydroxyl groups in 5.1 through a 3',5'-O-tetraisopropyldisiloxane bridge, followed by methylation and removal of 3',5'-OH protection to afford 5.4.

Reaction of commercially available 6-chlorotubercidine 5.1 with $TIPDSCl_2$/imidazole in DMF/room temperature/overnight gave 5',3'-O TIPDS protected compound 5.2 in 75% yield. Methylation of 5.2 in DMF using NaH/MeI/4 h/0° C. gave 2'OCH$_3$ compound 5.3 in 35% yield (2 steps). It was found that by decreasing the reaction time from 4 hr to 1 h, compound 5.3 could be isolated in 68% yield. Removal of the TIPDS of 5.3 was accomplished by using 4 equivalent of 1.0M tetrabutylammonium fluoride in THF at 0° C./1 hr to give 5.4. Intermediate 5.4 was acetylated using $Ac_2O$/pyridine to give 5.5 in quantitative yield. Iodination of 5.5 using ICl in $CH_2Cl_2$ gave the iodo compound 5.6 in 66% yield and subsequent amination of 5.6 with methanolic ammonia 120° C./16 h provided 5.7 in 89% isolated yield. Stille coupling of 5.7 using (Z)-methyl-3-(tributylstannyl) acrylate provided 5.8 (Z isomer) in 27% yield and the Stille coupling product 5.8, when subjected to cyclization using DBU/dioxane afforded target tricyclic nucleoside 5.9 in 48% yield.

Example 5

Step-A: 4-Chloro-7-[3,5-O-(tetraisopropyldisiloxane-1,3-diyl)-β-D-ribofuranosyl]-7H-pyrrolo[2,3-d]-pyrimidine (5.2)

To a solution of commercially available 6-chlorotubercidine 5.1 (3.0 g, 10.5 mmol) in DMF (140 mL) was added imidazole (3.6 g, 52.9 mmol), and $TIPDSiCl_2$ (1.2 eq) (4.0 mL, 12.5 mmol) at room temperature under argon. The reaction mixture was stirred for 16 h at room temperature and then quenched by adding 20 mL of EtOH. The solvents were evaporated, water (100 mL) was added and the white suspension was extracted, with $CH_2Cl_2$. The organic extracts were dried over $Na_2SO_4$, filtered, evaporated and the residue purified by flash column chromatography using gradient 5-7% EtOAc in hexanes to give the desired compound 5.2 (4.14 g, 75%) as a glassy solid.

Example 5

Step-B: 4-Chloro-7-[2-O-methyl-3,5-O-(tetraisopropyldisiloxane-1,3-diyl)-β-D-ribofuranosyl]-7H-pyrrolo[2,3-d]pyrimidine (5.3)

To a solution of compound 5.2 (2.0 g, 3.79 mmol) in DMF (45.0 mL) at 0° C., was added methyl iodide (1.88 mL, 15.23 mmol) followed by NaH (in one portion) (228 mg, 5.7 mmol, 60% suspension). The resulting reaction mixture was stirred for 1 hr at 0° C. and then quenched with anhydrous ethanol (20 mL) and diluted with 100 mL of $CH_2Cl_2$. The diluted reaction mixture was washed with water and the organic phase was dried over $Na_2SO_4$, filtered, evaporated and coevaporated three times with toluene. The residue obtained was purified by flash column chromatography using a gradient of 5-7% EtOAc in hexanes and afforded the desired 2'-O-methyl nucleoside 5.3 (1.4 g, 68%)

Example 5

Step-C: 4-Chloro-7-(2-O-methyl-β-D-ribofuranosyl)-7H-pyrrolo[2,3-d]pyrimidine (5.4)

To a solution of compound 5.3 (3.62 g, 6.66 mmol) in THF (100 mL), was added a 1.0 M solution of tetrabutylammonium fluoride in THF (26.0 mmol) at room temperature. The colorless solution was stirred for 1 hr at room temperature and then diluted by adding 150 mL of $CH_2Cl_2$ and water 50 mL. The aqueous portion was extracted three times with $CH_2Cl_2$, dried over $Na_2SO_4$, filtered and evaporated. Purification by silica gel column chromatography using pure $CH_2Cl_2$ to 2% MeOH in $CH_2Cl_2$ as eluent gave the desired compound 5.4 (1.24 g, 59%) as a colorless oil.

Example 5

Step-D: 4-Chloro-7-(2-O-methyl-3,5-di-O-acetyl-β-D-ribofuranosyl)-7H-pyrrolo[2,3-d]pyrimidine (5.5)

To a solution of compound 5.4 (2.44 mmol) pyridine (40 mL), was added acetic anhydride (1.23 mL, 8.44 mmol) via syringe and the solution stirred overnight at room temperature. The solvents were evaporated in vacuo, the residue was dissolved in $CH_2Cl_2$ and the solution was washed with water then dried over $Na_2SO_4$, filtered, evaporated and co-evaporated with toluene three times. The residue obtained was purified by dash column chromatography using a gradient of pure $CH_2Cl_2$ to 2.5% MeOH in $CH_2Cl_2$ to give the desired compound 5.5 (1.26 g) as a colorless oil.

Example 5

Step-E: 4-Chloro-5-iodo-7-(2-O-methyl-3,5-di-O-acetyl-β-D-ribofuranosyl)-7H-pyrrolo[2,3-d]pyrimidine (5.6)

To a solution of compound 5.5 (1.25 g, 3.26 mmol) in $CH_2Cl_2$ (80 mL), a 1.0 M solution of ICl in $CH_2Cl_2$ (8.12 mmol) was added at room temperature and the resulting dark brown solution was stirred for 4 hr at room temperature. The solvents were evaporated in vacuo at 25° C.-35° C. and the residue was dried under high vacuum for 30 min. A light brown sticky material was obtained which was purified by flash column chromatography using gradient of pure $CH_2Cl_2$ to 1.5% MeOH in $CH_2Cl_2$ to afford the desired compound 5.6 (1.1 g, 66%) as a white solid.

Example 5

Step-F: 4-Amino-5-iodo-7-(2-O-methyl-β-D-ribofuranosyl)-7H-pyrrolo[2,3-d]pyrimidine (5.7)

A solution of compound 5.6 (28.8 mg, 0.057 mmol) in MeOH (3 mL) was transferred to a steel bomb, cooled to −50 to −60° C., and treated with a saturated solution of ammonia in MeOH (10 mL). The reactor was sealed and heated at 118° C. overnight. The reaction vessel was cooled (0-5° C.), opened carefully and the reaction mixture was evaporated to dryness. The crude product was dissolved in MeOH, adsorbed onto silica gel and purified by flash column chromatography on silica gel using pure $CH_2Cl_2$ to 4% MeOH in $CH_2Cl_2$ as eluents to give the desired compound 5.7 (20.7 mg) as an off white solid.

Example 5

Step-G: 4-Amino-7-(2-O-methyl-β-D-ribofuranosyl)-3-[2-methoxycarbonyl)ethenyl]-7H-pyrrolo[2,3-d]pyrimidine (5.8)

To a solution of compound 5.7 (156 mg, 0.38 mmol) in DMF (12.0 mL), were added (Z)-methyl-3-(tributylstannyl)acrylate (*J. Am. Chem. Soc.*, 1993, 115, 1619) (0.29 mL, 0.77 mmol) and CuI (14.6 mg, 0.08 mmol). The mixture was stirred for 10 min at room temperature and then Pd(PPh$_3$)$_2$Cl$_2$ was added, and reaction the mixture was heated for 3.5 h at 70° C. under argon. The reaction mixture was cooled to room temperature and filtered through a celite pad. The celite pad was washed with 8 mL of 1/1 MeOH/CH$_2$Cl$_2$. After filtration, the washings were combined and the solvents were evaporated in vacuo. The residue was redissolved in MeOH and adsorbed onto silica gel and purified by flash column chromatography using 2.5% MeOH in CH$_2$Cl$_2$ as eluent to give the desired compound 5.8 (38 mg, 27%) as a yellow solid.

Example 5

Step-H: 2-(2-O-Methyl-β-D-ribofuranosyl)-2,6-dihydro-7H-2,3,5,6-tetraazabenz[cd]azulen-7-one (5.9)

To a solution of compound 5.8 (36 mg, 0.1 mmol) in 1,4-dioxane (6.0 mL), were added 3A molecular sieves followed by DBU (38 μL, 0.25 mmol). The reaction mixture was stirred for 3.5 h at 110° C. and then cooled to room temperature and filtered, the solvents were evaporated and the residue purified by flash column chromatography using CH$_2$Cl$_2$ to 2% MeOH in CH$_2$Cl$_2$ as eluent to give title compound 5.9 (16 mg) as an off white solid.

$^1$H NMR (DMSO-d$_6$) d 10.69 (s, NH, 1H), 8.33 (s, H-4, 1H), 7.8 (s, H-1, 1H), 7.04 (d, J 11.7 Hz, CH, 1H), 6.13 (d, J 6.0 Hz, H-1', 1H), 5.67 (d, J 11.7 Hz, CH, 1H), 5.25 (d, J 5.4 Hz, 3'-OH, 1H), 5.12 (t, J 5.7 Hz, 5'-OH, 1H ), 4.24-4.27 (m, H-4', 1H), 4.12-4.15 (m, H-3', 1H), 3.93 (m, H-2', 1H), 3.55-3.61 (m, H-5', 2H), 3.28 (s, OCH$_3$, 3H). MS m/z 331 (M-H)$^+$

Example 6

2-(2-C-Methyl-β-D-ribofuranosyl]-2,6-dihydro-7H-2,3,5,6-tetraazabenzo[cd]azulen-7-one (6.6)

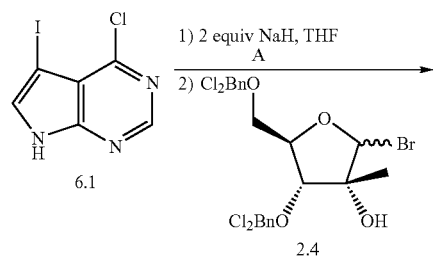

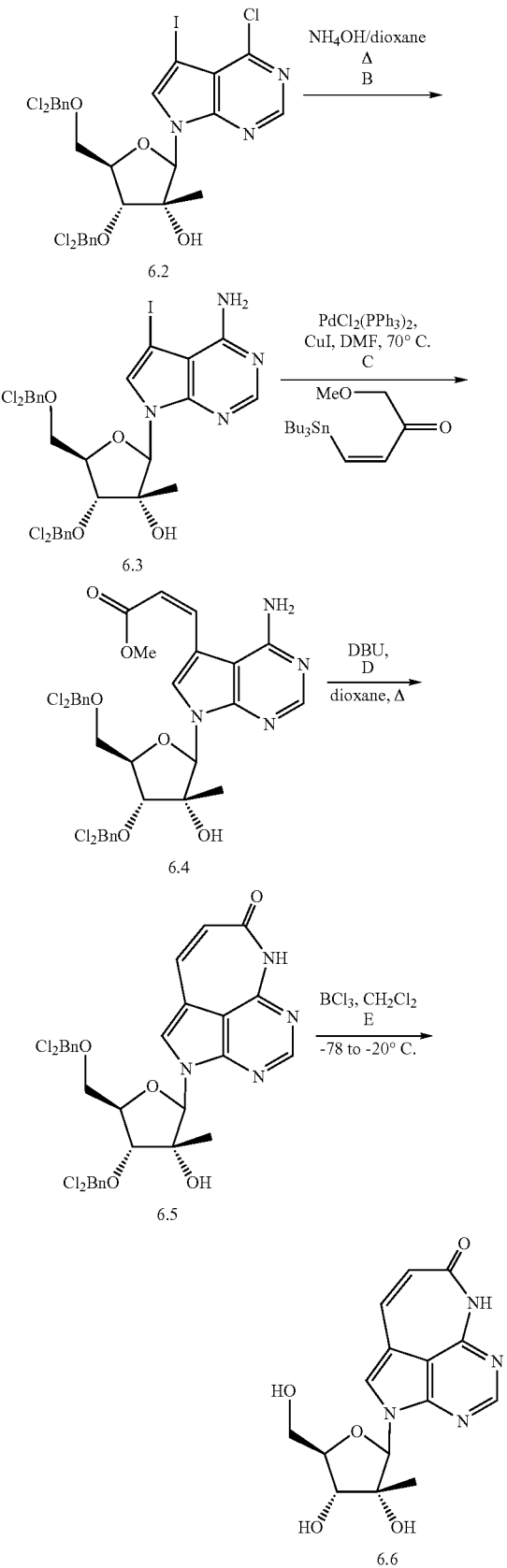

The tricyclic nucleoside 6.7 was synthesized starting from 4-chloro-1H-pyrrolo[2,3-d]pyrimidine 2.1. The nucleobase 2.1 was treated with N-iodosuccinimide in THF at room temperature for 4 hr to provide 4-chloro-5-iodo-7H-pyrrolo [2,3-d]pyrimidine 6.1. Then 6.1 was converted to the corresponding sodium salt with sodium hydride in acetonitrile and reacted with bromo-sugar 2.4 ((i)*Helv. Chim. Acta.* 1995, 78, 486; (ii) WO 02/057287, 2002), to give nucleoside 6.2. which was directly converted to 4-amino-5-iodo-7-[3,5-bis-O-(2,4-dichlorophenylmethyl)-2-C-methyl-β-D-ribofuranosyl]-7H-pyrrolo[2,3-d]pyrimidine 6.3. A Stille coupling reaction between nucleoside 6.3 and Z-3-tributylstannylacrylate provided compound 6.4. The cyclization of compound 6.4 was accomplished by heating in DBU/dioxane overnight to afford the protected tricyclic nucleoside 6.5, which was then treated with boron trichloride in $CH_2Cl_2$ to produce nucleoside 6.6.

4-chloro-5-iodo-7H-pyrrolo[2,3-d]pyrimidine (6.1)

Compound 6.1 was prepared according to a published procedure (Townsend, L. B. et al., 1990, 33, 1982-1992.

Example 6

Step A: 4-Chloro-5-iodo-7-[3,5-bis-O-(2,4-dichlorophenylmethyl)-2-C-methyl-β-D-ribofuranosyl]-7H-pyrrolo[2,3-d]pyrimidine (6.2)

Compound 2.4 was prepared according to the published procedure. ((i). *Helv. Chim. Acta.* 1995, 78, 486; (ii). WO 02/057287, 2002).

A solution of compound 2.4 (25 mmol) in anhydrous acetonitrile (90 mL) was added to a solution of the sodium salt of 4-chloro-5-iodo-1H-pyrrolo[2,3-d]pyrimidine [generated in situ from 4-chloro-5-iodo-1H-pyrrolo[2,3-d]pyrimidine 6.1 (6.99 g, 25 mmol) in anhydrous acetonitrile (250 mL), and NaH (60% in mineral oil, 1.0 g, 25 mmol), after 4 hr of vigorous stirring at room temperature]. The combined mixture was stirred at room temperature for 24 h, and then evaporated to dryness. The residue was suspended in water (250 mL) and extracted with $CH_2Cl_2$ (2×500 mL). The combined extracts were washed with brine (300 mL), dried over $Na_2SO_4$, filtered and evaporated. The crude product was purified on a silica gel column using ethyl acetate/hexanes (1/4-1/2) as the eluent. Fractions containing the product were combined and evaporated in vacuo to give the desired product 6.2 (6.26 g, yield 34%) as light yellow foam.

Example 6

Step B: 4-amino-5-iodo-7-[3,5-bis-O-(2,4-dichlorophenylmethyl)-2-C-methyl-β-D-ribofuranosyl]-7H-pyrrolo[2,3-d]pyrimidine (6.3)

To a compound 6.2 (5 g, 6.7 mmol) in dioxane (100 mL) was added conc. $NH_4OH$ (100 mL). The mixture was heated in a stainless steel autoclave at 100° C. for 3 h, then cooled and evaporated in vacuo. The crude mixture was dissolved in 100 mL of $CH_2Cl_2$ and washed with water and brine, dried over $MgSO_4$, filtered and concentrated to provide crude product. The crude product was then purified on a silica gel column with 5% MeOH in $CH_2Cl_2$ as eluent to give 4.32 g of 6.3 as white foam (yield 88%).

Example 6

Step C: 4-Amino-5-[2-(methoxycarbonyl)ethenyl]-7-[3,5-bis-O-(2,4-dichlorophenylmethyl)-2-C-methyl-β-D-ribofuranosyl]-7H-pyrrolo[2,3-d]pyrimidine (6.4)

To a solution of compound 6.3 (1.25 g, 1.726 mmol) in 10 mL of anhydrous DMF was added Z-3-tributylstannylacrylate (1.1 mL, 2 eq.) (*J. Am. Chem. Soc.*, 1993, 115, 1619), CuI (66 mg, 0.2 eq.) and $PdCl_2(PPh_3)_2$ (121 mg, 0.1 eq.) at room temperature under the argon atmosphere. The reaction mixture was heated at 70° C. for 8 hr. Then the reaction mixture was cooled to room temperature and filtered through a celite pad. The filtrate was concentrated in vacuo to provide an orange-red oil as the crude product which was purified on a silica gel column with 10-30% THF in $CH_2Cl_2$ as eluent to give 995 mg 6.4 as yellow foam (yield 81%).

Example 6

Step D: 2-[3,5-Bis-O-(2,4-dichlorophenylmethyl)-2-C-methyl-β-D-ribofuranosyl]-2,6-dihydro-7H-2,3,5,6-tetraazabenzo[cd]azulen-7-one (6.5)

To a solution of the compound 6.4 (1.15 g, 1.69 mmol) in 150 mL of anhydrous dioxane under an argon atmosphere at room temperature was added DBU (630 μL, 2.5 eq.) and 1 g of 4A molecular sieves. The reaction mixture was heated at reflux for 16 hr then cooled to room temperature and evaporated to dryness in vacuo. The residue was purified by silica gel chromatography with 1% MeOH in $CH_2Cl_2$ as eluent to provide 772 mg of compound 6.5 as a yellow solid (yield: 71%).

Example 6

Step E: 2-(2-C-Methyl-β-D-ribofuranosyl)-2,6-dihydro-7H-2,3,5,6-tetraazabenzo[cd]azulen-7-one (6.6)

To a solution of the compound 6.5 (0.71 g, 1.1 mmol) in 30 mL of anhydrous $CH_2Cl_2$ at −78° C. was added boron trichloride (1M solution in $CH_2Cl_2$, 11 mL, 11 mmol) dropwise. The mixture was stirred at −78° C. for 2.5 h, then at −30° C. to −20° C. for 3 hr. The reaction was quenched by addition of methanolic/$CH_2Cl_2$ (1:1) (5 mL) and the resulting mixture stirred at −15° C. for 30 min., then neutralized with aqueous ammonia at 0° C. and stirred at room temperature for 15 min. The solid was filtered and washed with $CH_2Cl_2$/MeOH (1/1, 3×30 mL). Chromatography over silica gel using 5% MeOH in $CH_2Cl_2$ as eluent furnished the 282 mg of the desired compound 6.6 as a yellow solid (yield: 77.8%). $^1$H NMR (300 MHz, DMSO-$d_6$) δ 10.67 (br s 1H, NH), 8.32 (s, 1H, H-4), 7.86 (s, 1H, H-1), 7.00 (d, J 12.6 Hz, H-8), 6.09 (s, 1H, H-1'), 5.63 (d, J 12.6 Hz, H-9), 5.16 (m, 3H, 3×OH), 3.95 (m, 1H, H-3'), 3.88-3.56 (m, 3H, H-4', 2×H-5'), 0.73 (s, 3H, $CH_3$); ES MS: 391.5 $(M+CH_3COO)^-$.

Example 7
2-(2-C-methyl-β-D-ribofuranosyl)-8,9-dihydro-3,5,6,9a-tetraazabenzo[cd]azulene (7.14)
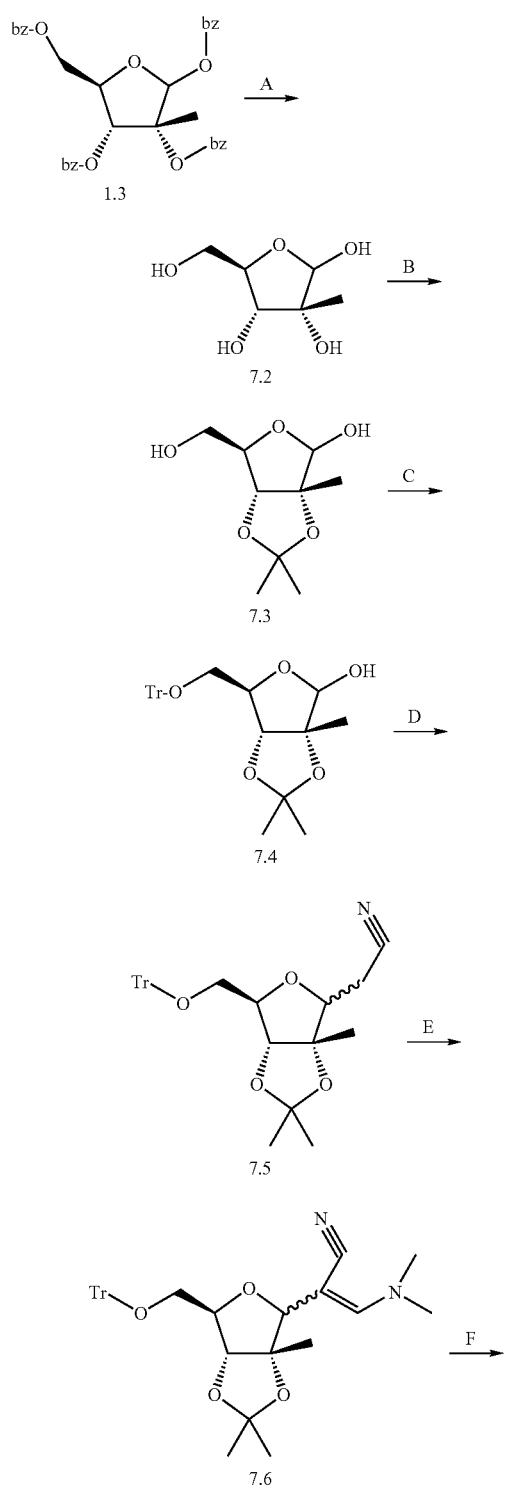
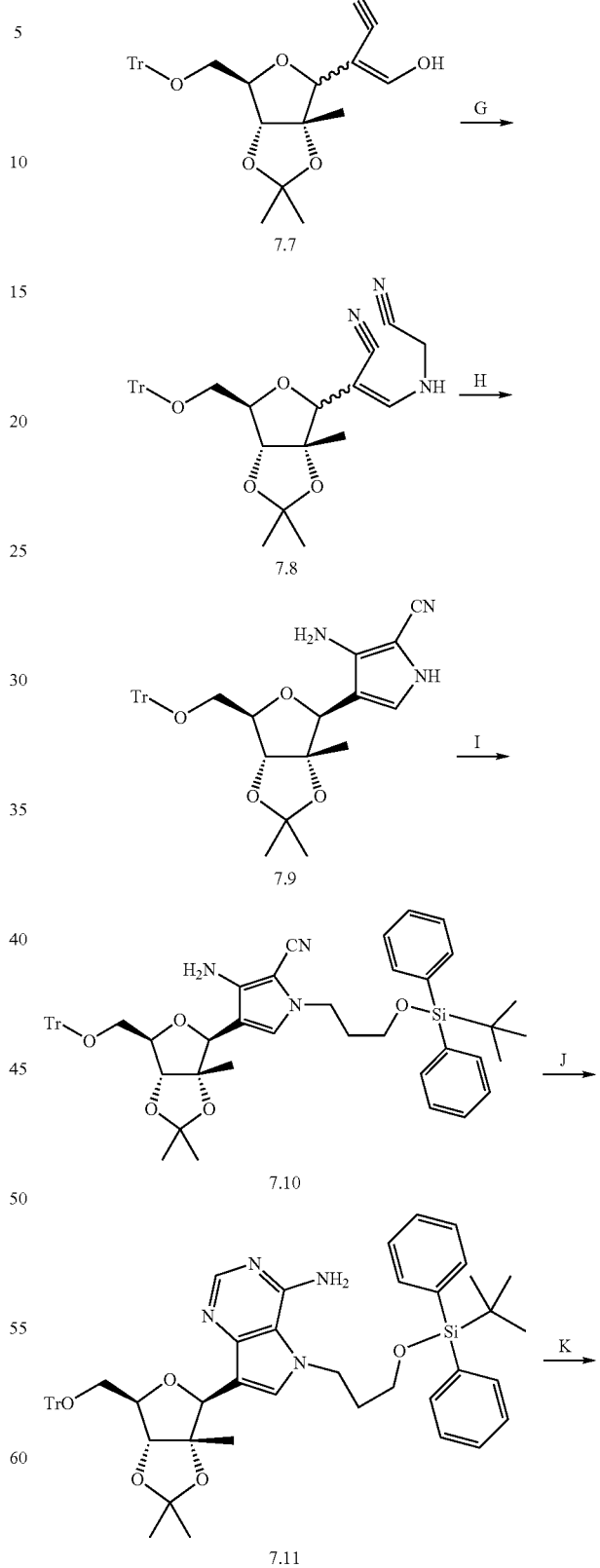

-continued

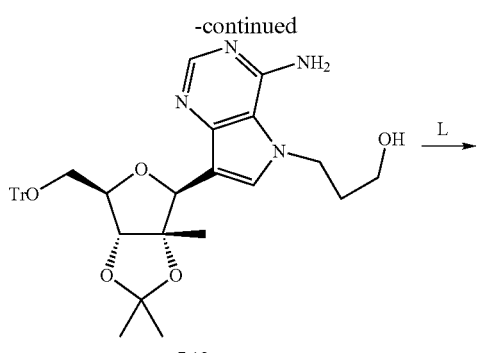

7.12

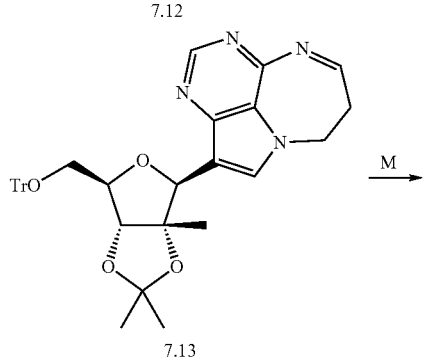

7.13

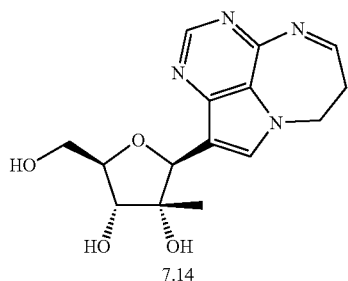

7.14

Example 7

Step A: 2-C-Methyl-D-ribofuranose (7.2)

To a suspension of 2-C-methyl-1,2,3,5-tetra-O-benzoyl-β-D-ribofuranose 1.3, (50 g) in anhydrous MeOH (1000 mL) was added KCN (150 mg) and the mixture was allowed to stir at room temperature under argon for 15 hr during which time all the material dissolved in the solvent and the solution became clear. The solvent was evaporated and the residue was dried under vacuum to deliver 14.9 g of product 7.2.

Example 7

Step B: 2,3-O-Isopropylidene-2-C-methyl-D-ribofuranose (7.31)

The material from Step A (7.2) (14.9 g, 86 mmol) was dissolved in dry acetone (1000 mL) and 1 mL of conc. $H_2SO_4$ was added. The mixture was stirred at room temperature overnight and then carefully neutralized with saturated aqueous $NaHCO_3$ and the solvent evaporated. The residue was dissolved in 500 mL ethyl acetate and washed with water (100 mL) and brine (100 mL). The solution was dried over $Na_2SO_4$, filtered and evaporated. The residue was purified on a silica gel column using 2:1 hexanes:EtOAc. Evaporation of the solvent afforded 14 g of the product 7.3.

Example 7

Step C: 2,3-O-Isopropylidene-2-C-methyl-5-O-(triphenylmethyl)-D-ribofuranose (7.4)

To a solution of compound 7.3 (13.7 g, 67.4 mmol) in pyridine was added chlorotriphenylmethane (23.5 g, 84.2 mmol) and the mixture was heated at 60° C. for 15 hr under an argon atmosphere. The solvent was evaporated and the residue was dissolved in ethyl acetate (200 mL) and washed with water (150 mL), brine (150 mL) and dried over sodium sulphate. After filtration and evaporation, the residue was loaded on a silica gel column and eluted with 10:1 followed by 5:1 hexane:ethyl acetate. Evaporation of solvent under reduced pressure afforded 15 g of 7.4 as a colorless syrup.

Example 7

Step D: 3,6-Anhydro-2-deoxy-4,5-O-isopropylidene-4-C-methyl-7-O-(triphenylmethyl)-D-allo- and D-altro-septononitrile (7.5)

To a suspension of NaH (95%, 1.23 g, 48.2 mmol) in dry DME (250 mL), diethyl cyanomethylenephosphonate (10.06 mL, 62 mmol) was added dropwise at 0° C. over 15 minutes. After evolution of hydrogen ceased, compound 7.4 (15 g, 33.5 mmol), in 250 mL dry DME was added to the resulting solution over 30 minutes and then the mixture was stirred at room temperature for 2 hr. The reaction mixture was partitioned between ether (1000 mL) and water (1000 mL) and the aqueous layer was extracted with 1000 mL ether. The combined ether extracts were washed with water, dried ($Na_2SO_4$) and filtered. The solvent was evaporated under reduced pressure, and the residue was purified by silica gel column chromatography using 4:1 hexane:ethyl acetate as eluent. The solvent was evaporated to give 7.5 as an off-white foam (14.8 g).

Example 7

Step E: (2E)-3,6-Anhydro-2-deoxy-2-C-[(N,N-dimethylamino)methylidene]-4,5-O-isopropylidene-4-C-methyl-7-O-(triphenylmethyl)-D-allo- and D-altro-septononitrile (7.6)

To a solution of compound 7.5 (13.0 g, 27.68 mmol) in anhydrous $CH_2Cl_2$ (60 mL) was added bis(dimethylamino)-tert-butoxymethane (22.87 mL, 110.74 mmol) followed by dry dimethylformamide (2.3 mL). The mixture was stirred at room temperature for 20 hr. After removal of solvents the mixture was chromatographed on a silica gel column pretreated with triethylamine to deliver 11.4 g of 7.6 as a viscous oil.

Example 7

Step F: (2E)-3,6-Anhydro-2-deoxy-2-C-(hydroxymethylidene)-4,5-O-isopropylidene-4-C-methyl-7-O-(triphenylmethyl)-D-allo- and D-altro-septononitrile (7.7)

To a solution of compound 7.6 (6 g, 11.44 mmol) in $CHCl_3$ (120 mL) was added a solution of TFA (3 mL) in water (200 mL) and the mixture was stirred vigorously at room temperature for 16 hr. The organic layer was separated and washed with water and dried ($Na_2SO_4$) then filtered. Removal of solvent afforded 2-formyl nitrile (7.7) (2.5 g) in a form that was used as such in the next step.

Example 7

Step G: (2E)-3,6-Anhydro-2-deoxy-2-C-[(cyanomethylamino)methylidene]-4,5-O-isopropylidene-4-C-methyl-7-O-triphenylmethyl)-D-allo- and D-altro-septononitrile (7.8)

Crude 7.7 was dissolved in MeOH (25 mL) and 1.6 mL water was added followed by aminoacetonitrile hydrochloride (0.78 g, 8.77 mmol) and sodium acetate trihydrate (1.3 g, 9.55 mmol). The mixture was stirred at room temperature for 16 hr. After evaporation of the solvent, the residue was dissolved in a minimum volume of $CH_2Cl_2$ and loaded on a silica gel column which was eluted with 30:1 $CH_2Cl_2$: MeOH. Evaporation of solvent under reduced pressure gave 2.2 g of product 7.8 as an anomeric mixture.

Example 7

Step H: 3-Amino-2-cyano-4-(2,3-O-isopropylidene-2-C-methyl-5-O-triphenylmethyl-β-D-ribofuranosyl)-1H-pyrrole (7.9)

To a solution of compound 7.8 (8 g, 14.94 mmol) in $CH_2Cl_2$ (100 mL) at 0° C. was added 1,5-diaza[4.3.0]non-5-ene (DBN) (2.95 mL, 23.89 mmol) followed by ethyl chloroformate (2.35 mL, 23.89 mmol). The mixture was kept at 0-4° C. for 16 hr. Additional 2 mL of DBN was added and the mixture was stirred at room temperature for 24 hr. After evaporation of the solvent the residue was purified on silica gel column using 4:1 hexanes:EtOAc followed by 3:1 hexanes:EtOAc to obtain a major fraction as mixture of anomers. To this mixture of anomers (6.42 g, 10.56 mmol) in MeOH (100 mL) was added sodium carbonate (3 g) and stirred at room temperature for 1 hr. The insoluble residue was filtered off and the solvent was removed under vacuum. The residue was purified on a silica gel column using 3:1 hexanes:EtOAc to obtain 5 g of product 7.9 as β anomer.

Example 7

Step I

Part A.: 3-(tert-Butyldiphenylsilyloxy)propyl 4-methylbenzenesulfonate

The title compound was prepared according to the procedure described by Caprio et al. *Tetrahedron*, 2001, 57, 4023-4034.

Part B: 3-Amino-1-(3-tert-butyldiphenylsilyloxypropyl)-2-cyano-4-(2,3-O-isopropylidene-2-C-methyl-5-O-triphenylmethyl-β-D-ribofuranosyl)-1H-pyrrole (7.10)

To a solution of potassium t-butoxide (1M THF solution, 4.32 mL) in THF (30 mL) was added compound 7.9 (2 g, 3.73 mmol), followed by catalytic amount of 18-crown-6. The mixture was stirred under argon for 10 minutes during which time the solution turned clear reddish brown. To this solution was added the compound prepared according Part A (3.68 g, 7.47 mmol) dissolved in 1.5 m of (anhydrous) dichloroethane. After 1 hour, a further equivalent of tosylate was added and the mixture was stirred at room temperature overnight. After evaporation of the solvent under vacuum, the residue dissolved in minimum $CH_2Cl_2$ was loaded on a silica gel column and eluted with 6:1 followed by 4:1 hexane:EtOAc. Evaporation of the solvent from the appropriate fractions afforded 1.5 g of product 7.10.

Example 7

Step J: 4-Amino-5-(3-tert-butyldiphenylsilyloxypropyl)-7-(2,3-O-isopropylidene-2-C-methyl-5-O-triphenylmethyl-β-D-ribofuranosyl)-5H-pyrrolo[3,2-d]pyrimidine (7.11)

Compound 7.10 (600 mg, 0.72 mmol) and formamidine acetate (227.5 mg, 2.61 mmol) were mixed with 20 mL ethyl alcohol and heated at reflux under argon atmosphere for 8 hr. The solvent was evaporated and the residue was loaded on a silica gel column and eluted with 20:1 MeOH:$CH_2Cl_2$ to afford 555 mg product 7.11.

Example 7

Step K: 4-Amino-5-(3-hydroxypropyl)-7-(2,3-O-isopropylidene-2-C-methyl-5-O-triphenylmethyl-β-D-ribofuranosyl)-5H-pyrrolo[3,2-d]pyrimidine (7.12)

Compound 7.11 (555 mg, 0.65 mmol) was dissolved in anhydrous THF (10 mL) and 1.3 mL (1.3 mmol) of a 1M THF solution of tetrabutylammonium fluoride was added. The mixture was stirred at room temperature for 2 hr and the solvent was then evaporated under reduced pressure and the residue was loaded on a silica gel column and eluted with 15:1 $CH_2Cl_2$:MeOH to give 281 mg of product 7.12.

Example 7

Step L: 2-(2,3-O-Isopropylidene-2-C-methyl-5-O-triphenylmethyl-β-D-ribofuranosyl)-8,9-dihydro-3,5,6,9a-tetraazabenzo[cd]azulene (7.13)

Compound 7.12 (160 mg, 0.26 mmol) was taken up in 2 mL $CH_2Cl_2$ and kept at 0° C. To this was added TEMPO (2,2,6,6-tetramethyl-1-piperidinyloxy, free radical, 1 mg) followed by an aqueous solution KBr (1 mg in 0.2 mL water) and Aliquat®366 (6 μL) and NaOCl (0.35 M, 0.92 mL). The mixture was stirred at 0° C. for 30 minutes. More $CH_2Cl_2$ was added and the reaction was washed with water (5 mL). The organic layer was dried over $Na_2SO_4$, filtered and evaporated under reduced pressure. The residue was used in the next step without further purification.

Example 7

Step M: 2-(2-C-methyl-β-D-ribofuranosyl)-8,9-dihydro-3,5,6,9a-tetraazabenzo[cd]azulene (7.14)

Compound 7.13 was heated at 80° C. in 90% acetic acid for 12 hr. The solvent was evaporated and the crude product was purified by reverse phase HPLC on a C18 column to afford 3 mg pure product 7.14. $^1$H NMR (DMSO-$d_6$). δ 8.10 (s, 1H), 7.49 (s, 1H), 6.60 (s, 1H), 5.33 (s, 1H), 4.57 (m, 3H), 4.03 (m, 1H), 3.72 (m, 1H), 3.51 (m, 2H), 2.91 (m, 2H), 2.77 (m, 2H), 1.02 (s, 3H).

Example 8

2-(2-C-Methyl-β-D-ribofuranosyl]-2,6,8,9-tetrahydro-7H-2,3,5,6-tetraazabenzo[cd]azulen-7-one (8.1)

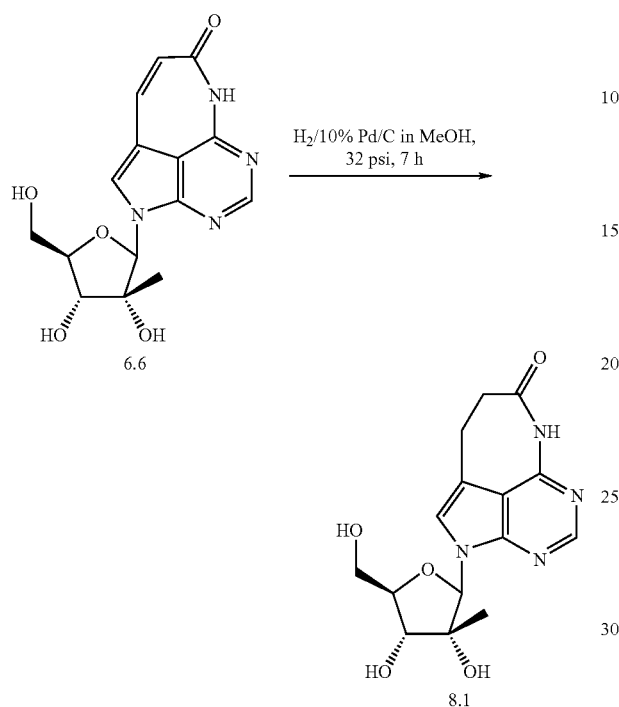

A mixture of tricyclic nucleoside 6.6 (20 mg, 0.06 mmol) and 10% Pd/C (12.8 mg, 0.2 eq.) in 20 mL of MeOH under H$_2$ pressure (32 psi) was shaken for 7 hr at room temperature. The mixture was filtered through 0.45 μM filter. The combined filtrates were evaporated and purified on a silica gel column with 5% MeOH in CH$_2$Cl$_2$. 12 mg of pure compound 8.1 was obtained (yield 60%). $^1$H NMR (300 MHz, DMSO-d$_6$): δ 10.65 (br s, 1H, NH), 8.37 (s, 1H, H-4), 7.48 (s, 1H, H-1), 6.12 (s, 1H, H-1'), 5.05 (m, 3H, 3×OH), 3.89-3.12 (m, 4H, H-3', H-4', 2×H-5'), 2.86-2.74 (m, 4H, 2×H-8, 2×H-9), 0.64 (s, 3H, CH$_3$); LCMS: ES-MS 393.6 (M+CH$_3$COO).

Example 9

2-(β-D-ribofuranosyl)-2,6-dihydro-7H-2,3,5,6-tetraazabenzo[c]azulen-7-one (9.4)

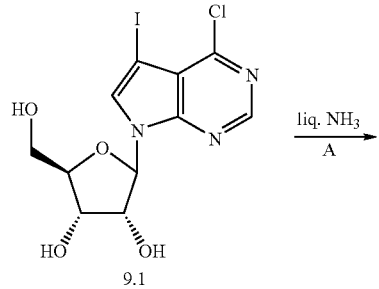

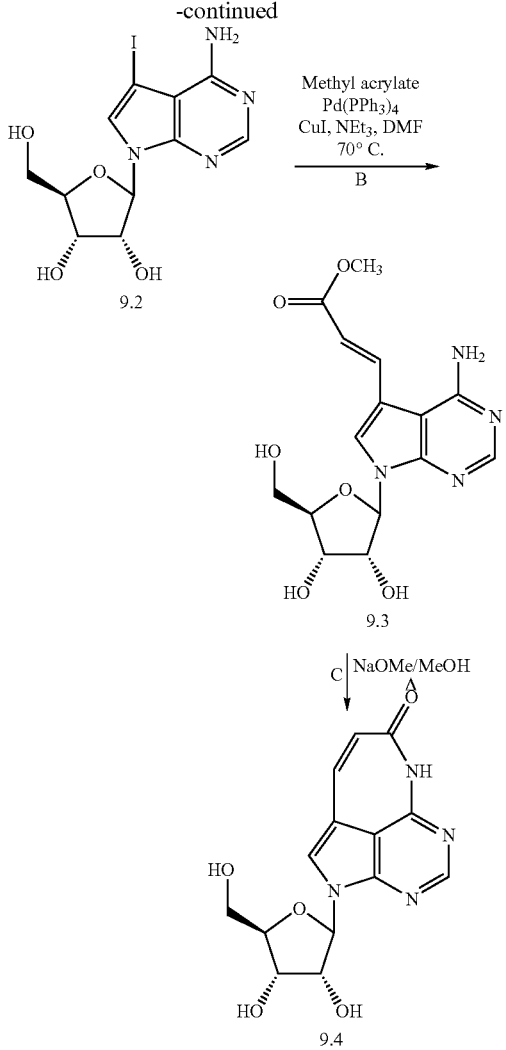

The nucleoside 9.2 was produced directly from nucleoside 9.1, which was prepared starting from D-ribose (Bheemarao G. et al; *J. Med. Chem.* 2000, 43, 2883-2893), using liquid ammonia at 85° C. overnight. The palladium[0] catalyzed cross-coupling reaction of compound 9.2, followed by the cyclization of compound 9.3 in 0.1 N NaOMe in MeOH, delivered the desired tricyclic nucleoside 9.4.

Example 9

Step A: 4-amino-5-iodo-7-β-D-ribofurnaosyl-7H-pyrrolo[2,3-d]pyrimidine (9.2)

Compound 9.2 was prepared according to a published method (Bergstrom, D. E., et al., *J. Org. Chem.*, 1981, 46, 1423).

Example 9

Step B: 4-Amino-5-[2-(methoxycarbonyl)ethenyl]-7-(2-C-methyl-β-D-ribofurnaosyl)-7H-pyrrolo[2,3-d]pyrimidine (9.3)

To a solution of compound 9.2 (300 mg, 0.76 mmol) in 10 mL of anhydrous DMF was added CuI (29 mg, 0.2 eq.), methyl acrylate (1.37 mL, 20 eq.), triethylamine (212 μL, 2 eq.) and Pd(PPh$_3$)$_4$ (88 mg, 0.1 eq.) at room temperature under an argon atmosphere. The reaction mixture was heated at 70° C. for 24 hr. then cooled to room temperature and 20 mL of 1/1 MeOH/CH$_2$Cl$_2$ was added. Then, 1.0 g Dowex 1×2-100 Bicarb form was added and the suspension stirred at room temperature for 45 min. then filtered. The resin was washed with 5×20 mL MeOH/CH$_2$Cl$_2$:1/1, DMF was finally evaporated by co-evaporation with toluene (2×10 mL). Chromatographic column purification on silica gel (eluent: CH$_2$Cl$_2$/MeOH:90/10) gave 224 mg of final product 9.3 (yield 84%)

$^1$H NMR (CD$_3$OD) δ 8.11 (s, 1H, H-2), 8.00 (s, 1H, H-6), 7.96 (d, J 15.54 Hz, 1H), 6.35 (d, J 15.54 Hz, H2''), 6.52 (d, 1H, H-1'), 4.43 (t, 1H, H-3'), 4.34-4.26 (m, 2H, H-4', H-2'), 3.85-3.64 (m, 2H, 2×H-5'), 3.79 (s, 3H, OCH$_3$).

Example 9

Step C: 2-(β-D-Ribofuranosyl)-2,6-dihydro-7H-2,3,5,6-tetraazabenzo[cd]azulen-7-one (9.4)

A solution of compound 9.3 (140 mg, 0.4 mmoles) in 0.1 M NaOMe in MeOH (80 mL) was heated at 70° C. for 4 hr. The solution was cooled and the solvent evaporated and the residue purified by silica gel column using CH$_2$Cl$_2$/MeOH: 90/10 as eluent to give the final product 9.4.

$^1$H NMR (CD$_3$OD) δ 8.32 (s, 1H, H-2), 7.86 (s, 1H, H-6), 7.07 (d, J 12 Hz, H-8), 6.09 (s, 1H, H-1'), 5.70 (d, J 12 Hz, H-9), 4.57 (m, 1H, H-2'), 4.29 (m, 1H, H-3'), 4.12 (m, 1H, H-4'), 3.88-3.72 (m, 2H, 2×H-5'); ES-MS: 377.4 (M+CH$_3$COO)$^-$.

Example 10

2-(3-Deoxy-β-D-ribofuranosyl)-2,6-dihydro-7H-2,3,5,6-tetraazabenzo[cd]azulen-7-one (10.6)

The nucleoside 5.1 was prepared starting from D-ribose ((i) *Journal of Heterocyclic Chemistry*, 25(6), 1893-8, 1988; (ii) *Helvetica Chimica Acta*, 71(6), 1573-85, 1988), then converted to the 3'-deoxy nucleoside 10.2 as follows: 4.0 equiv of α-acetoxyisobutyryl bromide was added to a suspension of nucleoside 5.1 in acetonitrile containing 1.1 equiv of H$_2$O at room temperature followed by treatment with DOWEX OH$^-$ resin in MeOH to afford a crystalline sample of 4-methoxy-7-(2,3-anhydro-β-D-ribofurnaosyl)-7H-pyrrolo[2,3-d]pyrimidine 10.1. The epoxide was treated with 4.0 equiv of LiEt$_3$BH in THF at room temperature to give the 3'-deoxynucleoside 10.2 in 50% combined yield for the two preceding steps. The 7-iodo group was introduced by reacting the 3'-deoxynucleoside 10.2 with N-iodosuccinimide in DMF to give compound 10.3 which, in turn, was treated with anhydrous liquid ammonia to provide compound 10.4. After the palladium[0] catalyzed cross-coupling reaction and cyclization to form the tricyclic target, the desired nucleoside 10.6 was obtained.

Example 10

Step A: 4-methoxy-7-(2,3-anhydro-β-D-ribofurnaosyl)-7H-pyrrolo[2,3-d]pyrimidine (10.1)

To a mixture of nucleoside 5.1 (250 mg, 0.875 mmol) in 12 mL of acetonitrile were added H$_2$O/acetonitrile (1/9) (157 μL, 1 eq.) and α-acetoxyisobutyryl bromide (0.537 mL, 4 eq.). After 2 hr stirring at room temperature, sat. NaHCO$_3$ (aq.) was added and the mixture was extracted with ethyl acetate. The combined organic extracts were washed with brine, dried over MgSO$_4$ and evaporated. The foamy residue was suspended in MeOH and stirred overnight with Dowex OH$^-$ previously washed with anhydrous MeOH). The resin was filtered off, washed with MeOH and the combined

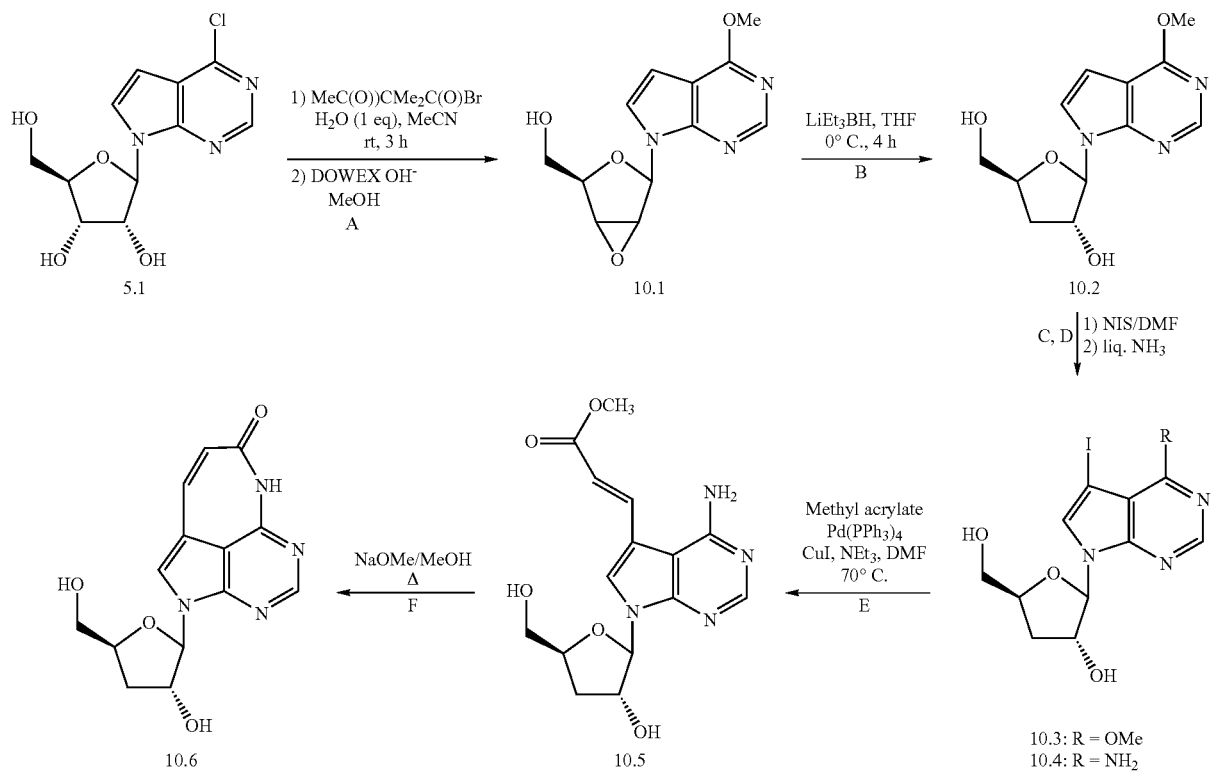

filtrates were evaporated to yield 225 mg of a pale yellow foam 10.1, which was directly used in the next step without further purification.

Example 10

Step B: 4-Methoxy-7-(3-deoxy-β-D-ribofurnaosyl)-7H-pyrrolo[2,3-d]pyrimidine (10.2)

Superhydride LiEt$_3$BH in 1M THF (8 mL, 10 eq.) was added dropwise to an ice-cold deoxygenated (after 15 min purging with argon) solution of anhydrous nucleoside 10.1 (218 mg, 0.8 mmol) in anhydrous THF (10 mL) under argon. The resulting mixture was stirred at 0° C. for 2 h, then acidified cautiously and finally purged with argon for 1 hr. The residue was purified on a silica gel column with 5% MeOH in CH$_2$Cl$_2$ to yield 117 mg of target compound 10.2 as off-white solid (yield 55%).

Example 10

Step C: 4-Methoxy-5-iodo-7-(3-deoxy-β-D-ribofurnaosyl)-7H-pyrrolo[2,3-d]pyrimidine (10.3)

To a solution of nucleoside 10.2 (350 mg, 1.32 mmol) in DMF (10 mL) was added N-iodosuccinimide (327 mg, 1.1 eq.) at 0° C. The reaction mixture was stirred at 0° C. under argon for 2 h, then warmed up to room temperature and stirred overnight. The reaction was quenched by addition of 4 mL of MeOH. The solution was evaporated to dryness, then redissolved in CHCl$_3$, washed with sat. aq. NaHCO$_3$, Na$_2$SO$_3$ and water, then dried over MgSO$_4$. After evaporation, the residue was purified on a silica gel column using 0-3% MeOH in CH$_2$Cl$_2$ to provide 353 mg of pure compound 10.3 as white solid (yield: 68%).

Example 10

Step D: 4-Amino-5-iodo-7-(3-deoxy-β-D-ribofurnaosyl)-7H-pyrrolo[2,3-d]pyrimidine (10.4)

A mixture of compound 10.3 (50 mg, 0.128 mmol) and anhydrous liquid ammonia (15 mL) was heated in a stainless steel autoclave at 120° C. 2 days, then cooled and evaporated in vacuo. The residue was purified on a silica gel column with 3% MeOH in CH$_2$Cl$_2$ as eluent to give 30 mg of the compound 10.4 as a white solid. (yield: 62%)

Example 10

Step E: 4-Amino-5-[2-(methoxycarbonyl)ethenyl]-7-(3-deoxy-β-D-ribofurnaosyl)-7H-pyrrolo[2,3-d]pyrimidine (10.5)

To a solution of compound 10.4 (50 mg, 0.132 mmol) in 2 mL of anhydrous DMF were added CuI (5 mg, 0.2 eq.), methyl acrylate (240 µL, 20 eq.), triethylamine (37 uL, 2 eq.) and Pd(PPh$_3$)$_4$ (15 mg, 0.1 eq.) at room temperature under an argon atmosphere. The reaction mixture was heated at 70° C. for 48 hr. then cooled to room temperature and 20 mL of 1/1 MeOH/CH$_2$Cl$_2$ was added. 100 mg Dowex 1×2-100 Bicarb form was then added and the suspension was stirred at room temperature for 45 min. then filtered. The resin was washed with 3×10 mL MeOH/CH$_2$Cl$_2$:1/1, and the solvent evaporated. DMF was finally evaporated by azeotropic co-evaporation with toluene (2×5 mL). The residue was purified by chromatographic column purification on silica gel (eluent: CH$_2$Cl$_2$/MeOH=95/5) to give 20 mg of final product 10.5 (yield 45%).

Example 10

Step F: 2-(3-Deoxy-β-D-ribofuranosyl)-2,6-dihydro-7H-2,3,5,6-tetraazabenzo[cd]azulen-7-one (10.6)

A solution of compound 10.5 (20 mg, 0.06 mmoles) in 0.1 M NaOMe in MeOH (12 mL) was heated at 70° C. for 4 hr. The solvent was evaporated and the residue purified by silica gel column with CH$_2$Cl$_2$/MeOH=90/10) to give the final product 10.6.

$^1$H NMR (300 MHz, CD$_3$OD): δ 8.31 (s, 1H,), 7.71 (s, 1H,), 7.05 (d, J 12 Hz), 6.05 (s, 1H, H-1'), 5.73 (d, J 12 Hz, 1H,), 3.87-3.66 (m, 4H, H-2', H-4' 2×H-5'), 2.31-2.09 (m, 1H, 2×H-3'); ES MS: 360.9 (M+CH$_3$COO).

Example 11

2-(2-C-Methyl-β-D-ribofuranosyl)-9-methyl-2,6-dihydro-7H-2,3,5,6-tetraazabenzo[cd]azulen-7-one (11.4)

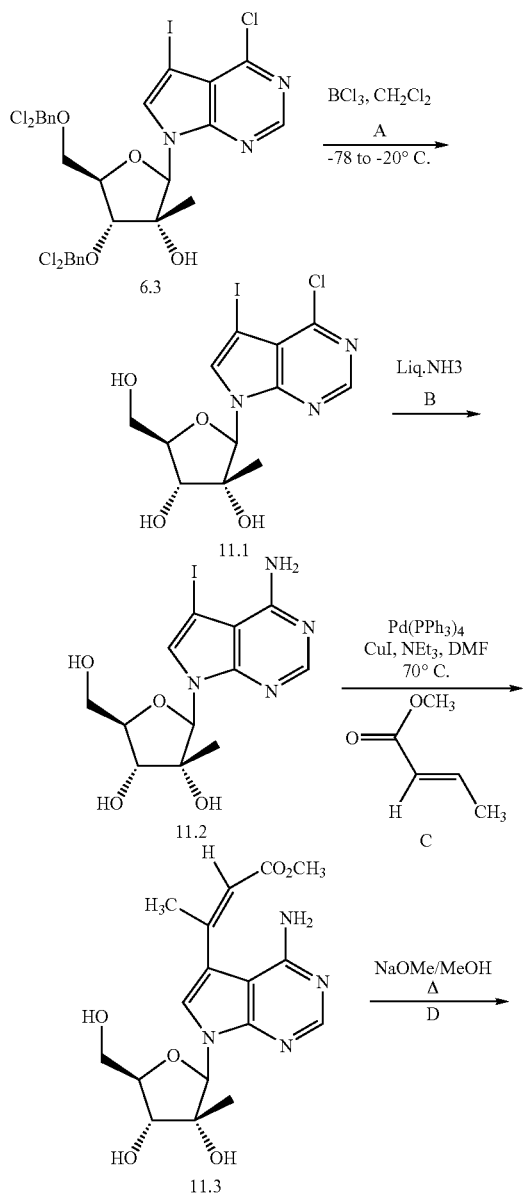

-continued

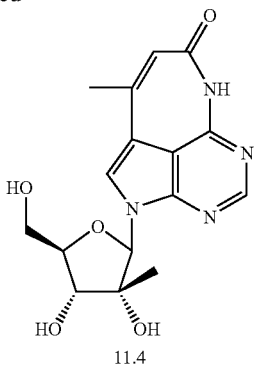

11.4

Example 11

Step A: 4-Chloro-5-iodo-7-(2-C-methyl-β-D-ribo-furnaosyl)-7H-pyrrolo[2,3-d]pyrimidine (11.1)

To a solution of the compound 6.3 (7.73 g, 10.39 mmoles) in dichloromethane (200 mL) at −78° C. was added boron trichloride (1M in dichloromethane, 104 mL, 104 mmol) dropwise. The mixture was stirred at −78° C. for 2.5 h, then at −30° C. to −20° C. for 3 hr. The reaction was quenched by addition of methanolic/dichloromethane (1:1) (105 mL) and the resulting mixture stirred at −15° C. for 30 min., then neutralized with aqueous ammonia at 0° C. and stirred at room temperature for 15 min. The solid was filtered and washed with $CH_2Cl_2$/MeOH (1/1, 250 mL). The chromatography over silica gel using $CH_2Cl_2$ and $CH_2Cl_2$/MeOH (99/1 to 90/10) gradient as the eluent to furnish the desired compound 11.1 (2.24 g, yield 51%) as a colorless foam.

Example 11

Step B: 4-Amino-5-iodo-7-(2-C-methyl-β-D-ribo-furnaosyl)-7H-pyrrolo[2,3-d]pyrimidine (11.2)

To the compound 11.1 (425 mg, 1 mmol) was added liquid ammonia (20 mL). The mixture was heated in a stainless steel autoclave at 85° C. overnight, then cooled and evaporated in vacuo. The crude mixture was purified on a silica gel column with 5% methanol in dichloromethane as eluent to give the product 11.2 as a light yellow foam (400 mg, 100% yield).

Example 11

Step C: 4-Amino-5-[1-methyl-2-(methoxycaronyl)ethenyl]-7-(2-C-methyl-β-D-ribofurnaosyl)-7H-pyrrolo[2,3-d]pyrimidine (11.3)

To a solution of compound 11.2 (1 g, 2.46 mmol) in 20 mL of anhydrous DMF were added CuI (94 mg, 0.2 eq.), methyl crotonate (5.33 mL, 20 eq.), triethylamine (686 μL, 2 eq.) and Pd(PPh$_3$)$_4$ (285 mg, 0.1 eq.) at room temperature under an argon atmosphere. The reaction mixture was heated at 70° C. for 24 hr. then cooled to room temperature and 100 mL of 1/1 MeOH/CH$_2$Cl$_2$ was added. 2.0 g Dowex 1×2-100 Bicarb form was then added and the suspension was stirred at room temperature for 45 min., then filtered. The resin was washed with 3×50 mL MeOH/CH$_2$Cl$_2$: 1/1. DMF was finally evaporated by azeotropic co-evaporation with toluene (2×5 mL). Chromatograph purification on silica gel (eluent: $C_{H2}Cl_2$/MeOH: 95/5) gave 463 mg of product 11.2 (yield: 50%).

Example 11

Step D: 2-(2-C-Methyl-β-D-ribofuranosyl)-9-methyl-2,6-dihydro-7H-2,3,5,6-tetraazabenz[cd]azulen-7-one (11.4)

A solution of compound 11.3 (33 mg, 0.087 mmoles) in 0.1 M NaOMe in MeOH (17 mL) was heated at 70° C. for 4 hr. The solution was evaporated and the residue purified by silica gel chromatography using CH$_2$Cl$_2$/MeOH:95/5 as eluent to provide 24 mg of final product 11.4 (yield 80%).

$^1$H NMR (300 MHz, DMSO-d$_6$) δ 10.66 (br. 1H, NH), 8.33 (s, 1H, H-4), 8.09 (s, 1H, H-1), 6.10 (s, 1H, H-1'), 5.67 (s, 1H, H-8), 5.16 (m, 3H, 3×OH), 4.05-3.65 (m, 4H, H-3', H-4' 2×H-5'), 2.11 (s, 3H, CH$_3$), 0.73 (s, 3H, CH$_3$); ESMS: 405.5 (M+CH$_3$COO).

Example 12

2-(2-C-Methyl-β-D-ribofuranosyl)-8-methyl-2,6-dihydro-7H-2,3,5,6-tetraazabenzo[cd]azulen-7-one (12.2)

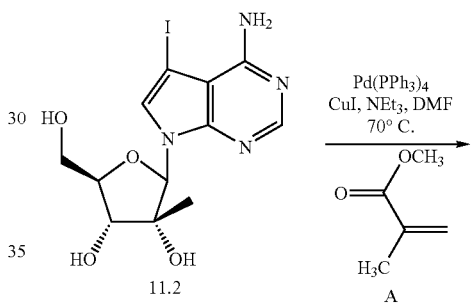

11.2

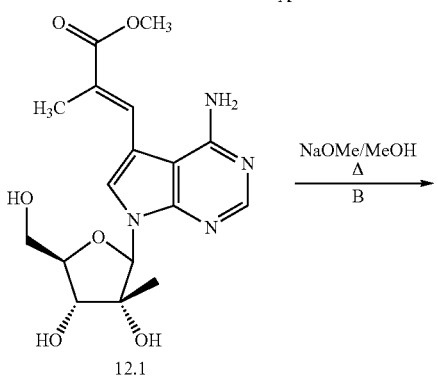

12.1

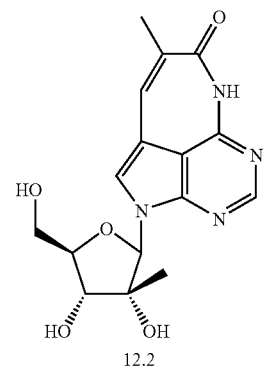

12.2

Example 12

Step A: 4-amino-5-[2-methyl-2-(methoxycaronyl)ethenyl]-7-(2-C-methyl-β-D-ribofurnaosyl)-7H-pyrrolo[2,3-d]pyrimidine (12.1)

To a solution of compound 11.2 (200 mg, 0.492 mmol) in 4 mL of anhydrous DMF was added CuI (19 mg, 0.2 eq.), α-methyl methacrylate (1.06 mL, 20 eq.), triethylamine (137 μL, 2 eq.) and Pd(PPh$_3$)$_4$ (57 mg, 0.1 eq.) at room temperature under an argon atmosphere. The reaction mixture was heated at 70° C. for 24 hr. then cooled to room temperature and 100 mL of 1/1 MeOH/CH$_2$Cl$_2$ was added. 400 mg Dowex 1×2-100 Bicarb form was then added the suspension stirred at room temperature for 45 min., then filtered. The resin was washed with 3×10 mL MeOH/CH$_2$Cl$_2$:1/1. DMF was finally evaporated by azeotropic co-evaporation with toluene (2×5 mL). Chromatograph purification of the residue on silica gel (eluent: CH$_2$Cl$_2$MeOH:95/5) gave 100 mg of ester 12.1 (yield: 54%).

Example 12

Step B: 2-(2-C-Methyl-β-D-ribofuranosyl)-8-methyl-2,6-dihydro-7H-2,3,5,6-tetraazabenzo[cd]azulen-7-one (12.2)

A solution of compound 12.1 (30 mg, 0.079 mmoles) in 0.1 M NaOMe in MeOH (16 mL) was heated at 70° C. for 4 hr. The solution was evaporated and the residue purified by silica gel column chromatography using CH$_2$Cl$_2$/MeOH:95/5) to provide product 12.2.

$^1$H NMR (300 MHz, DMSO-d$_6$) δ 10.60 (br s. 1H, NH), 8.28 (s, 1H, H-4), 7.73 (s, 1H, H-1), 7.09 (s, 1H, H-9), 6.07 (s, 1H, H-1'), 5.16 (m, 3H, 3×OH), 3.93-3.63 (m, 4H, H-3', H-4' 2×H-5'), 1.97 (s, 3H, CH$_3$), 0.72 (s, 3H, CH$_3$); ES MS: 405.3 (M+CH$_3$COO).

Example 13

2-(2-C-Methyl-β-D-ribofuranosyl)-9-methoxy-2,6-dihydro-7H-2,3,5,6-tetraazabenzo[c,d]azulen-7-one (13.2)

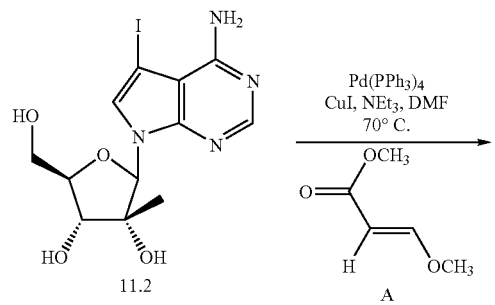

11.2

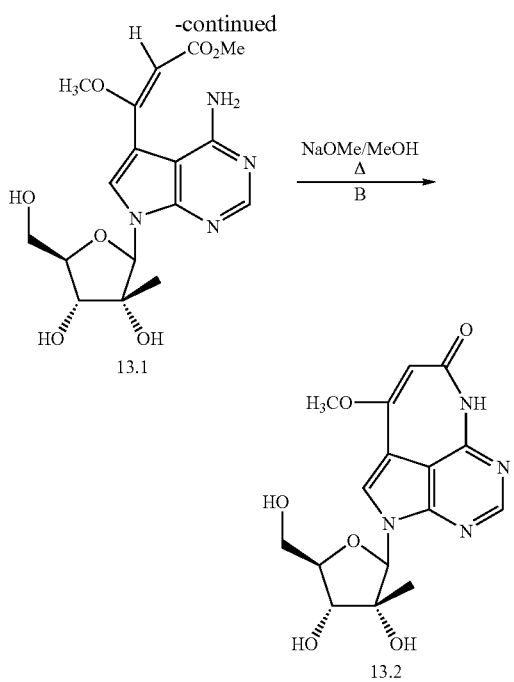

13.1

13.2

Example 13

Step A: 4-Amino-5-[1-methoxy-2-(methoxycaronyl)ethenyl]-7-(2-C-methyl-β-D-ribofurnaosyl)-7H-pyrrolo[2,3-d]pyrimidine (13.1)

To a solution of compound 11.2 (200 mg, 0.492 mmol) in 5 mL of anhydrous DMF were added CuI (19 mg, 0.2 eq.), E-3-methoxymethacrylate (1.06 mL, 20 eq.), triethylamine (137 μL, 2 eq.) and Pd(PPh$_3$)$_4$ (57 mg, 0.1 eq.) at room temperature under an argon atmosphere. The reaction mixture was heated at 70° C. for 24 hr. then cooled to room temperature and 100 mL of 1/1 MeOH/CH$_2$Cl$_2$ was added. 400 mg Dowex 1×2-100 Bicarb form was then added and the suspension stirred at room temperature for 45 min., then filtered. The resin was washed with 3×10 mL MeOH/CH$_2$Cl$_2$:1/1. DMF was finally evaporated by azeotropic co-evaporation with toluene (2×5 mL). Chromatographic purification of the residue on silica gel (eluent: CH$_2$Cl$_2$/MeOH:95/5) gave 87 mg of product 13.1 (yield: 45%).

Example 13

Step B: 2-(2-C-Methyl-β-D-ribofuranosyl)-9-methoxy-2,6-dihydro-7H-2,3,5,6-tetraazabenzo[cd]azulen-7-one (13.2)

A solution of compound 13.1 (30 mg, 0.076 mmoles) in 0.1 M NaOMe in MeOH (15 mL) was heated at 70° C. for 4 hr. The solution was evaporated and the residue purified by silica gel column with CH$_2$Cl$_2$/MeOH:95/5) to provide nucleoside 13.2.

$^1$H NMR (300 MHz, DMSO-d$_6$) δ 10.63 (br s 1H, NH), 8.35 (s, 1H, H-4), 8.06 (s, 1H, H-1), 6.13 (s, 1H, H-1'), 5.30 (s, 1H, H-8), 5.22 (m, 3H, 3×OH), 3.32 (s, 3H, OCH$_3$), 3.98-3.63 (m, 4H, H-3', H-4' 2×H-5'), 0.71 (s, 3H, CH$_3$); ES MS: 421.5 (M+CH$_3$COO$^-$).

Example 14

2-(2-C-Methyl-β-D-ribofuranosyl)-8-bromo-9-methoxy-2,6,8,9-tetrahydro-7H-2,3,5,6-tetraazabenzo[cd]azulen-7-one (14.1)

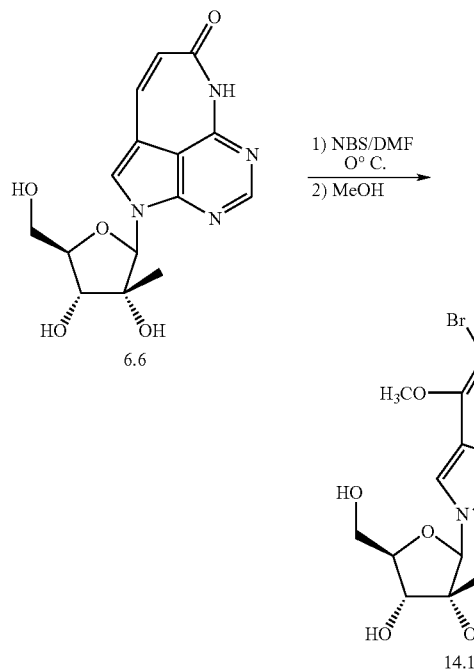

To a stirred solution of nucleoside 6.6 (10 mg, 0.030 mmol) in DMF (0.5 mL) was added N-bromosuccinimide (11.25 mg, 2.10 eq.) at 0° C. under argon. The reaction mixture was stirred at 0° C. for 1 hr then quenched with MeOH (0.5 mL). The mixture was evaporated to dryness and the residue was purified on a silica gel column with 5% MeOH in $CH_2Cl_2$ to give compound 14.1 as a mixture of diastereoisomers (8 mg, 65%). The isolated compound was characterized by $^1H$ NMR, COSY, NOESY and LCMS. $^1H$ NMR (300 MHz, DMSO-$d_6$) δ 11.29 (s, 1H, NH), 8.54 (s, 1H, H-4), 8.00 (s, 1H, H-1), 6.24, 6.21 (2s, 1H, H-1'), 5.22-5.08 (m, 4H, 3×OH, H-8), 4.77-4.73 (m, 1H, H-9), 3.95-3.7 (m, 4H, H-3', H-4' 2×H-5'), 3.24, 3.21 (2s, 3H, $OCH_3$), 0.68, 0.66 (2s, 3H, $CH_3$). ES MS: 501.7 ($M+CH_3COO^-$).

Example 15

4-Amino-2-(2-C-methyl-β-D-ribofuranosyl)-2,6-dihydro-7H-2,3,5,6-tetraazabenzo[cd]azulene-7-one (15.6)

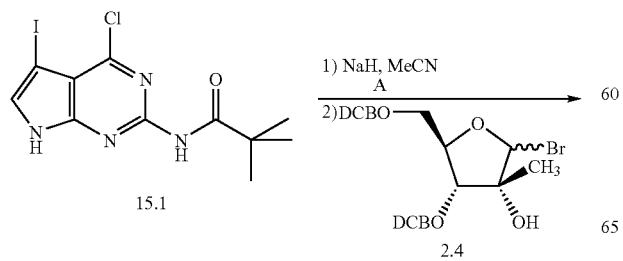

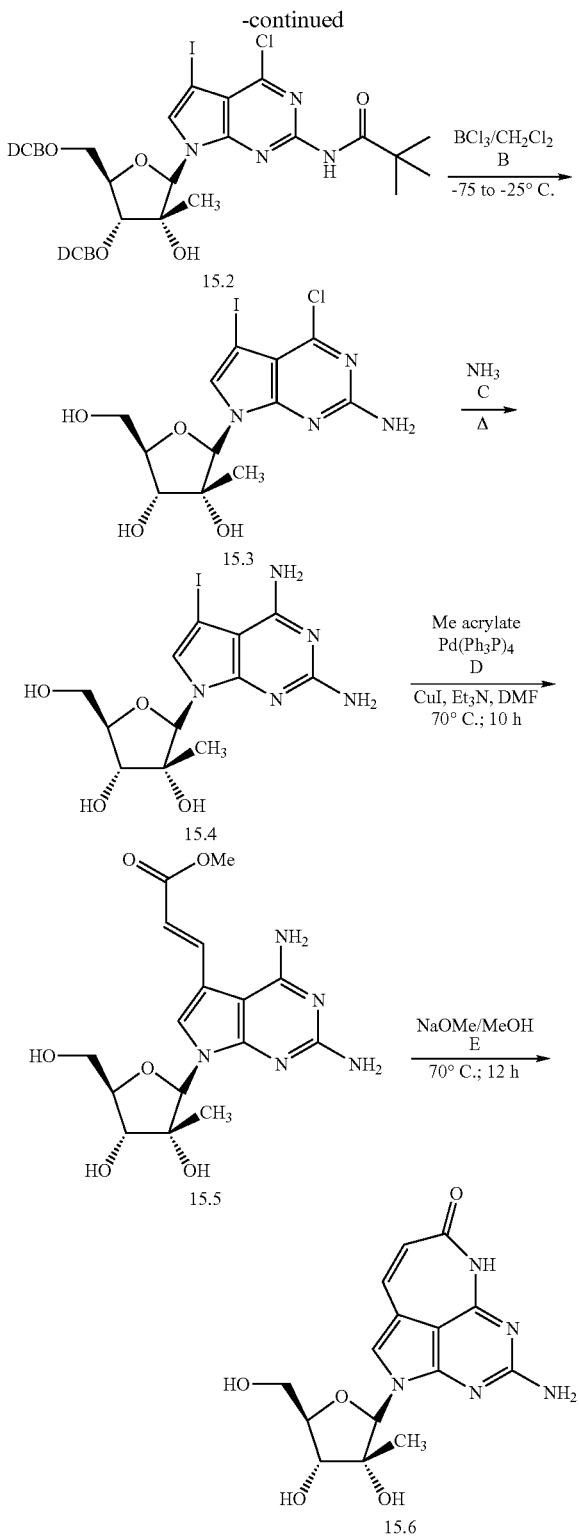

The sodium salt of 4-chloro-5-iodo-2-pivaloylamino-1H-pyrrolo[2,3-d]pyrimidine 15.1 (prepared in situ using sodium hydride) was reacted with protected 1-bromo-2-C-methyl-D-ribofuranose 2.4 (which was prepared with HBr/AcOH in $CH_2Cl_2$ from the corresponding 1-O-methyl analogue) to give the β-anomer 15.2. Removal of dichlorophenymethyl protecting groups was performed using boron trichloride in CH$_2$Cl$_2$ to give the 4-chloronucleoside 15.3. Further ammonolysis and deprotection at elevated temperature yielded 2,4-diamino nucleoside 15.4, which was converted under the Heck coupling conditions with methylacrylate into the corresponding 5-methylpropenoate 15.5. This compound was converted into the target tetraazabenzo[cd]azulene nucleoside 15.6 via sodium methoxide mediated ring closure.

Example 15

Step A: 4-Chloro-5-iodo-2-pivaloylamino-7-[3,5-bis-O-(2,4-dichlorophenymethyl)-2-C-methyl-β-D-ribofuranosyl]-7H-pyrrolo[2,3-d]pyrimidine (15.2)

A solution of 2.4 (36.7 mmol) in anhydrous acetonitrile (50 mL) was added to a solution of sodium salt of 4-chloro-5-iodo-2-pivaloylamino-7H-pyrrolo[2,3-d]pyrimidine in acetonitrile [generated in situ from 4-chloro-5-iodo-2-pivaloylamino-7H-pyrrolo[2,3-d]pyrimidine (*Nucl. Acid Res.* 1998 (26), 3350-3357) (20.87 g, 55.1 mmol) in anhydrous acetonitrile (1000 mL) and NaH (60% in mineral oil, 2.20 g, 55.1 mmol) after 4 hr of vigorous stirring at room temperature]. The combined mixture was stirred at room temperature for 48 hr. The solids were filtered then washed with acetonitrile (100 mL) and the combined filtrate evaporated to provide a viscous oil. Purification on a silica gel column, using hexanes/EtOAc gradient (15/1, 13/1, 11/1, 9/1, 7/1) as the eluent, yielded the target compound as a colorless foam (7.02 g, 23%).

Example 15

Step B: 4-Chloro-5-iodo-2-pivaloylamino-7-(2-C-methyl-β-D-ribofuranosyl)-7H-pyrrolo[2,3-d]pyrimidine (15.3)

To a solution of compound 15.2 (7.03 g, 8.43 mmol) in CH$_2$Cl$_2$ (200 mL) at −75° C. was added boron trichloride (1M in CH$_2$Cl$_2$; 83.4 mL, 83.4 mmol). The mixture was stirred at −75 to −70° C. for 2 hr and then at −30 to −20° C. for 3 hr. The reaction was quenched by addition of MeOH/CH$_2$Cl$_2$ (1/1, 9 mL) and the resulting mixture stirred at −20 to −15° C. for 30 min., then neutralized with aq. ammonia (28%, 35 mL) at 0° C. and stirred at room temperature for 10 min. The solid which separated was filtered and washed with MeOH/CH$_2$Cl$_2$ (1/1, 500 mL). The combined filtrates were evaporated and the residue was purified on a silica gel column using CH$_2$Cl$_2$/MeOH (50/1, 40/1) as the eluents to furnish the target compound 15.3 as an off-white solid (2.93 g, 80%).

Example 15

Step C: 2,4-Diamino-5-iodo-7-(2-C-methyl-β-D-ribofuranosyl)-7H-pyrrolo[2,3-d]pyrimidine (15.4)

A mixture of the compound from Step B (2.92 g 5.6 mmol) and anhydrous liquid ammonia (50 mL) was heated in a stainless steel autoclave at 110° C. for 1 d, then cooled and the solvent evaporated. The residue was treated with MeOH to yield 0.30 g of 15.4. The filtrate was evaporated and purified on silica gel column with CH$_2$Cl$_2$/MeOH (20/1) to furnish additional 1.52 g of the target compound (total yield 77%).

Example 15

Step D: 2,4-Diamino-5-[(E)-1-(methoxycarbonyl)-2-ethenyl]-7-(2-C-methyl-β-D-ribofuranosyl)-7H-pyrrolo[2,3-d]pyrimidine (15.5)

To a solution of the compound from Step C (1.54 g, 3.66 mmol) in DMF (35 mL) were added copper iodide (139 mg, 0.73 mmol), methyl acrylate (6.6 mL, 73.1 mmol), triethylamine (1.02 mL, 7.3 mmol), and tetrakis(triphenylphosphine)palladium [0] (422.5 mg, 0.37 mmol). The resulting mixture was stirred at 70° C. for 10 h, then cooled to room temperature and diluted with MeOH/CH$_2$Cl$_2$ (1/1, 50 mL). Dowex HCO$_3^-$ (3 g) was added then and after 45 min of stirring, the resin was filtered off, washed with CH$_2$Cl$_2$/MeOH (1/1, 150 mL) and the combined filtrates concentrated. The residue was treated with MeOH and the catalyst, which separated, was filtered off. The evaporated filtrate was treated with MeOH again and the target compound, which separated, was filtered off (627 mg). The filtrate was concentrated in vacuo, and purified on a silica gel column using a CH$_2$Cl$_2$/MeOH gradient (50/1, 30/1, 20/1 and 15/1) to furnish an additional 175 mg of compound 15.5 (total yield 58%).

Example 15

Step E: 4-Amino-2-(2-C-methyl-β-D-ribofuranosyl)-2,6-dihydro-7H-2,3,5,6-tetraazabenzo[cd]azulene-7-one (15.6)

A solution of the compound from Step D (578 mg, 1.52 mmol) in 0.1 N NaOMe/MeOH (250 mL) was heated at 60° C. for 12 hr and then neutralized at room temperature with Dowex H$^+$. The resin was filtered, washed with MeOH and the combined filtrates concentrated in vacuo. Purification on a silica gel column with CH$_2$Cl$_2$/MeOH (10/1 and 5/1) yielded the target compound 15.6 as a yellow solid (245 mg, 46%).

$^1$H-NMR (DMSO-d$_6$): δ 10.04 (br s, NH, 1H), 7.42 (s, 1H, H-1), 6.90 (d, H-9, J 11.7 Hz, 1H), 6.26 (br, NH$_2$, 2H), 5.91 (s, H-1', 1H), 5.56 (dd, J 11.7 Hz, J 1.6 Hz, H-8, 1H), 5.21 (br s, 3'-OH, 1H), 5.06 (t, J 4.8 Hz, 5'-OH, 1H), 4.98 (s, 2'-OH, 1H), 3.75-3.88 (m, H-3', H-4', H-5', 3H), 3.62 (m, H-5',1H), 0.78 (s, Me, 3H). MS m/z=406.5 (M+CH$_3$COO$^-$).

Example 16

4-Fluoro-2-(2-C-methyl-β-D-ribofuranosyl)-2,6-dihydro-7H-2,3,5,6-tetraazabenzo[cd]azulene-7-one (16.2)

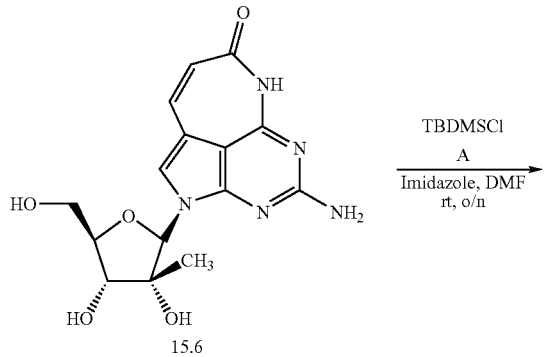

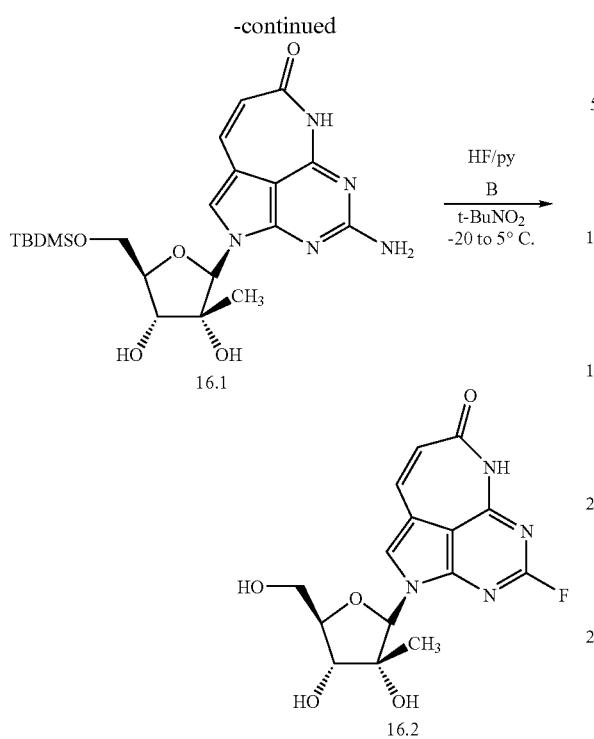

Nucleoside 15.6 was converted with HF in pyridine and tert-butylnitrite at low temperature into the corresponding 4-fluoro analogue 16.2, after 5'-O-tert-butyldimethylsilyl derivatization with tert-butyldimethylsilyl chloride and imidazole in DMF.

Example 16

Step A: 4-Amino-2-(5-O-tert-butyldimethylsilyl-2-C-methyl-β-D-ribofuranosyl)-2,6-dihydro-7H-2,3,5,6-tetraazabenzo[cd]azulene-7-one (16.1)

A mixture of 4-amino-2-(2-C-methyl-β-D-ribofuranosyl)-2,6-dihydro-7H-2,3,5,6-tetraazabenzo[cd]azulene-7-one (65 mg, 0.19 mmol) in DMF, tert-butyldimethylsilyl chloride (70 mg, 0.45 mmol) and imidazole (61 mg, 0.90 mmol) was stirred overnight at room temperature and then concentrated in vacuo. The oily residue was dissolved in $CH_2Cl_2$ (20 mL), washed with aq. HCl (0.1 N), sat.aq. $NaHCO_3$, water, brine and dried ($Na_2SO_4$). The evaporated residue was purified on silica gel with hexanes/EtOAc (1/1)+0.5% $Et_3N$ and EtOAc+0.5% $Et_3N$ to yield the target compound 16.1 as colorless oil (38 mg, 44%).

Example 16

Step B: 4-Fluoro-2-(2-C-methyl-β-D-ribofuranosyl)-2,6-dihydro-7H-2,3,5,6-tetraazabenzo[cd]azulene-7-one (16.2)

To a solution of HF/pyridine (1.5 mL) and pyridine (1 mL) at −25° C. was added a solution of 16.1 (30 mg, 0.07 mmol) in pyridine (0.5 mL) followed by tert-butylnitrite (15 μL, 0.13 mmol). Reaction mixture was allowed to warm to −5° C., quenched with 6 N aq. NaOH and evaporated. The pale-yellow residue was triturated with MeOH, filtered and thoroughly washed with MeOH (100 mL combined filtrate).

The evaporated filtrate was purified on a silica gel column with $CH_2Cl_2$/MeOH 20/1 to give the target compound 16.2 as a yellow solid (5 mg, 22%).

$^1$H-NMR ($CD_3OD$): δ 7.05 (d, H-9, $J_{H8,H9}$=11.7 Hz, 1H), 7.81 (s, 1H, H-1), 6.09 (s, H-1', 1H), 5.78 (d, $J_{H8,H9}$ 11.7 Hz, H-8, 1H), 3.99-4.10 (m, H-3', H-4', H-5', 3H), 3.85 (dd, $J_{gem}$ 12.9 Hz, $J_{H5',H4'}$ 3.5 Hz, H-5',1H), 0.92 (s, Me, 3H). $^{19}$F-NMR ($CD_3OD$): δ −52.58. MS m/z=409.6 (M+$CH_3COO^-$).

Example 17

7-Amino-2-(2-C-methyl-β-D-ribofuranosyl)-2H-2,3,5,6-tetraazabenzo[cd]azulene (17.2)

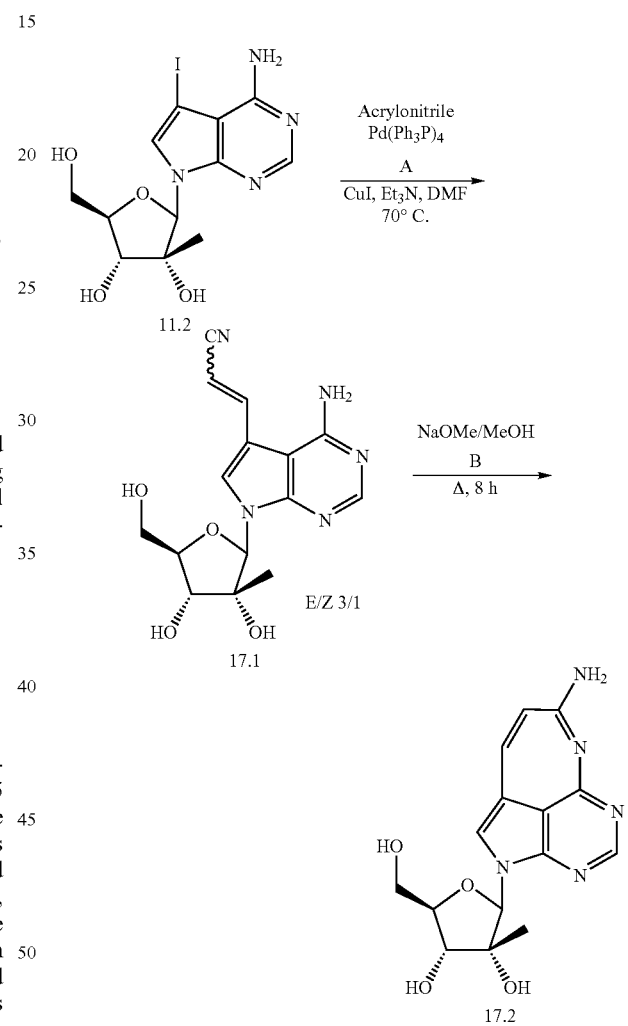

Nucleoside 11.2 was reacted with acrylonitrile under Heck-type coupling conditions. The nitrile 17.1 was converted into the target 7-amino-tetraazabenzoazulen nucleoside 17.2 via sodium methoxide mediated ring closure.

Example 17

Step A: 4-Amino-5-[(E/Z)-1-cyano-2-ethenyl]-7-(2-C-methyl-β-D-ribofuranosyl)-7H-pyrrolo[2,3-d]pyrimidine (17.1)

To a solution of 11.2 (200 mg, 0.49 mmol) in DMF (5 mL) were added copper iodide (19 mg, 0.1 mmol), acrylonitrile (0.65 mL, 9.8 mmol), triethylamine (0.137 mL, 0.99 mmol), and tetrakis(triphenylphosphine)palladium [0] (57 mg, 0.05 mmol). The resulting mixture was stirred at 70° C. for 4 d., then cooled to room temperature, diluted with MeOH/CH$_2$Cl$_2$ (1/1, 6 mL), and treated with Dowex HCO$_3$⁻ (0.5 g). After 1 hr stirring the resin was filtered off, washed with CH$_2$Cl$_2$/MeOH (1/1, 50 mL) and combined filtrate concentrated. The crude residue was purified on a silica gel column with a CH$_2$Cl$_2$/MeOH gradient (50/1, 30/1, 10/1) to yield the target stereoisomeric mixture (B/Z, 3/1) as yellow solid (75 mg, 46%).

Example 17

Step B: 7-Amino-2-(2-C-methyl-β-D-ribofuranosyl)-2H-2,3,5,6-tetraazabenzo[cd]azulene (17.2)

A mixture of the compound from Step A (75 mg, 0.23 mmol) in 0.1 N NaOMe/MeOH (18 mL) was heated at 60° C. for 8 hr then cooled to room temperature and evaporated in vacuo. Crude residue was purified on a silica gel column with a CH$_2$Cl$_2$/MeOH gradient (20/1, 10/1, 5/1) to yield the target compound 17.2 as yellow solid (44 mg, 59%).

$^1$H-NMR (DMSO-d$_6$): δ 8.10 (s, H-4, 1H), 7.51 (s, 1H, H-1), 7.6-8.0 (2br, NH$_2$, 2H), 6.85 (d, H-9, J$_{H8,H9}$=11.6 Hz, 1H), 6.01 (s, H-1', 1H), 5.52 (d, H-8, J$_{H8, H9}$, 11.6 Hz, 1H), 5.11 (m, 2'-OH, 3'-OH, 5'-OH), 3.77-3.91 (m, H-3', H-4', H-5', 3H), 3.63 (m, H-5',1H), 0.70 (s, Me, 3H). MS m/z=390.8 (M+CH$_3$COO⁻).

Example 18

7-Methoxy-2-(2-C-methyl-β-D-ribofuranosyl)-2H-2,3,5,6-tetraazabenzo[cd]azulene (18.3)

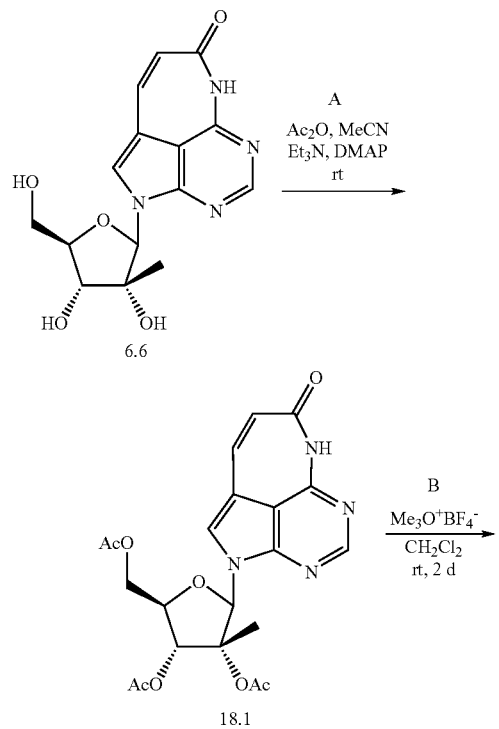

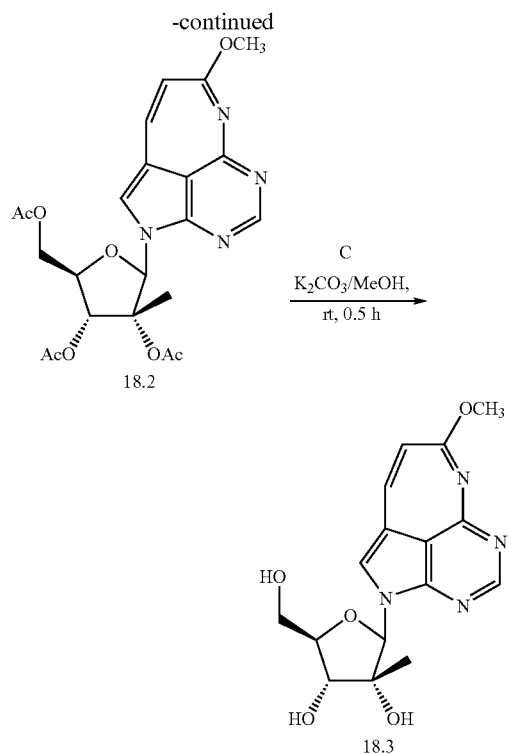

Peracetylated nucleoside 18.1, prepared by treating the compound 6.6 with acetic anhydride, triethylamine and DMAP in acetonitrile and was reacted with trimethyloxonium tetrafluoroborate in CH$_2$Cl$_2$ at ambient temperature to furnish methoxy nucleoside 18.2. Removal of acetyl groups in MeOH saturated with potassium carbonate yielded the target nucleoside 18.3.

Example 18

Step A: 2-(2,3,5-Tri-O-acetyl-2-C-methyl-β-D-ribofuranosyl)-2,6-dihydro-7H-2,3,5,6-tetraazabenzo[cd]azulene-7-one (18.1)

To a solution of 2-(2-C-methyl-β-D-ribofuranosyl)-2,6-dihydro-7H-2,3,5,6-tetraazabenzo[cd]azulene-7-one 6.6 (136 mg, 0.41 mmol) in acetonitrile were added acetic anhydride (0.71 mL, 7.5 mmol), triethylamine (1.05 mL), and DMAP (58 mg, 0.47 mmol). The mixture was stirred overnight at room temperature, then evaporated and the residue partitioned between water (75 mL) and CH$_2$Cl$_2$ (200 mL). The organic layer was washed with brine and dried over Na$_2$SO$_4$. The evaporated residue was treated with MeOH to yield the target compound as yellow solid (150 mg, 80%).

Example 18

Step B: 7-Methoxy-2-(2,3,5-tri-O-acetyl-2-C-methyl-β-D-ribofuranosyl)-2H-2,3,5,6-tetraazabenzo[cd]azulene-7-one (18.2)

A solution of the compound from Step A (50 mg, 0.11 mmol) in CH$_2$Cl$_2$ (1 mL) and trimethoxyoxonium tetrafluoroborate (18 mg, 0.12 mmol) under argon was stirred at room temperature for 2 d. At this point the reaction was quenched with sat. aq. K$_2$CO$_3$ (1 mL) and the resulting mixture diluted with CH$_2$Cl$_2$ (50 mL), washed with water, brine and dried over Na$_2$SO$_4$. The evaporated residue was purified on a silica gel column with CH$_2$Cl$_2$/MeOH (50/1) as the eluent to yield the target compound 18.2 as yellow solid (29 mg, 56%).

Example 18

Step C: 7-Methoxy-2-(2-C-methyl-β-D-ribofuranosyl)-2H-2,3,5,6-tetraazabenzo[cd]azulene (18.3)

A mixture of the compound from Step B (28 mg, 0.06 mmol) in saturated methanolic K$_2$CO$_3$ (5 mL) was stirred at room temperature for 30 min. and then concentrated in vacuo. The crude evaporated residue was purified on a silica gel column with CH$_2$Cl$_2$/MeOH (20/1) as the eluent to afford the target compound 18.3 (15 mg, 72%) as a yellow solid.

$^1$H-NMR (DMSO-d$_6$): δ 8.30 (s, H-4, 1H), 7.68 (s, 1H, H-1), 6.83 (d, H-9, J$_{H8,H9}$ 11.6 Hz, 1H), 5.98 (s, H-1', 1H), 5.84 (d, H-8, J$_{H8,H9}$ 11.4 Hz, 1H), 5.22 (s, 2'-OH, 1H), 5.17 (m, 3'-OH, 1H), 5.12 (t, 5'-OH, J$_{5'OH,H5'}$ 5.0 Hz, 1H), 3.78-3.88 (m, H-3', H-4', H-5', 3H), 3.65 (m, H-5',1H), 3.49 (s, OMe, 3H), 0.72 (s, Me, 3H). MS m/z=405.9 (M+CH$_3$COO$^-$).

Example 19

2-(2-C-Methyl-β-D-ribofuranosyl)-2H-2,3,5,6-tetraazabenzo[cd]azulene-4,7(3H,6H)-dione (19.1)

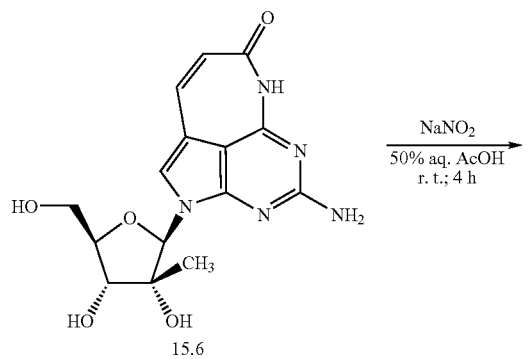

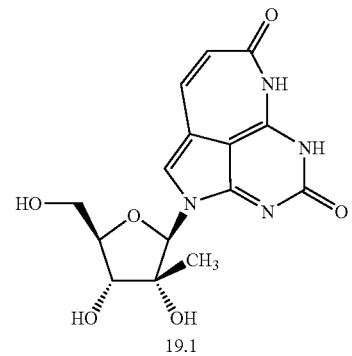

19.1

To a solution 4-amino-2-(2-C-methyl-β-D-ribofuranosyl)-2,6-dihydro-7H-2,3,5,6-tetraazabenzo[cd]azulene-7-one 15.6 (35 mg, 0.1 mmol) in 50% aqueous acetic acid (5 mL) was added sodium nitrite (42 mg, 0.6 mmol) and the mixture stirred at room temperature for 4 hr. The mixture was neutralized with 1M TEAB buffer and purified by reversed phase ion-pairing HPLC on a Phenomenex Luna C18(2) 250×21 mm 10 μm column. 100 mM triethylammonium acetate (TEAA), pH 7 was used as the ion-pairing agent. A gradient of 20% to 55% MeOH over 40 min was applied. The target compound eluted at 26 min followed by two smaller peaks at 29 and 31 min. TEAA was removed by repeated lyophilzation to yield the target compound as a fluffy yellow material (28 mg, 80%).

$^1$H-NMR (DMSO-d$_6$): δ 11.0 (br s, 2NH, 2H), 7.53 (s, 1H, H-1), 6.95 (d, H-9, J$_{H8,H9}$ 11.7 Hz, 1H), 5.91 (s, H-1', 1H), 5.62 (d, J$_{H8,H9}$ 11.7 Hz, H-8, 1H), 5.10 (br, 5'-OH, 3'-OH, 2'-OH, 3H), 3.77-3.89 (m, H-3', H-4', H-5', 3H), 3.63 (m, H-5',1H), 0.79(s, Me, 3H). MS m/z 347.7 (M-1).

Example 20

4-Chloro-2-(2-C-methyl-β-D-ribofuranosyl)-2,6-dihydro-7H-2,3,5,6-tetraazabenzo[cd]azulen-7-one (20.8)

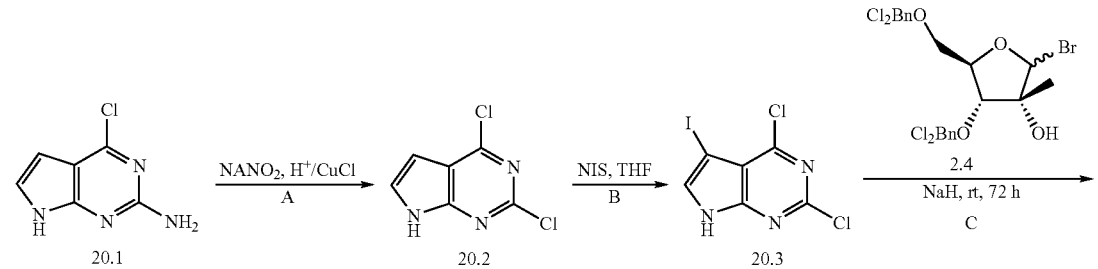

-continued

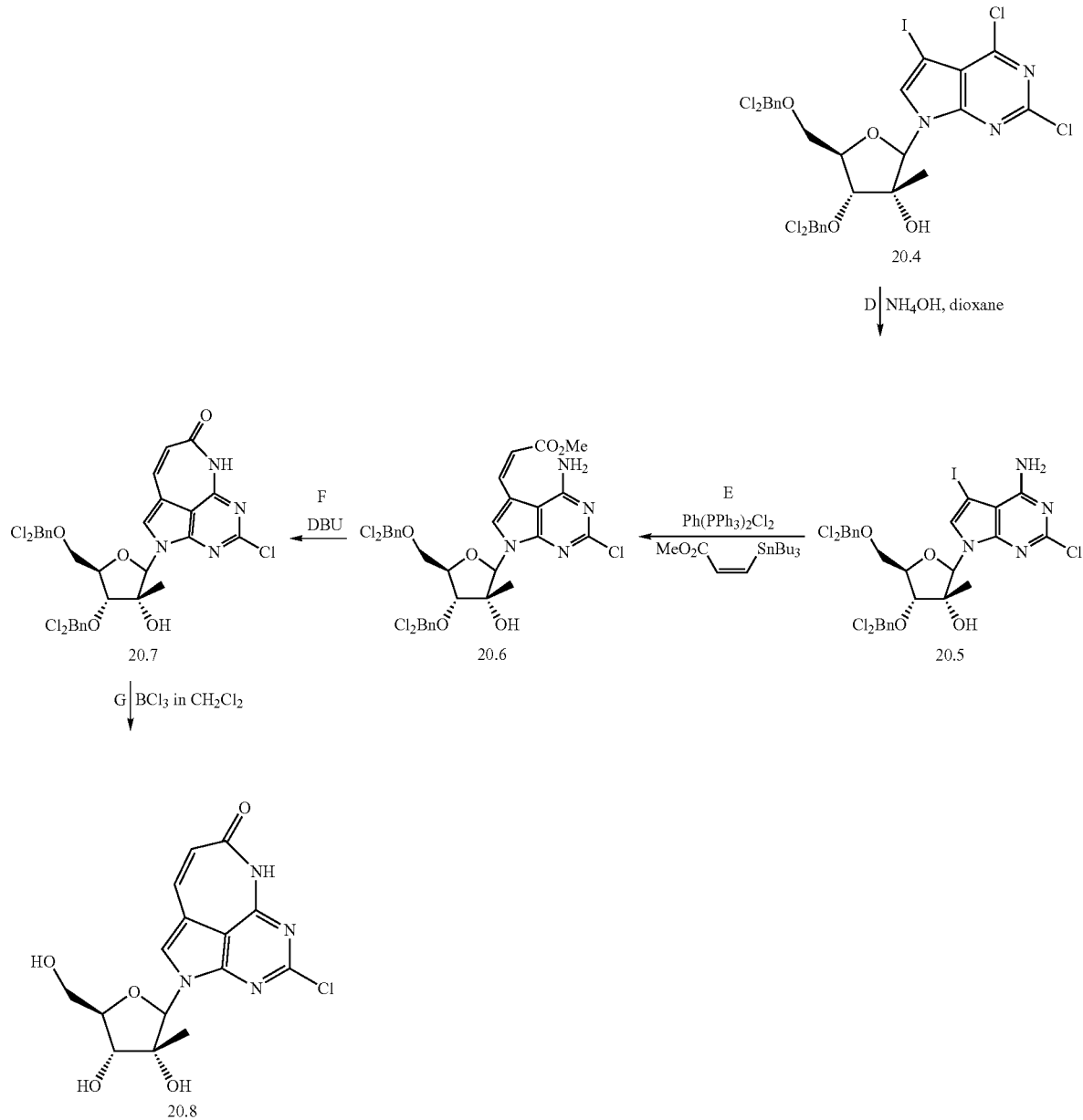

The tricyclic nucleoside 20.8 was synthesized starting from 2-amino-4-chloro-7H-pyrrolo[2,3-d]pyrimidine 20.1. The nucleobase 20.1 was diazotized in the presence of copper chloride and the resulting base 2,4-dichloro-7H-pyrrolo[2,3-d]pyrimidine was treated with N-iodosuccinimide in THF at room temperature to provide 2,4-dichloro-5-iodo-7H-pyrrolo[2,3-d]pyrimidine 20.3. Then 20.3 was converted to the corresponding sodium salt with sodium hydride in acetonitrile and reacted with bromo-sugar 2.4, which was prepared from 3,5-bis-O-(2,4-dichlorophenylmethyl)-2-C-methyl-1-O-methyl-α-D-ribofuranose ((i)*Helv. Chim. Acta.* 1995, 78, 486; (ii) WO 02/057287, 2002), to give nucleoside 20.4. The glycosylation product 20.4 was allowed to react with ammonium hydroxide in dioxane at 100° C. provided 20.5. Methyl-cis-β-(tributylstannyl)acrylate (*J. Am. Chem. Soc*; 1993, 115, 1619) was coupled with compound 20.5 under Stille reaction conditions using $PdCl_2(PPh_3)_2$ and copper iodide to give Z-ester analog 20.6, which was further reacted with DBU in dioxane to give protected tricycle 20.7. Nucleoside 20.7 was treated with boron trichloride in $CH_2Cl_2$ to afford tricyclic nucleoside 20.8.

Example 20

Step A: 2-Amino-4-chloro-5-iodo-1H-pyrrolo[2,3-d] pyrimidine (20.2)

Compound 20.2 was prepared as described in Seela, F., at al., *Liebigs Ann. Chem.*, 1985, 312-320.

Example 20

Step B: 2,4-Dichloro-5-iodo-1H-pyrrolo[2,3-d]pyrimidine (20.3)

Compound 20.2 (3.80 g, 20.0 mmol) was dissolved in THF (200 mL) and cooled to −20° C. for 20 min. N-Iodosuccinimide (7.0 g, 30.0 mmol) was slowly added and the resulting mixture was stirred at room temperature. After 2 h, the mixture was evaporated to dryness and the residue was re-dissolved in ethyl acetate, washed with 5% sodium thiosulphate, saturated sodium chloride solution and then dried over sodium sulfate and evaporated to dryness. The crude product was purified by silica gel column chromatography using 20% ethyl acetate in hexane to give 4.6 g of compound 20.3 as a yellowish solid.

Example 20

Step C: 2,4,-Dichloro-5-iodo-7-[3,5-bis-O-(2,4-dichlorophenylmethyl)-2-C-methyl-β-D-ribofuranosyl]-7H-pyrrolo[2,3-d]pyrimidine (20.4)

A solution of 2.4 ((i) *Helv. Chim. Acta.* 1995, 78, 486; (ii) WO 02/057287, 2002) (8.8 g, 20.0 mmoles) in anhydrous acetonitrile (300 mL) was added to a solution of the sodium salt of 4,6-dichloro-5-iodo-7H-pyrrolo[2,3-d]pyrimidine [generated in situ from 4,6-dichloro-5-iodo-7H-pyrrolo[2,3-d]pyrimidine (3.1 g, 10.0 mmol) in anhydrous acetonitrile (100 mL), and NaH (60% in mineral oil, 0.90 g, 37.0 mmol), after 4 hr of vigorous stirring at room temperature]. The combined mixture was stirred at room temperature for 40 hr, and then evaporated to dryness. The mixture was filtered through a celite plug and the solid residue was thoroughly washed with 500 mL of acetonitrile. The filtrates were evaporated to dryness and the crude product was purified on a silica gel column using 25% ethyl acetate in hexane to give 2.8 g of the desired product 20.4 as a white foam.

Example 20

Step D: 4,2-Dichloro-5-iodo-7-[3,5-bis-O-(2,4-dichlorophenylmethyl)-2-C-methyl-β-D-ribofuranosyl]-7H-pyrrolo[2,3-d]pyrimidine (20.5)

The material from Step C (2.5 g, 2.5 mmol) in dioxane (50 mL) was placed in a pressure vessel and aqueous ammonium hydroxide (50 mL) was added. The mixture was tightly sealed and heated to 100° C. for 2 hr. After the reaction, the mixture was evaporated to dryness and the crude product was purified using silica gel column chromatography with 5-10% MeOH in $CH_2Cl_2$ as eluent to give 2.10 g of the pure desired product 20.5.

Example 20

Step E: 4-Amino-2-chloro-5-[1-(methoxycarbonyl)-2-ethenyl]-7-[3,5-bis-O-(2,4-dichlorophenylmethyl)-2-C-methyl-β-D-ribofuranosyl]-7H-pyrrolo[2,3-d]pyrimidine (20.6)

To the material from Step D (2.1 g, 1.90 mmol) in 100 mL of anhydrous DMF was added CuI (83.80 mg, 0.44 mmol), methyl-cis-β-(tributylstannyl)acrylate (1.5 mL, 4.4 mmol) and $PdCl_2(PPh_3)_2$ (150.0 mg, 0.22 mmol) at room temperature under an argon atmosphere. The reaction mixture was heated at 70° C. for 24 hr then cooled to room temperature and filtered through a celite plug. The filtrate was evaporated to dryness and the crude product purified on a silica gel column using 5-30% THF in $CH_2Cl_2$ as eluent to give 2.2 g of pure the desired ester 20.6.

Example 20

Step F: 2-[3,5-Bis-O-(2,4-dichlorophenylmethyl)2-C-methyl-β-D-ribofuranosyl]-4-chloro-2,6-dihydro-7H-2,3,5,6-tetraazabenzo[cd]azulen-7-one (20.7)

To a solution of compound 20.6 (1.9 g, 2.5 mmol) in dioxane (40 mL) was added DBU (1.3 mL, 9.0 mmol). The mixture was heated at reflux for 2 hr and then evaporated to dryness. The crude product was purified by silica gel column chromatography using 5-10% MeOH in $CH_2Cl_2$ as eluent to give 1.7 g of pure product 20.7.

Example 20

Step G: 4-Chloro-2-(2-C-methyl-β-D-ribofuranosyl)-2,6-dihydro-7H-2,3,5,6-tetraazabenzo[cd]azulen-7-one (20.8)

To a solution of compound 20.7 obtained from Step F (1.7 mg, 2.4 mmol) in $CH_2Cl_2$ (200 mL) at −78° C. was added boron trichloride (1M in $CH_2Cl_2$, 25 mL, 25.0 mmol), dropwise. The mixture was stirred at −78° C. for 2.5 hr, then at −30° C. to −20° C. for 3 hr. The reaction was quenched by addition of MeOHic/$CH_2Cl_2$ (1:1) (50 mL) and the resulting mixture stirred at −15° C. for 30 minutes, then neutralized with aqueous ammonia at 0° C. and stirred at room temperature for 15 minutes. The mixture was evaporated to dryness and the residue was purified by silica gel column chromatography using 5-20% ethanol in $CH_2Cl_2$ as eluent to give 560 mg of pure yellowish tricyclic product 20.8.

$^1$H NMR (DMSO-$d_6$) δ 11.04 (d, J 1.5 Hz, 1H, NH), 7.89 (s, 1H, H-6), 7.04 (d, J 11.7 Hz, H1"), 5.96 (s, 1H, H-1'), 5.69 (dd, J 11.7, 1,5 Hz, H2"), 5.16 (m, 3H, 3×OH), 3.88-3.32 (m, 4H, H-3', H-4', 2×H-5'), 0.76 (s, 3H, $CH_3$).

Tricyclic nucleoside 20.8 was found to be a suitable intermediate for the synthesis of C-4-functionalized tricyclic nucleosides. Nucleoside 20.8 was reacted with sodium thiomethoxide in DMF at elevated temperature. Two products were isolated in a ratio of 1:1. These products were separated using reverse phase HPLC and characterized as tricyclic nucleosides 21.1 and 21.2 using $^1$H NMR and LCMS analysis. Compound 20.8 was treated with tert-butyldimethylsilyl chloride and imidazole in DMF at room temperature to give 5'-TBDMS protected tricylic nucleoside 21.3. Nucleophilic displacement reaction of compound 21.3 using 2M methylamine in THF, followed by deprotection reaction using tetrabutylammoniumfluoride (TBAF) afforded 4-methylamino derivative 21.4. In a similar fashion, 21.3 was reacted with sodium methoxide in MeOH at reflux and the resulting product was deprotected with TBAF to give 4-OMe analog 21.5.

Examples 21 and 22

2-(2-C-methyl-β-D-ribofuranosyl)-4-methylthio-2,6-dihydro-7H-2,3,5,6-tetraazabenzo[cd]azulen-7-one (21.1) and 2-(2-C-methyl-β-D-ribofuranosyl)-4,9-di(methylthio)-2,6,8,9-tetrahydro-7H-2,3,5,6-tetraazabenzo[cd]azulen-7-one (21.2)

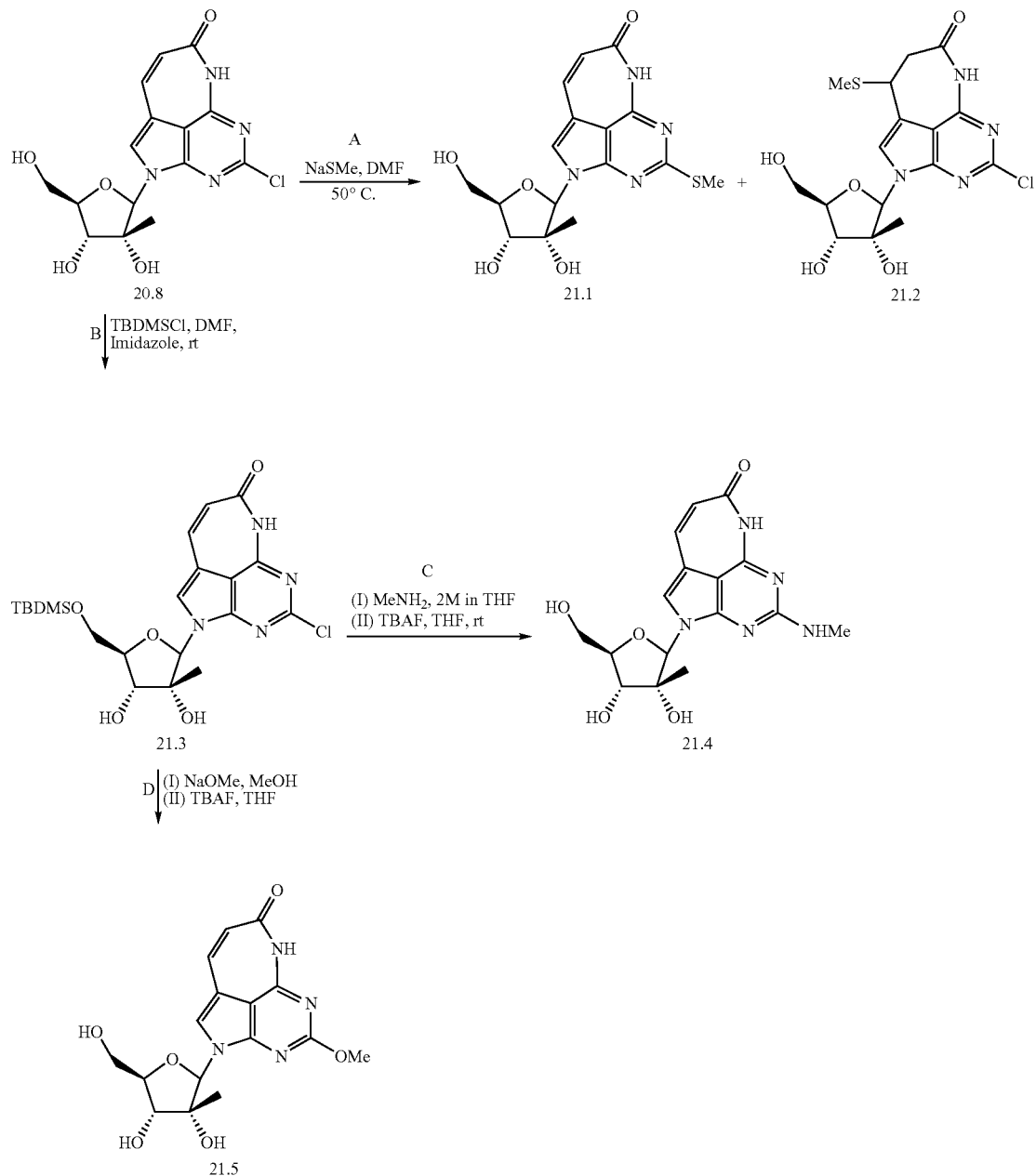

To a solution of the compound obtained from Example 20 (20.8) (100.0 mg, 0.30 mmol) in DMF (10 mL) was added sodium thiomethoxide (105 mg, 1.5 mmol). The mixture was stirred at 120° C. for 24 hr. After evaporation of the DMF under reduced pressure, the residue was purified on a silica gel column using 5-12% MeOH in CHCl$_3$ to give a mixture of two products (1:1). These two products were separated by reverse phase HPLC to give 25 mg of 21.1 and 30 mg of 21.2.

For Example 21 (21.1): $^1$H NMR (CD$_3$OD) δ 7.70 (s, 1H, H-6), 7.00 (d, J 12.0 Hz, H1″), 6.19 (s, 1H, H-1'), 5.72 (d, J 12.0 Hz, H2″), 4.07-3.80 (m, 4H, H-3', H-4', 2×H-5'), 2.56 (s, 3H, SCH$_3$), 0.91 (s, 3H, CH$_3$).

For Example 22 (21.2): $^1$H NMR (CD$_3$OD) δ 7.54 (s, 1H, H-6), 6.29 (s, 1H, 2×H1'), 4.51-3.79 (m, 5H, H-3', H-4', 2×H-5', CH), 3.21 (m, 2H, CH₂), 2.59 (s, 3H, SCH₃), 2.14 (2×s, 3H, SCH₃), 0.88 (2×s, 3H, 2×CH₃).

Example 23

2-(2-C-M 4-β-D-ribofuranosyl)-4-methylamino-2,6-dihydro-7H-2,3,5,6-tetraazabenzo[cd]azulen-7-one (21.4)

4-Chloro-2-(5-O-tert-butyldimethylsiliyl-2-C-methyl-β-D-ribofuranosyl)-2,6-dihdro-7H-2,3,5,6-tetraazabenzo[cd]azulen-7-one (21.3)

To a solution of compound 20.8 (366 mg, 1.0 mmol) and imidazole (68.0 mg, 1.0 mmol) in DMF (20 mL) was added tert-butyldimethylsilylchloride (150.7 mg, 1.0 mmol). The mixture was stirred at ambient temperature for 6 hr under inert atmosphere and then treated with saturated sodium bicarbonate solution and extracted with ethyl acetate, dried over sodium sulfate, and evaporated to dryness. The crude product was purified using silica gel column chromatography using 2-5% MeOH in CHCl₃ to give 380 mg of the desired product 21.3.

¹H NMR (CDCl₃) δ 7.68 (s, 1H, H-6), 7.24 (d, J 11.4 Hz, H1"), 6.83 (s, 1H, H-1'), 5.85 (d, J 11.4 Hz, H2"), 4.14-3.72 (m, 4H, H-3', H-4', 2×H-5'), 0.99 (s, 12H, CH₃, (CH₃)₃), 0.18 (s, 6H, 2×CH₃)

2-(2-C-Methyl-β-D-ribofuranosyl)-methylamino-2,6-dihydro-7H-2,3,5,6-tetraazabenzo[cd]azulen-7-one (21.4)

Compound 21.3 (100 mg, 0.20 mmol) was added to 2M methylamine solution in THF (25 mL) in a pressure vessel. The vessel was tightly sealed and heated at 90° C. for 8 hr. After evaporation of the solvent and excess amine, the residue was re-dissolved in THF (20 mL). To this solution, tetrabutylammonium fluoride in THF (2 mL) was added and the solution stirred at room temperature for 4 hr. After careful evaporation of the solvent, the residue was purified on a silica gel column using 5-7% MeOH in CHCl₃ as eluent to give 46 mg of desired yellowish product.

¹H NMR (DMSO-d₆) δ 10.05 (br s. 1H, NM), 7.42 (s, 1H, H-6), 6.89 (d, J 11.7 Hz, H1"), 6.65 (br s, 1H, NH), 5.93 (s, 1H, H-1'), 5.61 (d, J 11.7 Hz, H2"), 5.19-5.00 (m, 3H, 3×OH), 3.90-3.3.63 (m, 4H, H-3', H-4', 2×H-5'), 3.32, (s, 3H, NCH₃), 0.80 (s, 3H, CH₃).

Example 24

4-Methoxy-2-(2-C-methyl-β-D-ribofuranosyl)-2,6-dihydro-7H-2,3,5,6-tetraazabenzo[cd]azulen-7-one (21.5)

To a solution of compound 21.3 (100.0 mg, 0.20 mmol) in anhydrous MeOH (25 mL) was added freshly prepared sodium methoxide (540.0 mg, 10.0 mmol). The resulting homogeneous solution was heated to reflux for 24 hr and then neutralized with DOWEX H⁺ resin and filtered. The neutral methanolic solution was evaporated and the residue was re-dissolved in THF. To this solution, tetrabutylammonium fluoride in THF (2 mL) was added and the mixture was stirred at room temperature for 4 hr. After careful evaporation of the solvent, the residue was purified on a silica gel column to give 38 mg of the desired yellowish product ¹H NMR (CD₃OD) δ 7.64 (s, 1H, H-2), 7.00 (d, J 11.7 Hz, H1"), 6.129 (s, 1H, H-1'), 5.73 (d, J 11.7 Hz, H2"), 3.81-4.13 (m, 7H, H-3', H-4', 2×H5', OCH₃), 0.92 (s, 3H, CH₃).

Example 25

2-(2-C-Methyl-β-D-ribofuranosyl)-2,6-dihydro-7H-2,3,5,6-tetraazabenzo[cd]azulene-7-thione (23.2)

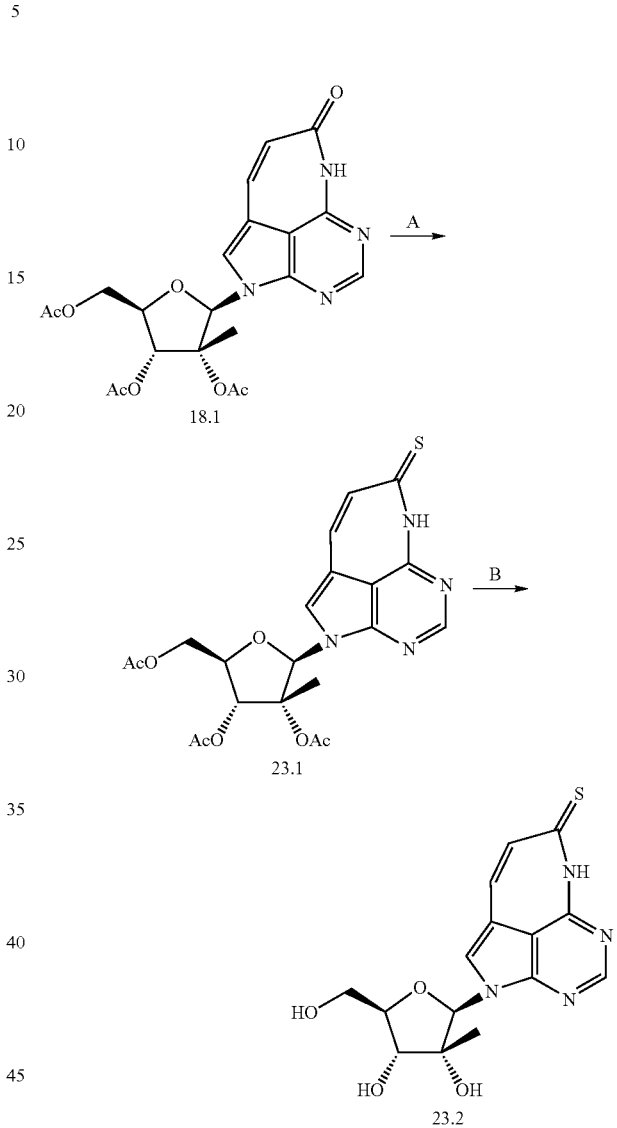

Example 25

Step A: 2-(2-C-Methyl-2,3,5-tri-O-acetyl-β-D-ribofuranosyl)-2,6-dihydro-7H-2,3,5,6-tetraazabenzo[cd]azulene-7-thione (23.1)

Compound 18.1 (250 mg, 0.54 mmol) was dissolved in dioxane (5 mL) and pyridine (7 mL) was added, followed by phosphorus pentasulfide (242 mg, 0.5 mmol). The mixture was heated at reflux for 24 hr then the solvent was evaporated and the residue was washed with pyridine (3×4 mL). The combined washings were evaporated and the residue was dissolved in 50 mL CHCl₃ and washed with 30 mL 10% aqueous sodium bicarbonate followed by water. The organic phase was dried over anhydrous sodium sulfate, filtered, evaporated and the residue (180 mg) containing 23.1 was used immediately in the next step.

Example 25

Step B: 2-(2-C-Methyl-β-D-ribofuranosyl)-2,6-dihydro-7H-2,3,5,6-tetraazabenzo[cd]azulene-7-thione (23.2).

To a suspension of compound 23.1 (180 mg, 0.38 mmol) in 4 mL ethanol was added 0.22 mL of 1N sodium hydroxide solution in water. The mixture was stirred at room temperature for 1.5 hr. after which time the pH was brought to 6 with acetic acid and the solvent evaporated. The residue was purified on silica gel column (10:1 CH$_2$Cl$_2$:MeOH) to afford 30 mg of product 23.2. $^1$H NMR (DMSO-d$_6$) δ 10.49 (s, 1H), 8.52 (s, 1H), 7.50 (s, 1H), 7.00 (d, J 12 Hz, 1H), 6.08 (s, 1H), 5.65 (d, J 12 Hz, 1H), 5.18 (m, 3H), 3.82 (m, 3H), 3.68 (m, 1H), 0.73 (s, 3H).

Example 26

2-(2-C-Methyl-β-D-ribofuranosyl)-6,7-dihydro-2H-2,3,5,6-tetraazabenzo[cd]azulene (24.2)

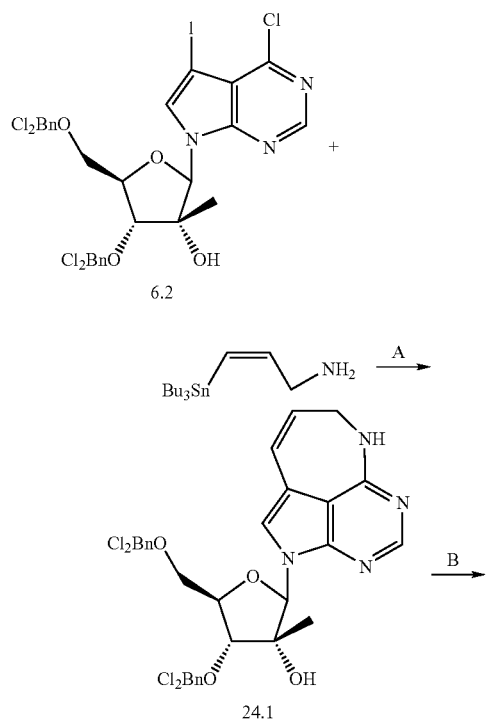

Example 27

Step A: 2-[3,5-Bis-O-(2,4-dichlorophenylmethyl)-2-C-methyl-β-D-ribofuranosyl]-6,7-dihydro-2H-2,3,5,6-tetraazabenzo[cd]azulene (24.1)

To compound 6.2 (372 mg, 0.5 mmol) and tri-n-butyltin allylamine (prepared according to the literature procedure in Corriu et. al. *Journal of Organic Chemistry* 1993, 58, 1443-1448) in 10 mL anhydrous toluene was added tetrakis (triphenylphosphine) palladium [0] and the mixture was heated at reflux for 5 hr. The solvent was evaporated and the residue dissolved in CH$_2$Cl$_2$ and loaded on a silica gel column and eluted successively with 75:1, 60:1, 40:1 CH$_2$Cl$_2$:MeOH. Pooling and evaporation of the fractions afforded 160 mg of product 24.1.

Example 27

Step B: 2-(2-C-Methyl-β-D-ribofuranosyl)-6,7-dihydro-2H-2,3,5,6-tetraazabenzo[cd]azulene (24.2)

To compound 24.1 (160 mg, 0.25 mmol) in CH$_2$Cl$_2$ (10 mL) at −78° C. was added 1M solution of boron trichloride in CH$_2$Cl$_2$ dropwise over 5 minutes and the solution stirred at −78° C. for 2.5 h and then at −25° C. for 3 hr. To this mixture was added 25 mL of 1:1 v/v CH$_2$Cl$_2$:MeOH and the solution stirred at −15° C. for 30 minutes. The mixture was brought to room temperature and the solvent was evaporated under reduced pressure. The residue was co-evaporated with MeOH (5×10 mL) and a 10 mL MeOH solution was neutralized with NH$_4$OH and evaporated again. The residue was adsorbed on 2 g silica gel and loaded on a silica column and eluted successively with 50:1, 20:1 and 15:1 CH$_2$Cl$_2$:MeOH. Fractions eluting at 20:1 and 15:1 were collected, Pooling of fraction and evaporation gave 16 mg product 24.2. $^1$H NMR (DMSO-d$_6$) δ 8.10 (s, 1H), 7.51 (s, 1H), 7.30 (t, 1H), 6.61 (d, J 9 Hz, 1H), 6.11 (s, 1H), 5.71 (dt, J 6, 12 Hz, 1H), 5.08 (m, 3H), 3.86 (m, 5H), 3.78 (m, 1H), 0.72 (s, 3I).

Example 27

9-Methoxy-2-(2-C-methyl-β-D-ribofuranosyl)-6,7,8,9-tetrahydro-2H-2,3,5,6-tetraazabenzo[cd]azulene (25.1)

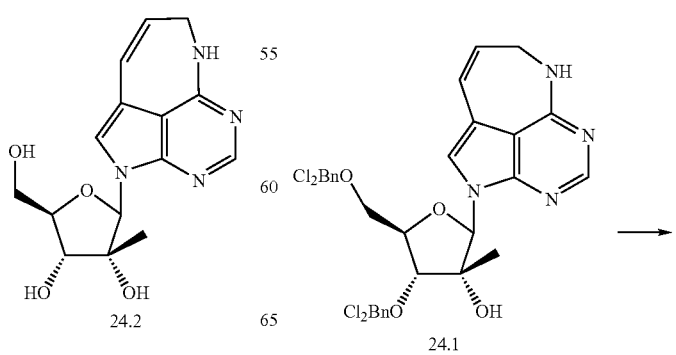

-continued

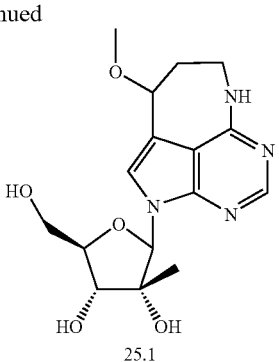

25.1

The slower moving fi-action from Step B in Example 27, Step B was isolated to afford 8 mg of ether 25.1. $^1$H NMR (DMSO-d$_6$) δ 8.00 (s, 1H), 7.53 (m, 3H), 6.11 (s, 1H), 5.11 (m, 4H), 4.43 (m, 1H), 3.97 (m, 1H), 3.84 (m, 3H), 3.66 (m, 2H), 3.26 (s, 3H), 0.68(s, 3H).

Example 28

Nucleoside Monophosphates

To the compound appropriate nucleoside (0.156 mmol) (dried over P$_2$O$_5$ in vacuo overnight) was added trimethyl phosphate (1.5 mL). The mixture was stirred overnight in a sealed container containing 4A molecular sieves. It was then cooled to 0° C. and phosphorous oxychloride (35.8 μL, 2.5 eq.) was added via syringe. The mixture was stirred for 3 hr at 0° C., then the reaction was quenched by addition of tetraethylammonium bicarbonate (TEAB) (1M) (1.5 mL) and water (15 mL). The aqueous solution was washed with CHCl$_3$ and ether then lyophilized. The crude product was purified by HPLC using a C18 column with water and 5% acetonitrile in water to provide the monophosphate as a triethylammonium salt after lyophilization.

Example 29

5'-p-Phenyl Methoxyalaninylphosphate Prodrugs

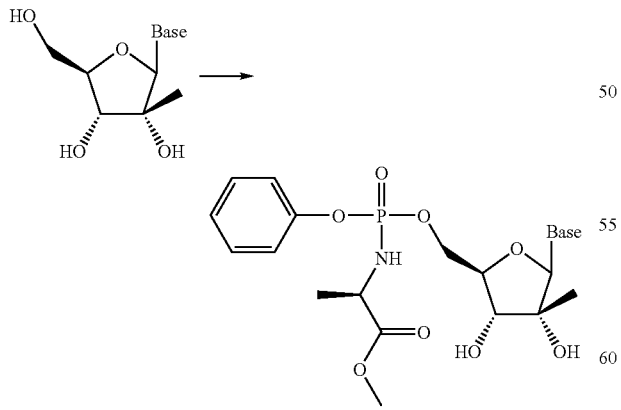

To a solution of compound the appropriate nucleoside (0.6 mmol) in anhydrous THF (5 mL) was added phenyl methoxyalaninylphosphorochloridate (40 mg, 5 eq.) (freshly prepared following the literature procedure: *J. Med. Chem.* 1993, 36, 1048-1052 and *Antiviral Research*, 1999, 43, 37-53) and 1-methylimidazole (95 μL, 10 eq.) at room temperature under argon. The reaction was followed by TLC. After 36 hr, the reaction mixture was evaporated and the residue was purified on silica gel with 0-10% MeOH in CH$_2$Cl$_2$ as eluent to provide a 1:1 mixture of diastereomers.

Example 30

2-[5-O-Bis(pivaloyloxymethyl)phoshoryl-prodrugs

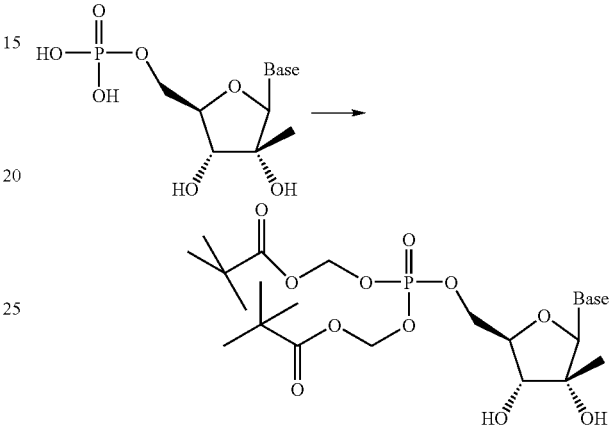

To a solution of triethylammonium salt of compound nucleoside monophosphate (0.024 mmol) in anhydrous MeOH (0.5 mL) was added tributylstannyl methoxide (14 μL, 2 eq.) at room temperature under argon. The reaction mixture was stirred at room temperature for 30 min then evaporated and co-evaporated with acetonitrile three times. The residue was dissolved in anhydrous acetonitrile (3 mL) and tetrabutylammonium bromide (15.5 mg, 2 eq.) and iodomethyl piovalate (58 mg, 10 eq) were added. The reaction mixture was heated at reflux for 1 hr cooled to room temperature and the solvent was evaporated. The residue was purified on a silica gel column with 1-5% MeOH in CH$_2$Cl$_2$ to provide the prodrug.

Example 31

Nucleoside Diphosphates

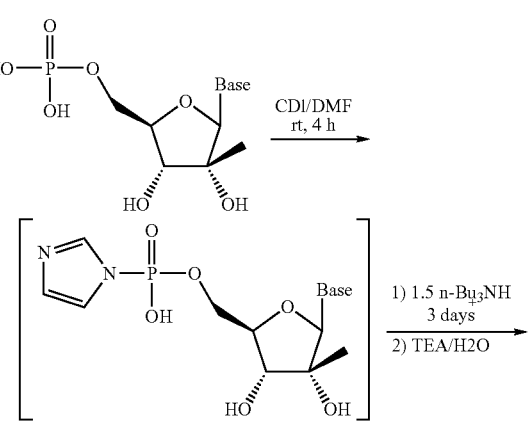

-continued

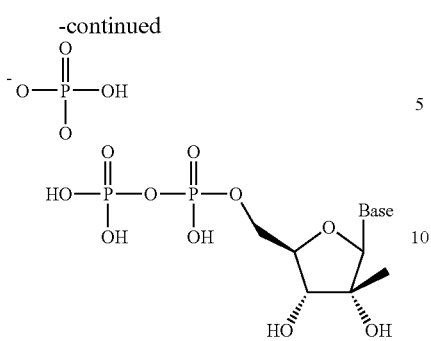

To a solution of the triethylammonium salt of 5'-monophosphate (0.031 mmol) [dried by coevaporation with anhydrous DMF twice (2×1 mL)] in 0.5 mL of anhydrous DMF was added N,N'-carbonyldiimidazole (25 mg, 5 eq.) at room temperature under argon. The reaction mixture was stirred at room temperature for 4 hr after which analytical TLC showed no starting material. Then tributylammonium phosphate salt (1.5 n-Bu₃N/phosphate, which was prepared (see PCT, WO 88/03921) and further dried by coevaporation with anhydrous DMF three times) was added to the above solution. The reaction was followed by TLC and typically after 3 days, LC-MS showed significant (>50%) conversion to product. The reaction was quenched with 1 mL of triethylamine, 1 mL of water, and stirred at room temperature for 40 min. The crude product was purified by reverse phase HPLC to provide pure product 29.1.

Examples 32-42

Nucleoside 5'-triphosphates

To an ice-cold mixture of nucleoside (0.1 mmol) in trimethyl phosphate (1 mL, anhydrous) was added $POCl_3$ (18.6 μL, 0.2 mmol) and the mixture stirred at 0° C. for 1 h. ributyl amine (71.5 μL, 0.3 mmol) was added, followed by acetonitrile (0.1 mL, anhydrous) and tributylammonium pyrophosphate (182 mg, 0.4 mmol). After 30 min. the reaction was quenched with ice-cold 1M triethylammonium bicarbonate buffer (5 mL, 1M, pH 8.5). The products were purified by HPLC.

| Example Number | Structure | Calculated Molecular Weight | Observed m/z [M − H]⁻ |
|---|---|---|---|
| 32 | 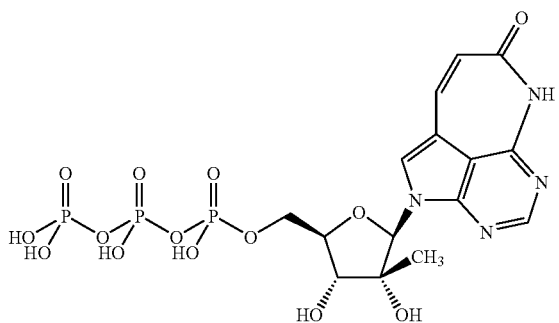 | 572.251 | 571.6 |
| 33 | 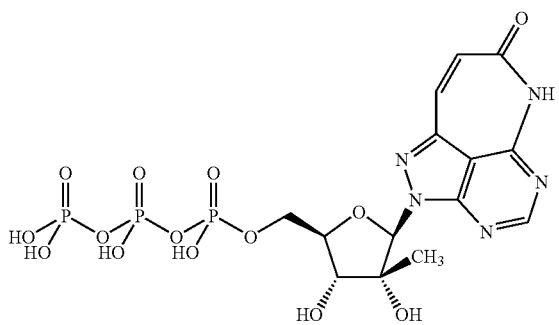 | 573.239 | 572.0 |
| 34 | 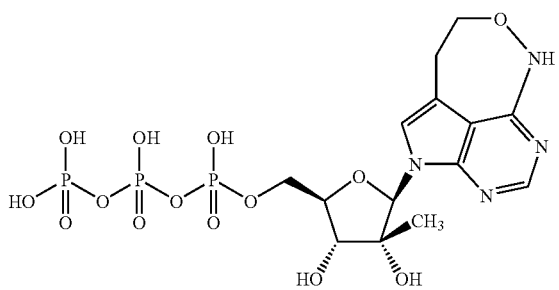 | 562.26 | 561.9 |

-continued

| Example Number | Structure | Calculated Molecular Weight | Observed m/z [M − H]⁻ |
|---|---|---|---|
| 35 | 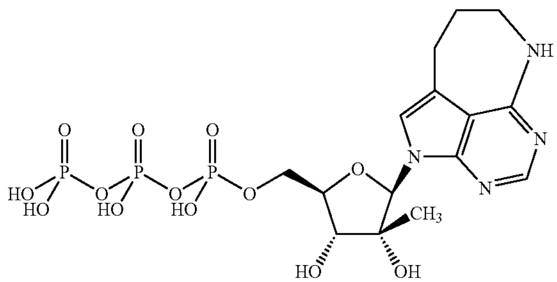 | 560.284 | 559.9 |
| 36 | 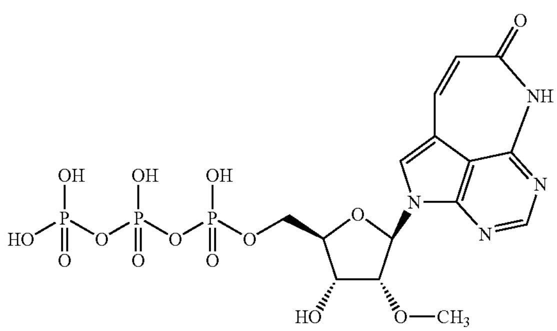 | 572.251 | 571.8 |
| 37 | 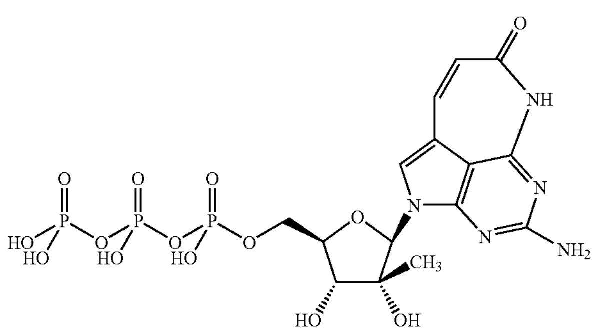 | 587.266 | 586.9 |
| 38 | 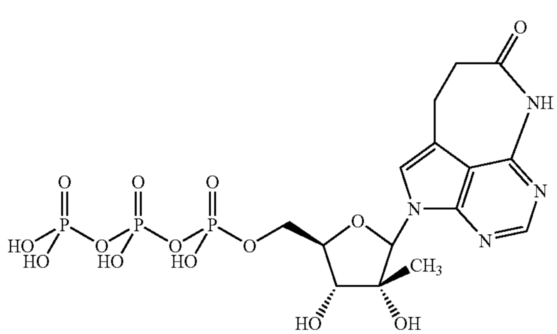 | 574.267 | 573.9 |

-continued

| Example Number | Structure | Calculated Molecular Weight | Observed m/z [M − H]⁻ |
|---|---|---|---|
| 39 | 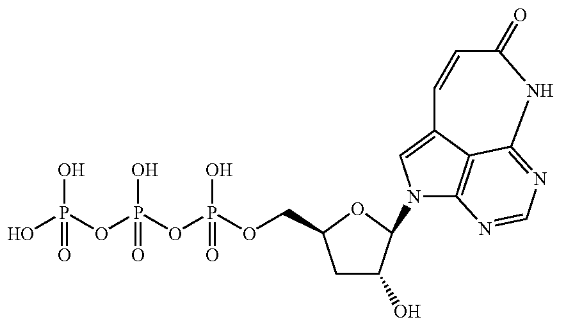 | 542.225 | 541.1 |
| 40 | 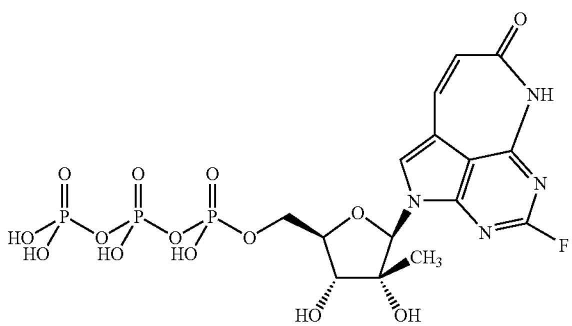 | 590.241 | 589.8 |
| 41 | 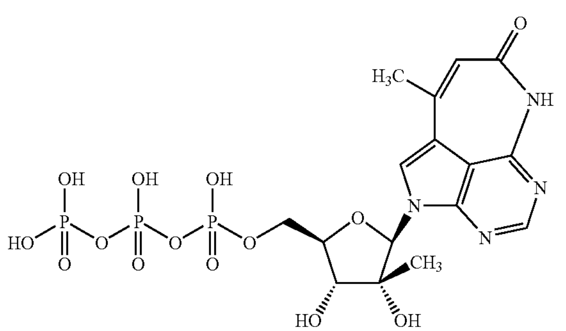 | 586.278 | 585.8 |
| 42 | 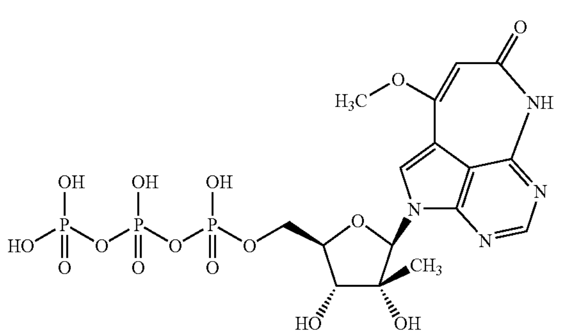 | 602.277 | 601.9 |

Example 43

Nucleoside-5'triphosphate Mimic 2-(5-α-P$_f$-borano-β,γ-difluoromethylene)triphoshono 2-C-methyl-β-D-ribofuranosyl)-2,6,8,9-tetrahydro-7-oxa-2,3,5,6-tetraazabenzo[cd]azulene (43.2)

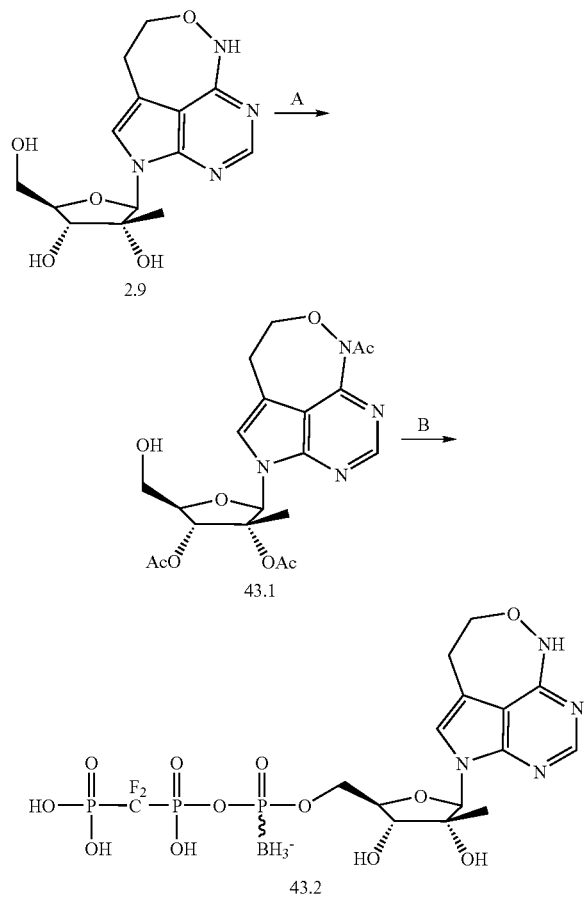

Example 43 step A 2-(2-C-methyl-2,30di-O-acetyl-β-D-ribofuranosyl)-2,6,8,9-tetrahydro-7-oxa-2,3,5,6-tetraazabenzo[cd]azulene (43.1)

To a solution of compound 2.9 from example 2, step G (76 mg, 0.24 mmol) in pyridine (2.0 mL) was added tert-butyldimethylsilylchloride (60 mg, 0.38 mmol). The mixture was stirred at ambient temperature for 16 hr under inert atmosphere. Added acetic anhydride (0.44 mL, 4.32 mmol), nad stirred for 3 h at room temperature. Added triethylamine (0.61 mL, 6.0 mmol), and DMAP (35 mg, 0.29 mmol). The mixture was stirred overnight at room temperature, then evaporated and the residue partitioned between water (20 mL) and CH$_2$Cl$_2$ (60 mL). The organic layer was dried over Na$_2$SO$_4$. Solvents were evaporated in vacuo. The resulted crude product was dried on high vacuum for 2 h and redissolved in THF (2.0 ml) and cooled to 0° C. and added 1.0M solution of TBAF in THF (0.6 mmol) and stirred at 0° C. for 1 h. Reaction was quenched by adding absolute ethanol (2 ml), and solvents were evaporated. The residue left was redissolved in dichloromethane and washed with water. The organic portions were dried over Na$_2$SO$_4$ and filtered, evaporated and crude product was purified by silicagel column chromatography using 1-2% methanol in dichloromethane to give 43.1 as light yellow foam (57 mg).

$^1$H NMR (DMSO-d$_6$) d 8.57 (s, H-2, 1H), 7.70 (s, H-6, 1H), 6.62 (s, H-1', 1H), 5.39 (d J 5.7, H-3', 1H), 5.23 (t, J 5.7, 5'-OH, 1H), 4.52 (br s, OCH$_2$CH$_2$, 2H), 4.09-4.13 (m, H-4', 1H), 3.62-3.81 (m, H-5', 2H), 3.08-3.1 (m, OCH$_2$CH$_2$, 2H), 2.51 (s, N—COCH$_3$, 3H), 2.08, 2.04 (each s, 2×O—COCH$_3$, 6H), 1.34 (s, CH$_3$, 3H).

Example 43

Step B: 2-(5-α-P$_f$-borano-β,γ-difluoromethylene) triphoshono 2-C-methyl-β-D-ribofuranosyl)-2,6,8,9-tetrahydro-7-oxa-2,3,5,6-tetraazabenzo[cd]azulene (43.2)

2-Chloro-4H-1,3,2-benzodioxaphosphorin-4-one (29 mg, 0.15 mmol) was added to a stirred solution of 43.1 (43 mg, 0.1 mmol) in anhydrous DMF (0.5 mL) and pyridine (0.1 mL) at 0° C. under argon. The reaction mixture was stirred at room temperature for 2 h, cooled with ice bath. Tributylamine (65 uL, 0.28 mmol) was added, followed by addition of (difluoromethylene)diphosphonic acid bis(tributylammonium) salt (89 mg, 0.15 mmol) in DMF (0.5 mL). The reaction mixture was stirred at room temperature for 2 h and cooled with ice. Borane-diisopropylethylamine complex (377 ul, 2.11 mmol) was added, and the resulting mixture was stirred at room temperature for 6 h, cooled with ice, and quenched by slow addition of water (2 mL). The mixture was stirred at room temperature for 1 h, diluted with water (3 ml), extracted two times with chloroform and aqueous portion was concentrated to about 2 ml. Aqueous ammonia (33%) (2 ml) was added and stirred at room temperature for 10 h and ammonia was evaporated and the remaining aqueous portion was analysed by LCMS. LCMS showed the presence of two diastereoisomers of 43.2. MS m/z 592.1 [M-H]

Example 44

HCV Replicon Assays

Doubling or ½-log dilutions of each compound were made in DMSO, and aliquots were transferred to 96-well microplates to give a final concentration range of 100-400 μM downwards in the presence of a constant concentration of 1% DMSO (ELISA and Reporter methods) or 0.4% DMSO (hybridization method). The inhibitory activity of these was assessed by three methods in Huh-7 cells transfected with replicons coding for non-structural (NS) proteins of HCV.

Replicon ELISA method: Huh-7 cells containing an HCV NS3-NS5b replicon were seeded into microplates containing compound dilutions at a concentration of 20,000 cells per well. After 3 days incubation the cell monolayers were washed and fixed with 1:1 acetone/MeOH. An ELISA was performed on the fixed cell sheets by the sequential addition of HCV-specific monoclonal antibody, horseradish peroxidase-conjugated secondary antibody and substrate solution, with thorough washing between additions. The colour development reaction was stopped with 12.5% sulphuric acid and the plates read at 490 nm. The monolayers were then washed, dried and stained with carbol fuchsin for microscopic assessment of cytotoxicity.

Replicon reporter method: Huh-7 cells containing a replicon expressing HCV NS3-NS5b plus a reporter gene were seeded into the test microplates at a concentration of 15,000 cells per well. After 2 days incubation, the viability of the cells was assessed by the addition of Resazurin (Sigma TOX-8) to all wells and reading the plates at 595 nm 3 hours post addition. The signal from the reporter gene product was measured immediately thereafter.

Replicon hybridization and cytotoxicity method: Huh-7 cells containing an HCV NS3-NS5b replicon were seeded into microplates containing compound dilutions at a concentration of 5,000 cells per well. After 3 days incubation the media was replaced with MTS solution and cytotoxicity was assessed by color development. After reading the plates at 490 nm, the MTS solution was aspirated and the cells were lysed and hybridized against HCV sequences using a chemiluminescent readout.

Data analysis: The mean reading of duplicate wells at each compound concentration was expressed as a percentage of the mean value for compound-free control wells. Percentage inhibition was plotted against concentration for each compound, and the 50% inhibitory concentration ($IC_{50}$) was calculated.

Compounds of Examples 1-27 were typically active in replicon assays in the range of 5 to >1000 μM Example 45

Huh-7 and Vero Cells: The compounds were additionally assessed for cytotoxicity in exponentially growing Huh-7 and Vero cell cultures. Doubling dilutions of the compounds were made, as described previously, and transferred to test microplates to give final concentrations of 500 μM downwards. Either Huh-7 cells or Vero cells were added at concentrations of 12,000 and 3,000 cells per well respectively. After incubation for 4 days at 37° C., MTT was added to all wells and the plates re-incubated for 2 hours. Acidified isopropanol was then added to all wells to lyse the cells and dissolve any formazan that had been produced. Absorbance was read at 570 nm, and the mean readings from duplicate test wells were expressed as percentages of the mean readings from compound free control wells. The 50% cytotoxic concentration ($CCID_{50}$) of each compound was calculated from the plot of percentage cell survival against compound concentration.

HFF Cells: Cells were seeded into microtiter plates containing ½-log dilutions of compounds at a concentration of 5,000 cells per well. After 3 days incubation the media was replaced with MTS solution in media and cytotoxicity was assessed by color development. Plates were read at 490 nm and $CC_{50}$s were calculated from percent inhibition as noted above.

Huh-7 and Vero Cells: The compounds were additionally assessed for cytotoxicity in exponentially growing Huh-7 and Vero cell cultures. Doubling dilutions of the compounds were made, as described previously, and transferred to test microplates to give final concentrations of 500 μM downwards. Either Huh-7 cells or Vero cells were added at concentrations of 12,000 and 3,000 cells per well respectively. After incubation for 4 days at 37° C., MTT was added to all wells and the plates re-incubated for 2 hours. Acidified isopropanol was then added to all wells to lyse the cells and dissolve any formazan that had been produced. Absorbance was read at 570 nm, and the mean readings from duplicate test wells were expressed as percentages of the mean readings from compound free control wells. The 50% cytotoxic concentration ($CCID_{50}$) of each compound was calculated from the plot of percentage cell survival against compound concentration.

HFF Cells: Cells were seeded into microtiter plates containing ½-log dilutions of compounds at a concentration of 5,000 cells per well. After 3 days incubation the media was replaced with MTS solution in media and cytotoxicity was assessed by color development. Plates were read at 490 ml and $CC_{50}$s were calculated from percent inhibition as noted above.

Huh-7 and Vero Cells: The compounds were additionally assessed for cytotoxicity in exponentially growing Huh-7 and Vero cell cultures. Doubling dilutions of the compounds were made, as described previously, and transferred to test microplates to give final concentrations of 500 μM downwards. Either Huh-7 cells or Vero cells were added at concentrations of 12,000 and 3,000 cells per well respectively. After incubation for 4 days at 37° C., MTT was added to all wells and the plates re-incubated for 2 hours. Acidified isopropanol was then added to all wells to lyse the cells and dissolve any formazan that had been produced. Absorbance was read at 570 nm, and the mean readings from duplicate test wells were expressed as percentages of the mean readings from compound free control wells. The 50% cytotoxic concentration ($CCID_{50}$) of each compound was calculated from the plot of percentage cell survival against compound concentration.

HFF Cells: Cells were seeded into microtiter plates containing ½-log dilutions of compounds at a concentration of 5,000 cells per well. After 3 days incubation the media was replaced with MTS solution in media and cytotoxicity was assessed by color development. Plates were read at 490 nm and $CC_{50}$s were calculated from percent inhibition as noted above.

Compounds of Examples 1-27 were typically cytotoxic in the range of 30 to >100 μM.

Example 46

HCV Polymerase Inhibition Assay

The C-terminal his-tagged full-length HCV (Bartenschlager 1b) polymerase gene was cloned and expressed in Sf9 cells by standard procedures. The enzyme was purified by nickel affinity chromatography followed by S-Sepharose column chromatography. Reactions contained 20 mM Tris HCl pH 7.0, 5 mM Hepes pH 7.0, 90 mM NaCl, 12.5 mM $MgCl_2$, 2% glycerol, 0.005% Triton X-100, 1.5 mM DTT, 0.4 U/μd RNasin, 20 μg/ml RNA corresponding to 696 nucleotides of the 3' non-coding region of the HCV 1b genome, 2 μM UTP (=$K_m$), 0.02 μCi/μl $^{33}$P-labelled UTP, a concentration equal to the $K_m$ of competing NTP (20 μM ATP, 3 μM GTP, or 0.5 μM CTP), 500 μM "non-competing" NTPs, and 100 nM HCV 1b polymerase (Bartenschlager, fall length enzyme) in a total volume of 25 µl. Reactions were initiated with the addition of enzyme and terminated after 2 hours with 5 µl 0.5 M EDTA. Stopped reactions were spotted onto either DEAE filter mats or DEAE 96-well filter plates (Millipore). Unincorporated nucleotides were washed from the filters. The filter mat was dried and sealed in a bag together with 10 ml of OptiScint HiSafe scintillation fluid. Filter plates were dried, and 75 ml OptiPhase scintillation fluid was added to each well. The remaining radioactivity was quantitated on a Wallac 1205 Betaplate counter or Wallac 1240 MicroBeta plate counter.

Compounds of Examples 32-42 were typically inhibitory of NS5B in the range of 100 to >1000 nM. Selected Examples were more active and displayed $IC_{50}$ values in the range of 30 to 100 nM.

What is claimed is:

1. A pharmaceutical composition comprising a therapeutically effective amount of at least one compound of the formula (I) which may be a D- or L-nucleotide or nucleoside in combination with a pharmaceutically acceptable carrier:

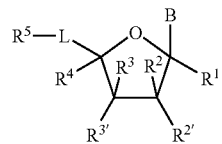
(I)

wherein $R^1$, $R^2$, $R^{2'}$, $R^3$, $R^{3'}$, and $R^4$ are independently H, F, Cl, Br, I, OH, SH, $NH_2$, NHOH, $NHNH_2$, $N_3$, COOH, CN, $CONH_2$, COOR, R, OR, SR, SSR, NHR, or $NR_2$, wherein $R^2$ or $R^{2'}$ are not both hydrogen;

L is O, S, NH, NR, $CY_2O$, $CY_2S$, $CY_2NH$, $CY_2$, $CY_2CY_2$, $CY_2OCY_2$, $CY_2SCY_2$, or $CY_2NHCY_2$, wherein Y is H, F, Cl, Br, alkyl, alkenyl, or alkynyl, and wherein alkyl, alkenyl, and alkynyl may each optionally contain one or more heteroatoms;

$R^5$ is OH, monophosphate, diphosphate, or triphosphate, or a phosphonate, phosphoamidate, or phosphoester thereof;

B is a base selected from:

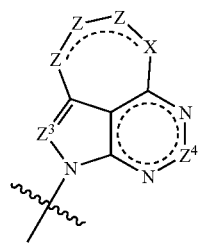

wherein dashed lines (---) indicate an optional π bond;

X is N, NH, or NR;

Z is C-G, O, >C=O, >C=S, or CH-G, wherein if Z is a participant in a π bond then Z is C-G, and when Z is not a participant in a π bond then Z is O, >C=O, >C=S, or CH-G;

$Z^1$ is C-G or CH-G, wherein if $Z^1$ is a participant in a π bond then $Z^1$ is C-G, and when $Z^1$ is not a participant in a π bond then $Z^1$ is CH-G;

$Z^2$ is C-G or CH-G, wherein if $Z^2$ is a participant in a π bond then $Z^2$ is C-G, and when $Z^2$ is not a participant in a π bond then $Z^2$ is CH-G;

$Z^3$ is CH or N;

$Z^4$ is C-G, >C=O, >C=S, >C=NH or >C=NR, wherein if $Z^4$ is a participant in a π bond then $Z^4$ is C-G, and if $Z^4$ is not a participant in a π bond then $Z^4$ is >C=O, >C=S, >C=NH or >C=NR;

each G is independently H, F, Cl, Br, I, OH, SH, $NH_2$, NHOH, $N_3$, COOH, CN, $CONH_2$, $C(S)NH_2$, $C(=NH)NH_2$, R, OR, SR, NHR, or $NR_2$; and each R is independently alkyl, alkenyl, alkynyl, aryl, acyl, or aralkyl, optionally containing one or more heteroatoms;

or a pharmaceutically acceptable salt thereof.

2. The pharmaceutical composition of claim 1 wherein $Z^4$ is a participant in a π bond, and base B is:

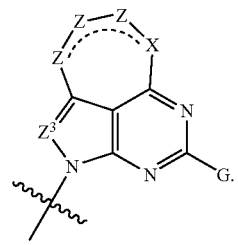

3. The pharmaceutical composition of claim 2 wherein G is H, F, Cl, Br, I, R, OR, SR, $NH_2$, NHR or $NR_2$, and R is alkyl.

4. The pharmaceutical composition of claim 2 wherein X is NH or NR, and base B is selected from:

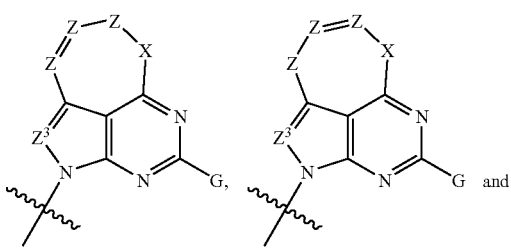

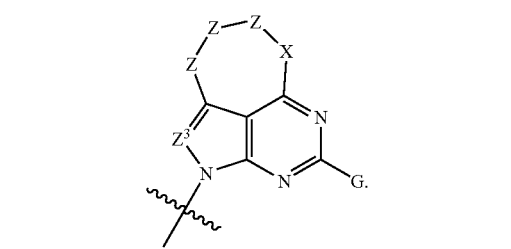

5. The pharmaceutical composition of claim 2 wherein X is N and base B is:

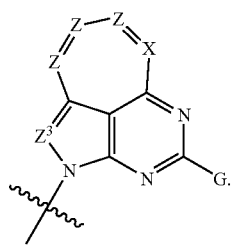

6. The pharmaceutical composition of claim 1 wherein $Z^4$ is not a participant in a π bond, and base B is selected from:

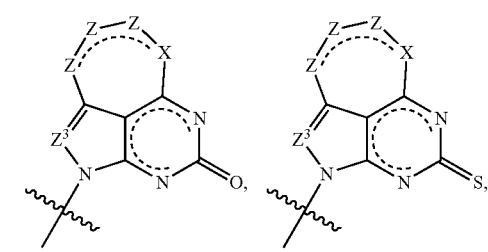

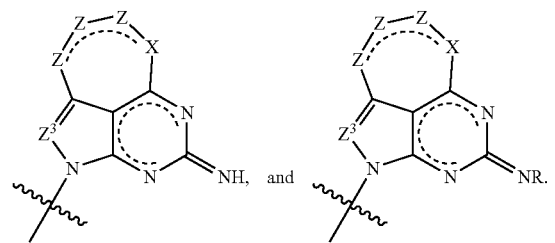

7. The pharmaceutical composition of claim 6 wherein X is NH or NR, and base B is selected from:

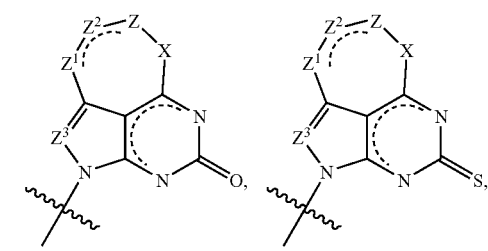

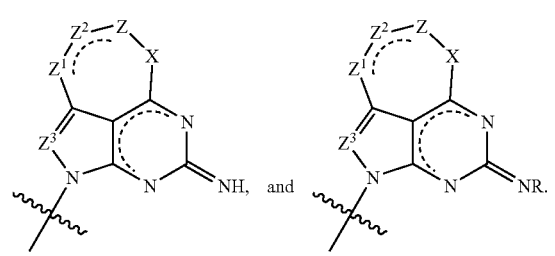

8. The pharmaceutical composition of claim 7 wherein X is NH, and base B is selected from:

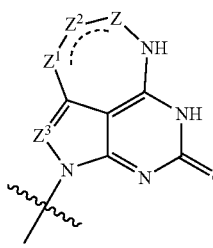 and 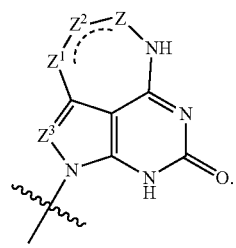

9. The pharmaceutical composition of claim 6 wherein X is NH or NR, and base B is selected from:

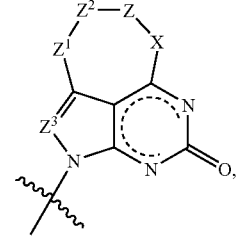 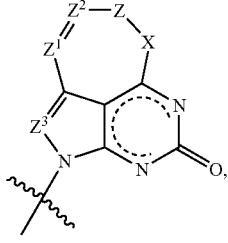

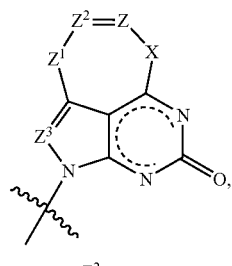 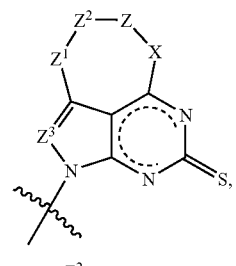

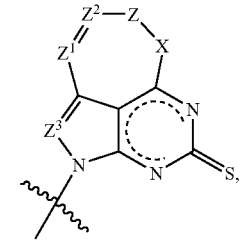

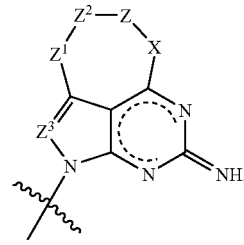 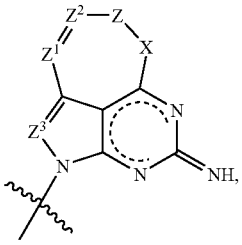

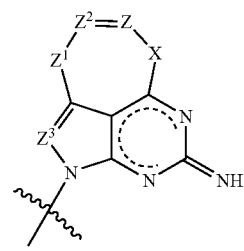 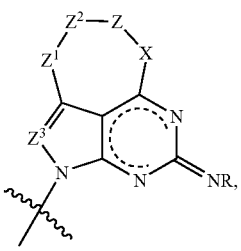

-continued
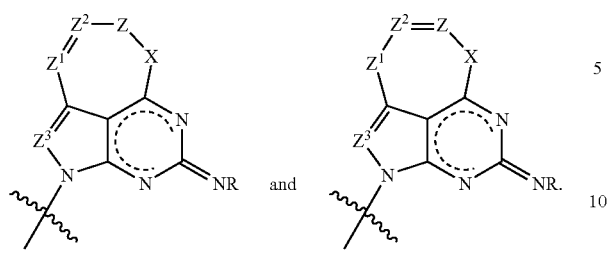
10. The pharmaceutical composition of claim 6 wherein X is N, and base B is selected from:
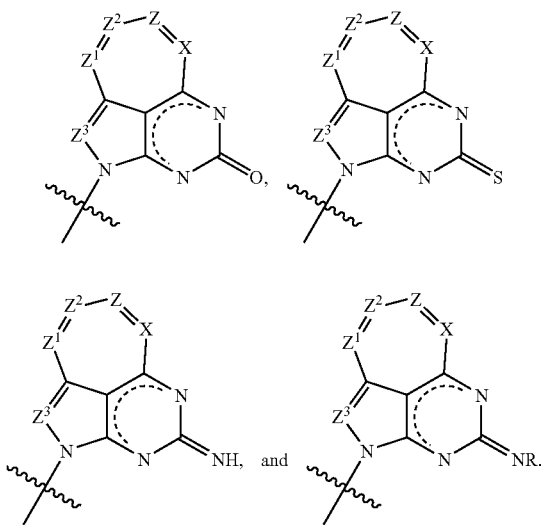
11. The pharmaceutical composition of claim 1 wherein the base B is selected from one of the following structures:
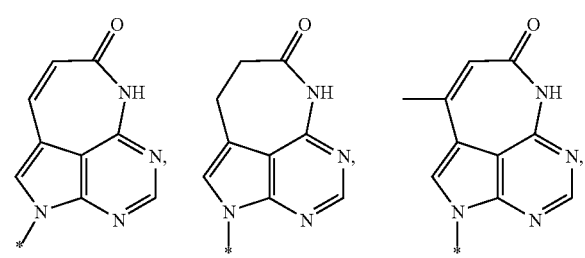
-continued
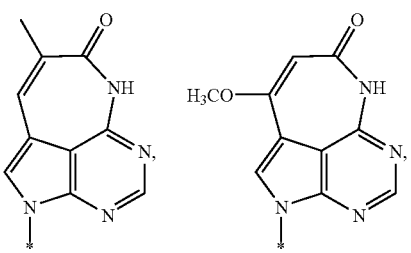
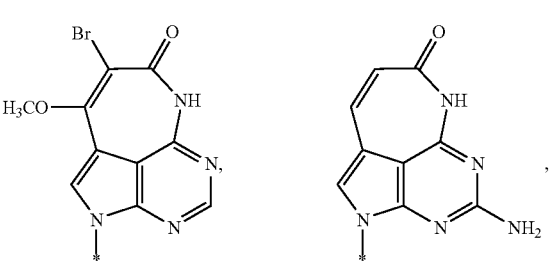
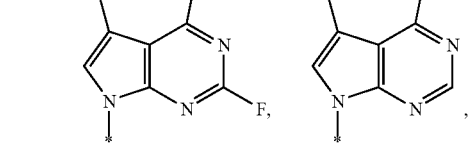
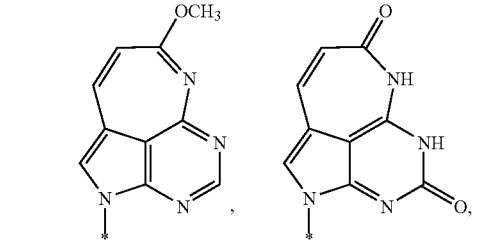
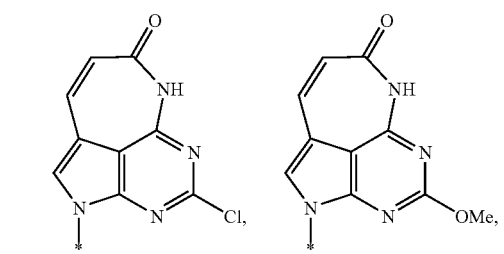
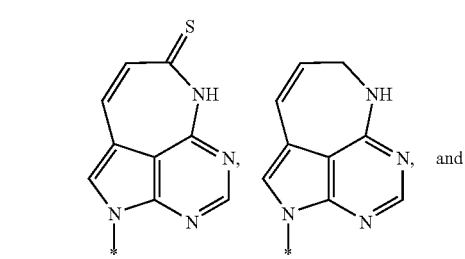

-continued

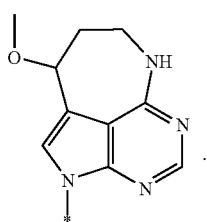

12. The pharmaceutical composition of claim 1 wherein the nucleotide or nucleoside has the structure

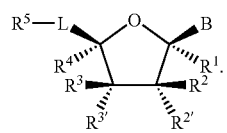

13. The pharmaceutical composition of claim 12 wherein $R^1$, $R^3$ and $R^4$ are hydrogen.

14. The pharmaceutical composition of claim 13 wherein $R^2$, $R^{2'}$ and $R^{3'}$ are independently H, F, Cl, Br, I, OH, $N_3$, CN, R or OR, and R is alkyl.

15. The pharmaceutical composition of claim 13 wherein $R^{2'}$ and $R^{3'}$ are OH.

16. The pharmaceutical composition of claim 15 wherein $R^2$ is H or methyl.

17. The pharmaceutical composition of claim 1 wherein $R^5$ is OH, monophosphate, or a monophosphonate thereof.

18. The pharmaceutical composition of claim 1, wherein the compound is selected from one of the following structures:

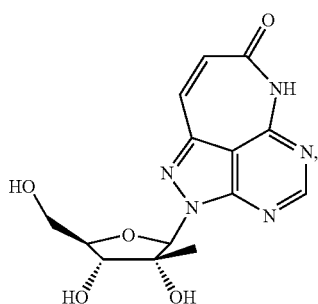

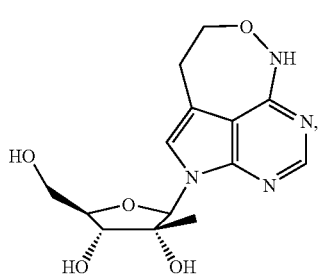

-continued

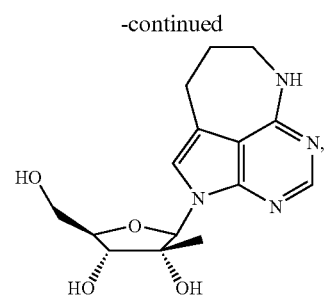

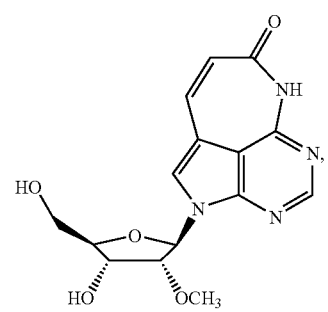

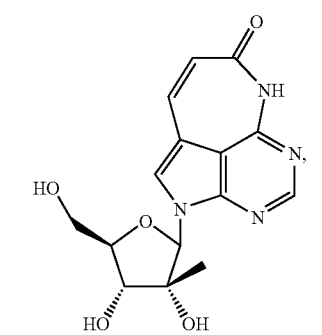

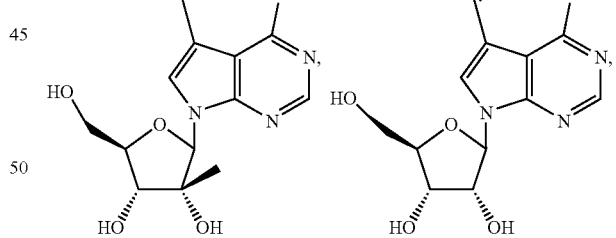

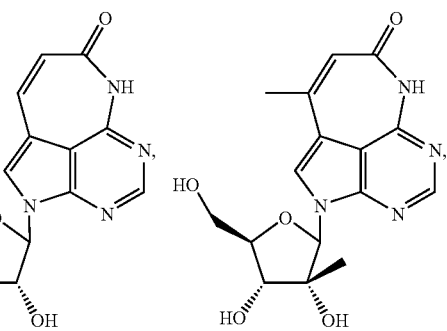

111
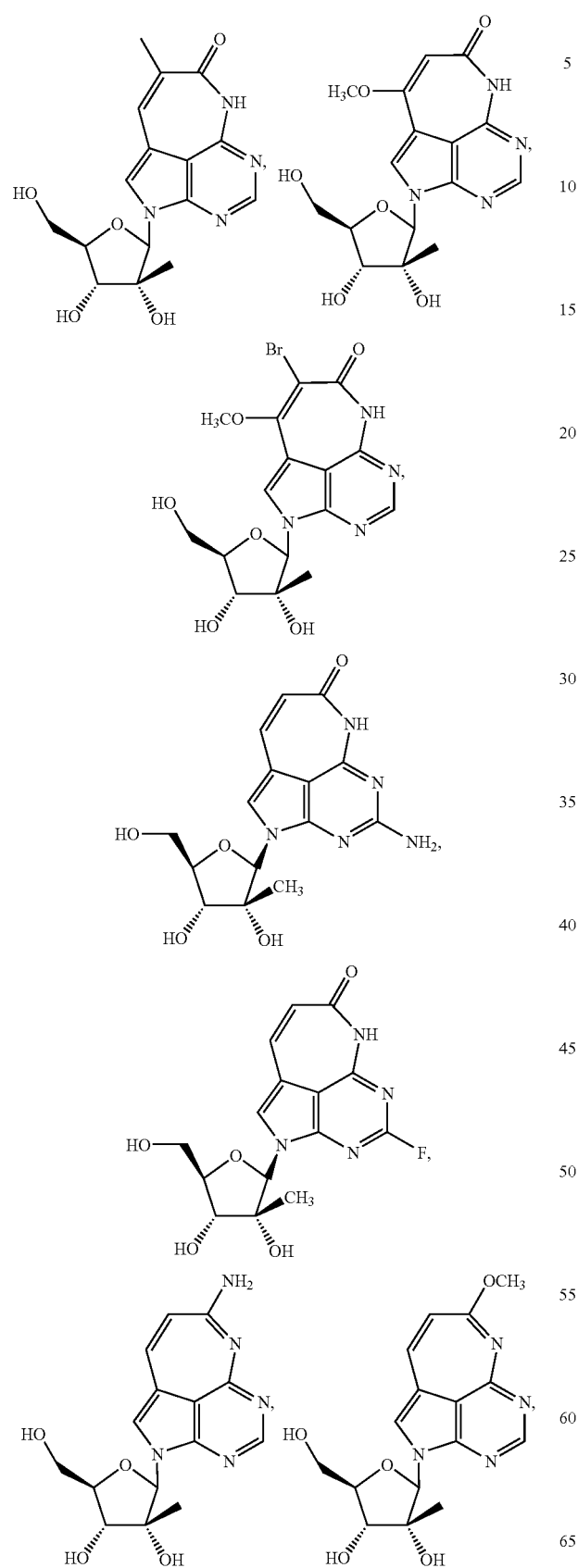
112
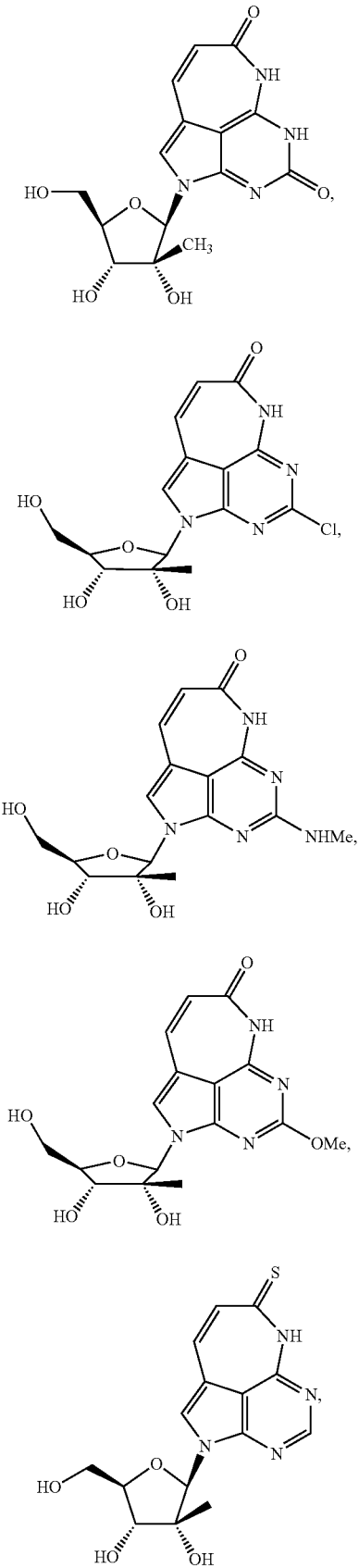

-continued
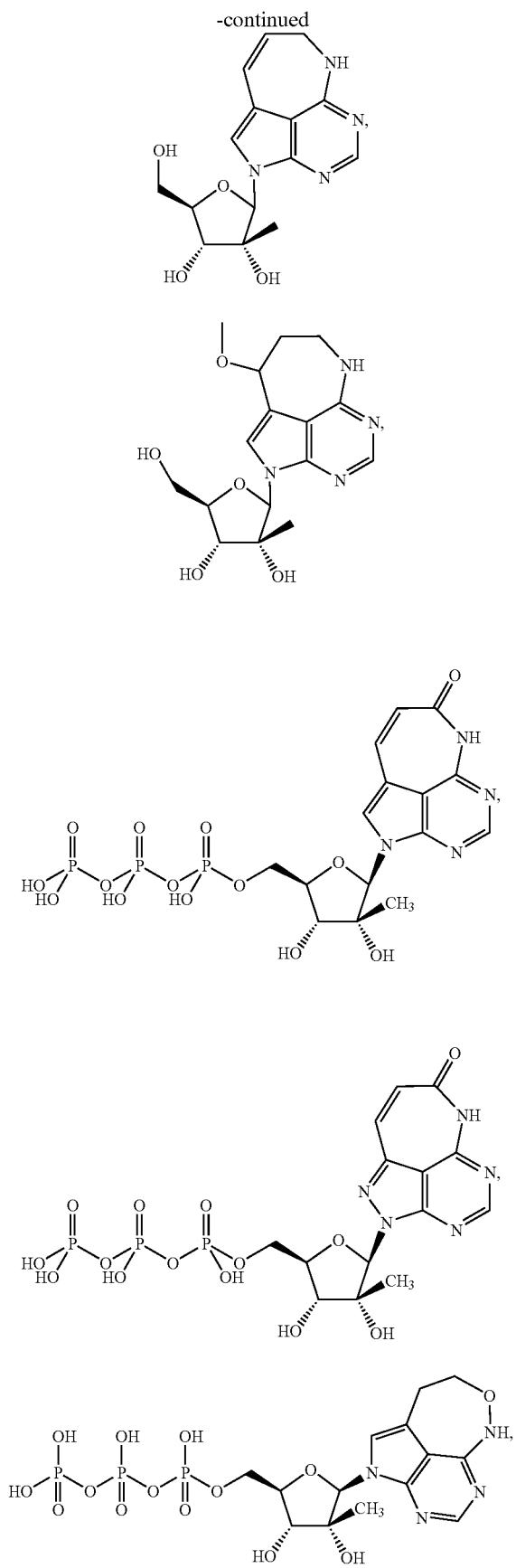
-continued
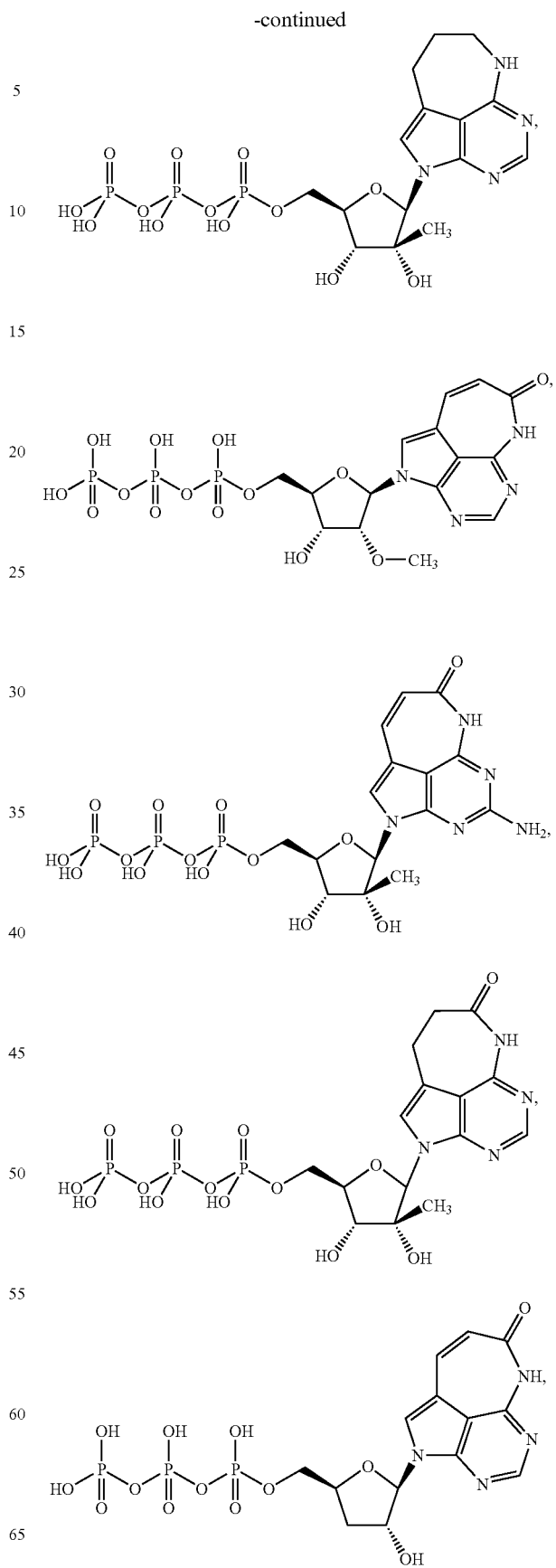

-continued
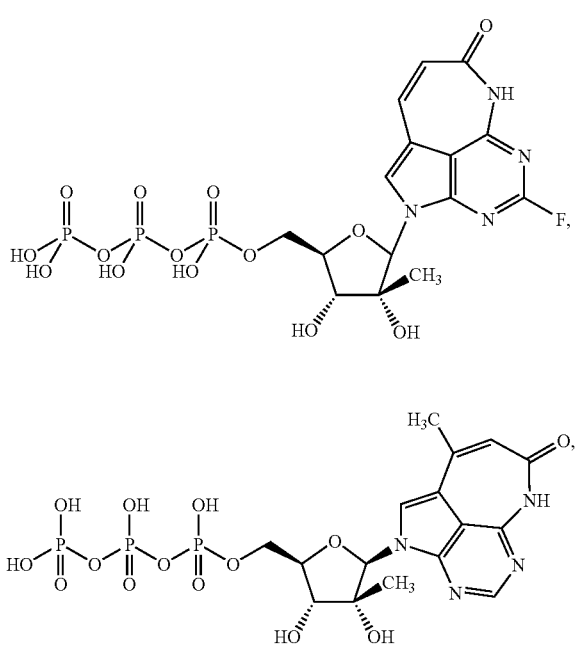
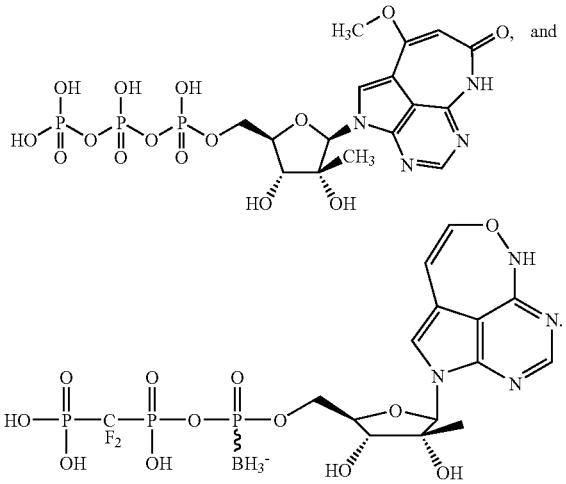
19. A method for treating a viral infection comprising administering a therapeutically effective amount of a pharmaceutical composition of claim 1 to a mammal in need thereof, wherein the viral infection is HBV or HCV.
* * * * *

UNITED STATES PATENT AND TRADEMARK OFFICE
CERTIFICATE OF CORRECTION

PATENT NO.        : 7,268,119 B2
APPLICATION NO.   : 11/674954
DATED             : September 11, 2007
INVENTOR(S)       : Phillip Dan Cook et al.

It is certified that error appears in the above-identified patent and that said Letters Patent is hereby corrected as shown below:

Claim 1.

Column 103, line 48, " 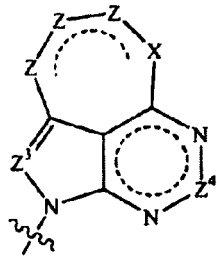 " should read as -- 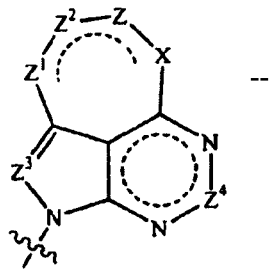 --

Claim 2.

Column 104, line 25, " 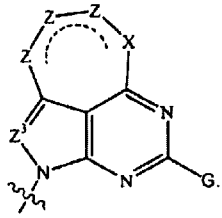 " should read as -- 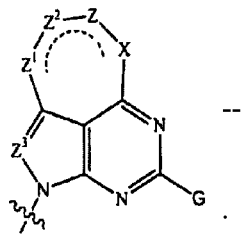 --

UNITED STATES PATENT AND TRADEMARK OFFICE
CERTIFICATE OF CORRECTION

PATENT NO. : 7,268,119 B2
APPLICATION NO. : 11/674954
DATED : September 11, 2007
INVENTOR(S) : Phillip Dan Cook et al.

It is certified that error appears in the above-identified patent and that said Letters Patent is hereby corrected as shown below:

Claim 4.

Column 104, line 45, " 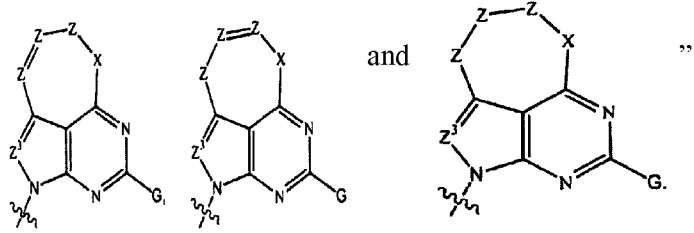 "

should read as -- 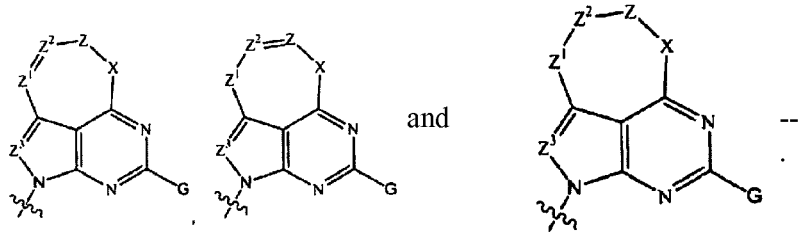 --

Claim 5.

Column 105, line 1, " 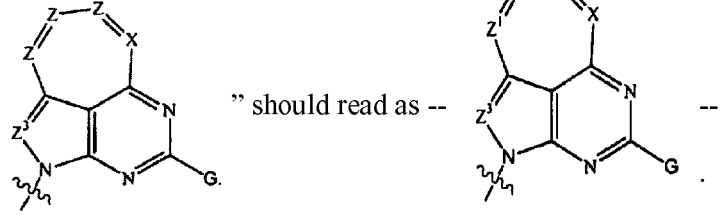 --

UNITED STATES PATENT AND TRADEMARK OFFICE
CERTIFICATE OF CORRECTION

PATENT NO. : 7,268,119 B2  Page 3 of 4
APPLICATION NO. : 11/674954
DATED : September 11, 2007
INVENTOR(S) : Phillip Dan Cook et al.

It is certified that error appears in the above-identified patent and that said Letters Patent is hereby corrected as shown below:

Claim 6.

Column 105, line 16, " 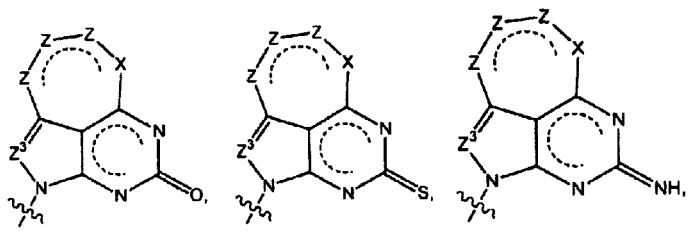

and 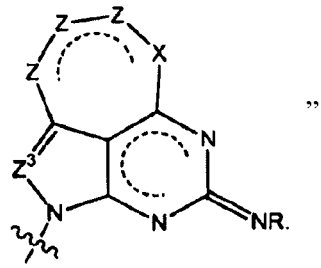 "

UNITED STATES PATENT AND TRADEMARK OFFICE
CERTIFICATE OF CORRECTION

PATENT NO. : 7,268,119 B2
APPLICATION NO. : 11/674954
DATED : September 11, 2007
INVENTOR(S) : Phillip Dan Cook et al.

It is certified that error appears in the above-identified patent and that said Letters Patent is hereby corrected as shown below:

should read as -- 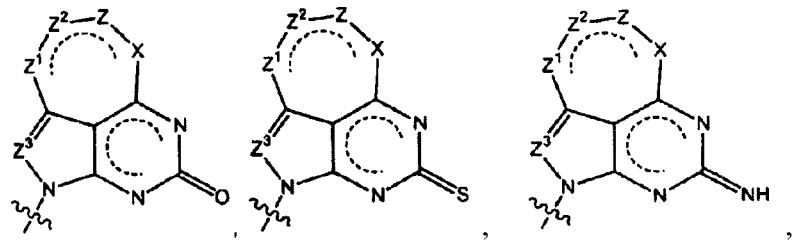, and 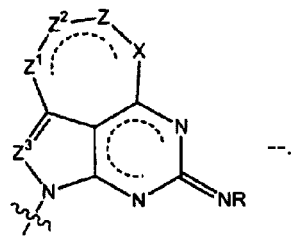 --.

Signed and Sealed this

Eighth Day of April, 2008

JON W. DUDAS
*Director of the United States Patent and Trademark Office*

UNITED STATES PATENT AND TRADEMARK OFFICE
CERTIFICATE OF CORRECTION

PATENT NO. : 7,268,119 B2
APPLICATION NO. : 11/674954
DATED : September 11, 2007
INVENTOR(S) : Phillip Dan Cook et al.

It is certified that error appears in the above-identified patent and that said Letters Patent is hereby corrected as shown below:

Column 14
Line 65, "C=O, or C–S;" should read as -- C=O, or C=S; --

Column 15
Line 40, "The substituents $^-$BH2GM$^+$ and BH3M$^+$ are ion pairs," should read as -- The substituents $^-$BH$_2$GM$^+$ and $^-$BH$_3$M$^+$ are ion pairs, --

Column 16
Line 9, "The substituents BH$_2$GM$^+$ and" should read as -- The substituents $^-$BH$_2$GM$^+$ and --

Column 17
Line 33, "a nitrogen atom phosphoamidates), or" should read as -- a nitrogen atom (phosphoamidates), or --

Column 17
Line 38, "drag moieties attached to a phosphate moiety" should read as -- drug moieties attached to a phosphate moiety --

Column 23
Line 51, "$Z^{61}$S CH$_2$, O, NH or NR;" should read as -- $Z^6$ is CH$_2$, O, NH or NR; --

Column 24
Line 44, "$Z^5$ $Z^6$ $Z^9$ are each independently CH$_2$," should read as -- $Z^5$, $Z^6$, $Z^9$ are each independently CH$_2$, --

Column 29
Line 33, "C-allyl, C-halogen, N, CNHR," should read as -- C-alkyl, C-halogen, N, CNHR, --

Column 32
Line 64, "Solid dosage form for bral administration include" should read as -- Solid dosage form for oral administration include --

UNITED STATES PATENT AND TRADEMARK OFFICE
CERTIFICATE OF CORRECTION

PATENT NO. : 7,268,119 B2
APPLICATION NO. : 11/674954
DATED : September 11, 2007
INVENTOR(S) : Phillip Dan Cook et al.

It is certified that error appears in the above-identified patent and that said Letters Patent is hereby corrected as shown below:

Column 37
Figures 2.6-2.8,

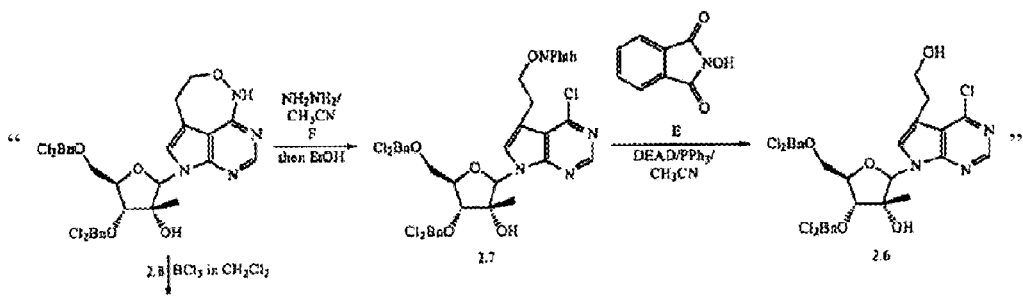

should read as

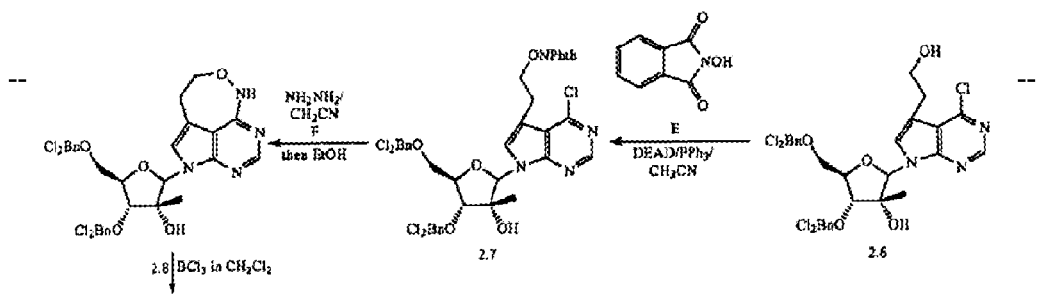

Column 39
Line 19, "Treatment of 2.2 with n-butyillithum in THF at" should read as -- Treatment of 2.2 with n-butyillithium in THF at --

UNITED STATES PATENT AND TRADEMARK OFFICE
CERTIFICATE OF CORRECTION

PATENT NO.       : 7,268,119 B2                         Page 3 of 4
APPLICATION NO.  : 11/674954
DATED            : September 11, 2007
INVENTOR(S)      : Phillip Dan Cook et al.

It is certified that error appears in the above-identified patent and that said Letters Patent is hereby corrected as shown below:

Column 43
Figures 2.2-4.1,

"
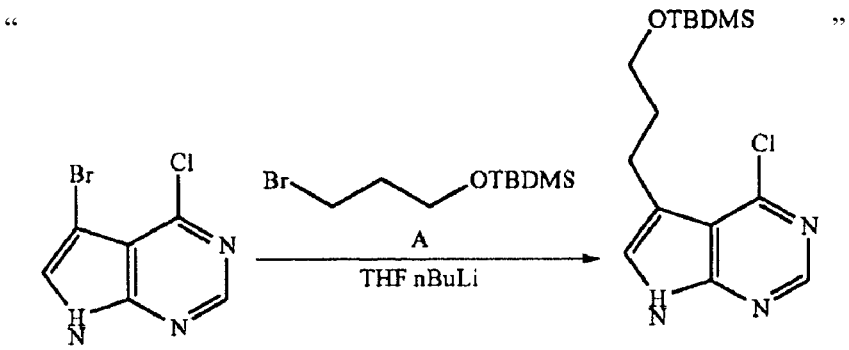
"

should read as

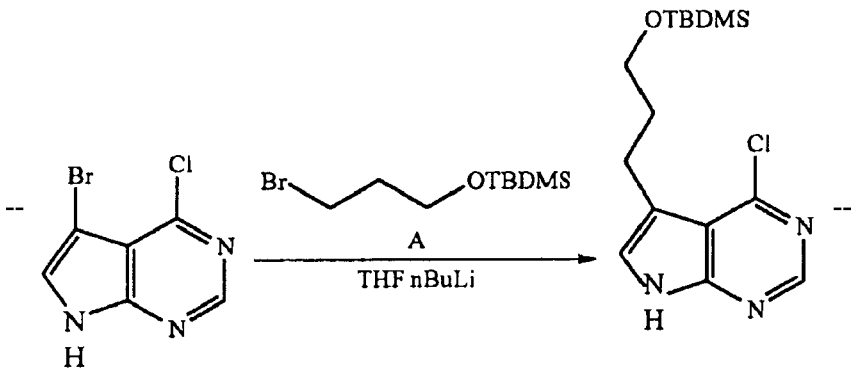

Column 57
Line 59, "(7.31)" should read as -- (7.3) --

Column 77
Line 10, "target stereoisometric mixture (B/Z, 3/1) as yellow solid" should read as -- target stereoisometric mixture (E/Z, 3/1) as yellow solid --

Column 79
Figure 20.1 A, "NANO$_2$,H$^+$/CuCl" should read as -- NaNO$_2$,H$^+$/CuCl --

UNITED STATES PATENT AND TRADEMARK OFFICE
CERTIFICATE OF CORRECTION

PATENT NO. : 7,268,119 B2
APPLICATION NO. : 11/674954
DATED : September 11, 2007
INVENTOR(S) : Phillip Dan Cook et al.

It is certified that error appears in the above-identified patent and that said Letters Patent is hereby corrected as shown below:

Column 87
Line 5, "2-(2-C-M 4-β-D-ribofuranosyl)-4-methylamino-2.6-" should read as
-- 2-(2-C-Methyl-β-D-ribofuranosyl)-4-methylamino-2.6- --

Column 87
Line 28, "ribofuranosyl)-methylamino" should read as
-- ribofuranosyl-4-methylamino --

Column 91
Line 17, "The slower moving fi-action from Step B" should read as -- The slower moving fraction from Step B --

Column 102
Line 16, "Plates were read at 490 ml" should read as -- Plates were read at 490 nm --

Column 103
Line 1, "fall length enzyme) in a total volume of" should read as -- full length enzyme) in a total volume of --

Signed and Sealed this

Tenth Day of February, 2009

JOHN DOLL
*Acting Director of the United States Patent and Trademark Office*